United States Patent
Wang et al.

(10) Patent No.: US 11,186,620 B2
(45) Date of Patent: *Nov. 30, 2021

(54) PEPTIDE DIRECTED PROTEIN KNOCKDOWN

(71) Applicant: University of British Columbia, Vancouver (CA)

(72) Inventors: Yu Tian Wang, Vancouver (CA); Xuelai Fan, Vancouver (CA); Jack Wuyang Jin, Vancouver (CA)

(73) Assignee: University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/366,420

(22) Filed: Mar. 27, 2019

(65) Prior Publication Data

US 2019/0315819 A1 Oct. 17, 2019

Related U.S. Application Data

(63) Continuation of application No. 14/431,060, filed as application No. PCT/CA2013/050741 on Sep. 27, 2013, now Pat. No. 10,287,333.

(60) Provisional application No. 61/706,506, filed on Sep. 27, 2012.

(51) Int. Cl.
| | |
|---|---|
| C07K 14/47 | (2006.01) |
| C12N 9/12 | (2006.01) |
| A61K 38/48 | (2006.01) |
| A61K 38/58 | (2006.01) |
| A61K 31/00 | (2006.01) |
| A61K 31/37 | (2006.01) |
| A61K 31/4365 | (2006.01) |
| A61K 38/17 | (2006.01) |
| A61K 45/06 | (2006.01) |
| A61K 38/00 | (2006.01) |

(52) U.S. Cl.
CPC .............. *C07K 14/47* (2013.01); *A61K 31/00* (2013.01); *A61K 31/37* (2013.01); *A61K 31/4365* (2013.01); *A61K 38/1709* (2013.01); *A61K 38/482* (2013.01); *A61K 38/4886* (2013.01); *A61K 38/58* (2013.01); *A61K 45/06* (2013.01); *C12N 9/12* (2013.01); *C12Y 207/11001* (2013.01); *C12Y 304/21* (2013.01); *C12Y 304/21031* (2013.01); *C12Y 304/21068* (2013.01); *C12Y 304/24029* (2013.01); *A61K 38/00* (2013.01); *C07K 2319/06* (2013.01); *C07K 2319/10* (2013.01); *C07K 2319/70* (2013.01); *C07K 2319/95* (2013.01)

(58) Field of Classification Search
None
See application file for complete search history.

(56) References Cited

U.S. PATENT DOCUMENTS

| | | | |
|---|---|---|---|
| 6,632,616 B2 | 10/2003 | Burke et al. | |
| 2005/0059597 A1* | 3/2005 | Tymianski | A61K 38/1709 514/17.3 |
| 2007/0244057 A1 | 10/2007 | Paulson et al. | |
| 2010/0016221 A1 | 1/2010 | Nukina et al. | |
| 2010/0311669 A1* | 12/2010 | Greene | C07K 16/32 514/19.3 |
| 2013/0065267 A1 | 3/2013 | Mao | |

FOREIGN PATENT DOCUMENTS

WO 2010/103515 A3 9/2010

OTHER PUBLICATIONS

中枢神经系统疾病治疗的新技术 -蛋白质和核酸的人脑转运 (New Techniques in Treatment of Central Nervous System Diseases—Transportation of Proteins and Nucleic Acids into Human Brain), Ailing Fu ed., Southwest China Normal University Press, pp. 96-98 (printed Jul. 17, 2018).
Aarts et al., "Treatment of ischemic brain damage by perturbing NMDA receptor-PSD-95 protein interactions," Science, 298: 846-850 (2002).
Altschul et al., "Gapped BLAST and PSI-BLAST: a new generation of protein database search programs," Nucleic Acids Res., 25(17): 3389-3402 (1997).
Altschul et al., "Basic Local Alignment Search Tool," J. Mol. Biol., 215: 403-410 (1990).
Baba, M., et al., "Aggregation of alpha-synuclein in Lewy bodies of sporadic Parkinson's disease and dementia with Lewy bodies", American Journal of Pathology 152(4): 879-884 (1998).
Backer et al., "Regulation of catabolism of microinjected ribonuclease A requires the amino-terminal 20 amino acids," Proc. Natl. Acad. Sci., 80: 2166-2170 (1983).
Banaszynski et al., "Conditional Control of Protein Function," Chemistry & Biology, 13: 11-21 (2006).
Banaszynski et al., "A Rapid, Reversible, and Tunable Method to Regulate Protein Function in Living Cells Using Synthetic Small Molecules," Cell, 126: 995-1004 (2006).

(Continued)

*Primary Examiner* — Adam Weidner
(74) *Attorney, Agent, or Firm* — Meunier Carlin & Curfman LLC

(57) ABSTRACT

In one aspect, the invention provides a peptide comprising a chaperone-mediated autophagy (CMA)-targeting signal domain; a protein-binding domain that selectively binds to a target cytosolic protein; and a cell membrane penetrating domain (CMPD). In another aspect, the invention provides methods for reducing the intracellular expression level of an endogenous target protein in vitro and in an animal, wherein the method involves administration of the peptide. Methods are also provided for treating a pathological condition in an animal, the methods comprising administering the peptide to the animal. In one embodiment, the pathological condition is a neurodegenerative disease. In another embodiment of the invention, the target cytosolic protein is death associated protein kinase I and the CMPD is protein transduction domain of the HIV-1 Tat protein.

11 Claims, 13 Drawing Sheets

Specification includes a Sequence Listing.

(56) References Cited

OTHER PUBLICATIONS

Banaszynski et al., "Chemical control of protein stability and function in living mice," Nature Medicine, 14(10): 1123-1127 (2008).
Barnham et al., "Neurodegenerative diseases and oxidative stress," Nat. Rev. Drug Discov., 3: 205-214 (2004).
Barber, S.C., et al., "Oxidative stress in ALS: A mechanism of neurodegeneration and a therapeutic target", Biochimica et Biophysica Acta 1762: 1051-1067 (2006).
Bauer et al., "Harnessing chaperone-mediated autophagy for the selective degradation of mutant huntingtin protein," Nature Biotech., 28(3): 256-263 (2010).
Benbrook et al., "Integration of Autophagy, Proteasomal Degradation, Unfolded Protein Response and Apoptosis," Exp. Oneal., 34(3): 286-297 (2012).
Bialik, S. and A. Kimchi, "The death-associated protein kinases: Structure, function, and beyond", Annual Review of Biochemistry 75: 189-210 (2006).
Bogoyevitch et al., "Peptide inhibitors of protein kinases—discovery, characterisation and use," Biochimica et Biophysica Acta, 1754: 79-99 (2005).
Bonger et al., "Small-molecule displacement of a cryptic degron causes conditional protein degradation," Nature Chemical Biology, 7: 531-537 (2011).
Brebner, "Nucleus Accumbens Long-Term Depression and the Expression of Behavioral Sensitization," Science, 310: 1340-1343 (2005).
Browne, S.E., et al., "Oxidative stress in Huntington's Disease", Brain Pathology 9: 147-163 (1999).
Carpenter-Hyland, E.P. and L.J. Chandler, "Homeostatic plasticity during alcohol exposure promotes enlargement of dendritic spines" European Journal of Neuroscience 24: 3496-3506 (2006).
Castanotto et al., "The promises and pitfalls of RNA-interference-based therapeutics," Nature, 457: 426-433 (2009).
Cataldo et al., "Enzymatically active lysosomal proteases are associated with amyloid deposits in Alzheimer brain," Proc. Natl. Acad. Sci. USA, 87: 3861-3865 (1990).
Chang et al., "27: Detection of Protein Kinase-Binding Partners by the Yeast Two-Hybrid Analysis,," from Methods in Molecular Biology, vol. 233: Protein Kinase C Protocols, Ed. A.C. New ton, Humana Press Inc., Totowa, NJ, pp. 327-343.
Cook, D.J., et al., "Treatment of stroke with a PSD-95 inhibitor in the gyrencephalic primate brain", Nature 483: 213-218 (2012).
Cohen et al., "OAP-kinase is a Ca2+/calmodulin-dependent, cytoskeletal-associated protein kinase, with cell death-inducing functions that depend on its catalytic activity," The EMBO Journal, 16:998-1008 (1997).
Cuervo et al., "Selective binding and uptake of ribonuclease A and glyceraldehyde-3-phosphate dehydrogenase by isolated rat liver lysosomes," J. Biol. Chem., 269: 26374-26380 (1994).
Cuervo et al., "Unique properties of Iamp2a compared to other Iamp2 isoforms," J. Cell. Sci., 113: 4441-4450 (2000).
Cuervo, "Impaired Degradation of Mutant a-Synuclein by Chaperone-Mediated Autophagy," Science, 305: 1292-1295 (2004).
Demarchi et al., "Activation of Transcription Factor NF-KB by the Tat Protein of Human Immunodeficiency Virus Type 1," J. Viral. 70: 4427-4437 (1996).
Dice, "Peptide sequences that target cytosolic proteins for lysosomal proteolysis," TIBS, 15: 305-309 (1990).
Dietz et al., "Delivery of bioactive molecules into the cell: the Trojan horse approach," Mol. Cell. Neurosci., 27: 85-131 (2004).
Eisenberg-Lerner et al., "DAP kinase regulates JNK signaling by binding and activating protein kinase D under oxidative stress," Cell Death Differ., 14: 1908-1915 (2007).
Fan et al., "Rapid and reversible knockdown of endogenous proteins by peptide-directed lysosomal degradation," Nature Neurosci., 17(3): 471-480 and online methods (2 pages) (2014).
Fischer 2001 "cellular delivery of Impermeable Effector Molecules in the Form of Conjugates with Peptides Capable of Mediating Membrane Translocation" Bioconjugate chemistry 12(6):825-841 (Year: 2001).
Gump, J.M., et al., "Revised role of glycosaminoglycans in TAT protein transduction domain-mediated cellular transduction", Journal of Biological Chemistry 285(2): 1500-1507 (2010).
Gilgun-Sherki et al., "Oxidative stress induced-neurodegenerative diseases: the need for antioxidants that penetrate the blood brain barrier," Neuropharmacology 40: 959-975 (2001).
Hannah et al., Maximizing target protein ablation by integration of RNAi and protein knockout, Cell Research, 21: 1152-1154 (2011).
Hainsworth, A.H., et al., "Death-associated protein kinase (DAPK1) in cerebral cortex of late-onset Alzheimer's diesase patients and aged controls" Neuropathology and Applied Neurobiology 36: 17-24 (2010).
Hamilton, R.L., "Lewy bodies in Alzheimer's disease: a neuropathological review of 145 cases using alpha-synuclein immunohistochemistry", Brain Pathology 10: 378-384 (2000).
Henchcliffe, C. and M.F. Beal, "Mitochondrial biology and oxidative stress in Parkinson disease pathology", Nature Clinical Practice Neurology 4(11): 600-609 (2008).
Hill et al., "Evaluating Neuroprotection in Aneurysm Coiling Therapy (ENACT) Final Results," International Stroke Conference, New Orleans, American Heart Association, 1 page (2012).
Jenssen, H. and S.I. Aspmo, "Serum Stability of Peptides", in Otvos, L. ed., Peptide-Based Drug Design.Methods in Molecular Biology, vol. 494 (Humana Press) at 177-186 (2008).
Jia, Z., et al., "Oxidative stress in spinal cord injury and antioxidant-based intervention", Spinal Cord 50: 264-274 (2012).
Kaplan, I.M., et al., "Cationic TAT peptide transduction domain enters cells by macropinocytosis", Journal of Controlled Release 102: 247-253 (2005).
Kaushik 2012 "Chaperone-mediated autophagy: a unique way to enter the lysosome world" trends cell biol 22(8):407-417 (Year: 2012).
Kim, B.G., et al., "Remodeling of synaptic structures in the motor cortex following spinal cord injury", Experimental Neurology 198: 401-415 (2006).
Knappe, D., et al., "Easy stratedy to protect antimicrobial pepties from fast degradation in serum", Antimicrobial Agents and Chemotheapy 54(9): 4003-4005 (2010).
Koga et al., "A photoconvertible fluorescent reporter to track chaperone-mediated autophagy," Nature Communications, 2: 386 (10 pages) (2011).
Li et al., "Chaperone-mediated autophagy: machinery, regulation and biological consequences," Cell. Mol. Life Sci., 68: 749-763 (2011).
Li, Y., et al., "DAPK1 variants are associated with Alzheimer's disease and allele-specific expression", Human Molecular Genetics 15(17):2560-2568 (2006).
Liang, T., et al., "a-Synuclein maps to a quantitative trait locus for alcohol preference and is differentially expressed in alcohol-preferring and -nonpreferring rats", PNAS 100(8): 4690-4695 (2003).
Lonn, P., et al., "Enhancing endosomal escape for intracellular delivery of macromolecular biologic therapeutics", Scientific Reports 6: 32301 (2016).
Majeski et al., "Mechanisms of chaperone-mediated autophagy," International J. Biochem. Cell Biol., 36: 2435-2444 (2004).
Martin et al., "Blocking the Deadly Effects of the NMDA Receptor in Stroke," Cell, 140: 174-176 (2010).
Martinez-Vincente, M. and E.Wong, "Chaperone-mediated autophagy and Parkinson's Disease" in Witt, S.N. ed., Protein Chaperones and Protection from Neurodegenerative Diseases (Hoboken, N.J.: John Wiley & Sons, Inc., pp. 101-138 (2011).
McGregor, D.P., "Discovering and improving novel peptide therapeutics", Current Opinion in Pharmacology 8: 616-619 (2008).
Milletti, "Cell-penetrating peptides: classes, origin, and current landscape," Drug Discovery Today, 17(15/16): 850-860 (2012).
Morris et al., "A peptide carrier for the delivery of biologically active proteins into mammalian cells," Nat. Biotech., 19: 1173-1176 (2001).
Nakase, I., et al., "Cellular uptake of arginine-rich peptides: Roles for macropinocytosis and actin rearrangement", Molecular Therapy 10(6): 1011-1022 (2004).

(56) References Cited

OTHER PUBLICATIONS

Neff et al., "Degradation of proteins microinjected into IMR-90 human diploid fibroblasts," Journal Cell Biol., 91, 184-194 (1981).
Neklesa et al., "Small-molecule hydrophobic tagging-induced degradation of HaloTag fusion proteins," Nature Chemical Biology, 7: 538-543 (2011).
Perez et al., "Antennapedia homeobox as a signal for the cellular internalization and nuclear addressing of a small exogenous peptide," J. Cell Sci., 102: 717-722 (1992).
Pooga et al., "Cell penetration by transportan," FASEB J 12: 67-77 (1998).
Popiel et al., "The aggregation inhibitor peptide QBP1 as a therapeutic molecule for the polyglutamine neurodegenerative diseases," J. Amino Acids, 2011: Article ID 265084, 10 pages (2011).
Rajendran et al., "Subcellular targeting strategies for drug design and delivery," Nature Reviews, 9: 29-42 (2010).
Recchia, A., et al., "a-Synuclein and Parkinson's disease", FASEB Journal 18(6): 617-626 (2016).
Ricart et al., "Hydrogen peroxide-induced neurotoxicity in cultured cortical cells grown in serum-free and serum-containing media," Neurochem. Res., 26: 801-808 (2001).
Sakurai, M., et al., "Induction of Parkinson disease-related proteins in motor neurons after transient spinal cord ischemia in rabbits", Journal of Cerebral Blood Flow and Metabolism 29: 752-758 (2009).
Sakamoto et al., "Protacs: chimeric molecules that target proteins to the Skp1-Cullin-F box complex for ubiquitination and degradation," PNAS, 98(15): 8554-8559 (2001).
Seglen et al., "Ammonia Inhibition of Protein Degradation in Isolated Rat Hepatocytes: Quantitative Ultrastructural Alterations in the Lysosomal System," Exp. Cell Res., 100:276-280 (1976).
Shaltiel-Karyo et al., "Inhibiting a-synuclein oligomerization by stable cell-penetrating-synuclein fragments recovers phenotype of Parkinson's Disease model flies," PLoS ONE, vol. 5(11): e13863, 13 pages (2010).
Shamloo et al., "Death-associated protein kinase is activated by dephosphorylation in response to cerebral ischemia," J. Biol. Chem., 280(51), 42290-42299 (2005).
Shaltiel-Karyo, et al., "Inhibiting a-Synuclein Oligomerization by Stable Cell-Penetrating—Synuclein Fragments Recovers Phenotype of Parkinson's Disease Model Files" PLoS ONE 5(11): e13863 (2010).
Shibasaki, M., et al., "Actin dynamics in development of behavioral sensitization after withdrawal from long-term ethanol administration to mice", Alcoholism: Clinical and Experimental Research 36(8): 1385-1396 (2012).
Slot et al., "Intracellular protein degradation in serum-deprived human fibroblasts," J. Biochem., 237: 491-498 (1986).
Spillantini et al., "a-Synuclein in Lewy bodies," Nature, 388: 839-840 (1997).
Stenmark et al., "Peptides Fused to the Amino-Terminal End of Diphtheria Toxin Are Trans located to the Cytosol," J. Cell. Biol., 113(5):1025-1032 (1991).
Svensen et al., "Peptides for cell-selective drug delivery," Trends Pharmacol. Sci., 33(4): 186-192 (2012).
Takei, Y., et al., "a-Synuclein coaggregation in familial amyotrophic lateral sclerosis with SOD1 gene mutation", Human Pathology 44: 1141-1176 (2013).
Taghibiglou et al., "Role of NMDA receptor-dependent activation of SREBP1 in excitotoxic and ischemic neuronal injuries," Nature Medicine, 15(12): 1399-1407 and online methods, 1 page (2009).
Terlecky et al., "Protein and Peptide Binding and Stimulation of in Vitro Lysosomal Proteolysis by the 73-kDa Heat Shock Cognate Protein," J. Biol. Chem., 267(13): 9202-9209 (1992).
Tomas-Zapico, C., et al., "a-Synuclein accumulates in huntingtin inclusions but forms independent filaments and its deficiency attenuates early phenotype in a mouse model of Huntington's disease", Human Molecular Genetics 21 (3): 495-510 (2012).
Traynelis et al. "Glutamate Receptor Ion Channels: Structure, Regulation, and Function," Pharmacol. Rev., 62(2): 405-496 (2010).
Tsai, G.E., et al., "Increased glutamatergic neurotransmission and oxidative stress after alcohol withdrawal", American Journal of Psychiatry 155(6): 726-732 (1998).
Tu et al., "DAPK1 interaction with NMDA receptor NR2B subunits mediates brain damage in stroke," Cell, 140: 222-234 (2010).
Unal-Cevik, I., et al., "Alpha-synuclein aggregation induced by brief ischemia negatively impacts neuronal survival in vivo: a study in [A30P]alpha-synuclein transgenic mouse", Journal of Cerebral Blood Flow & Metabolism 31: 913-923 (2011).
Uryu, K., et al., "Age-dependent synuclein pathology following traumatic brain injury in mice", Experimental Neurology 184: 214-224 (2003).
Vives et al. "A truncated HIV-1 Tat protein basic domain rapidly translocates through the plasma membrane and accumulates in the cell nucleus," J. Biol. Chem., 272(25): 16010-16017 (1997).
Vives, "Present and future of cell-penetrating peptide mediated delivery systems: 'Is the Trojan horse too wild to go only to Troy?'," J. Controlled Release, 109: 77-85 (2005).
Vives et al., "Cell-penetrating and cell-targeting peptides in drug delivery," Biochimica et Biophysica Acta, 1786: 126-138 (2008).
Wang et al., "a-Amino-3-hydroxy-5-methylisoxazole-4-propionic Acid Subtype Glutamate Receptor (AMPAR) Endocytosis Is Essential for N-Methyl-D-aspartate-induced Neuronal Apoptosis," J. Biol. Chem., 279(40): 41267-41270 (2004).
Wadia, J.S., et al., "Transducible TAT-HA fusogenic peptide enhances escape of TAT-fusion proteins after lipid raft macropinocytosis", Nature Medicine 10(3): 310-315 (2004).
Werner, C. and K. Engelhard, "Pathophysiology of traumatic brain injury", British Journal of Anaesthesia 99(1): 4-9 (2007).
Wie;Dtocha et al., "Dual Mode of Signal Transduction by Externally Added Acidic Firbroblast Grwoth Factor," Cell, 76: 1039-1051 (1994).
Yang, Y. et al., "HIV-1 TAT-mediated protein transduction and subcellular localization using novel expression vectors", FEBS Letters 532:36-44 (2002).
Ziolkowska, B., et al., "a-Synuclein expression in the brain and blood during abstinence from chronic alcohol drinking in mice", Neuropharmacology 54(8): 1239-1246 (2008).
Communication of the extended European Search Report, for European Patent App. No. 13841990.8, dated Mar. 18, 2016 (12 pages).
International Search Report and Written Opinion for WIPO Application No. PCT/CA2013/050741, dated Jan. 2, 2014 (12 pages).

* cited by examiner

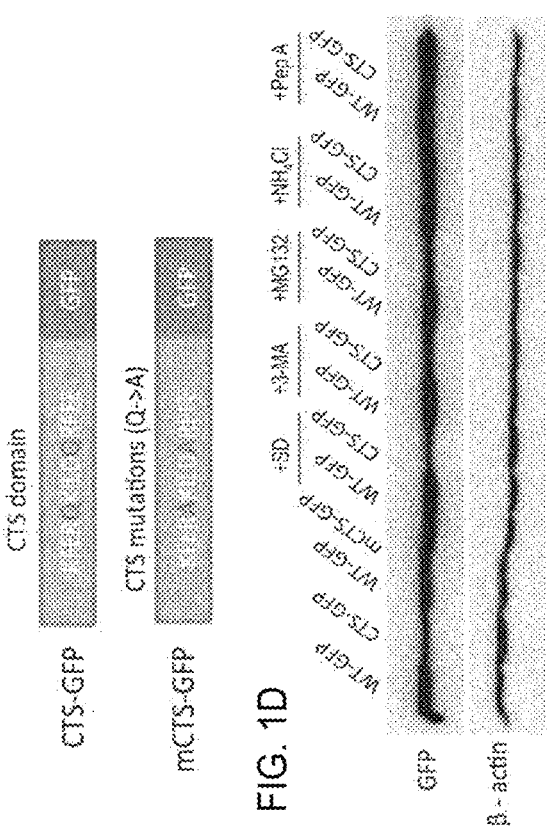
FIG. 1A
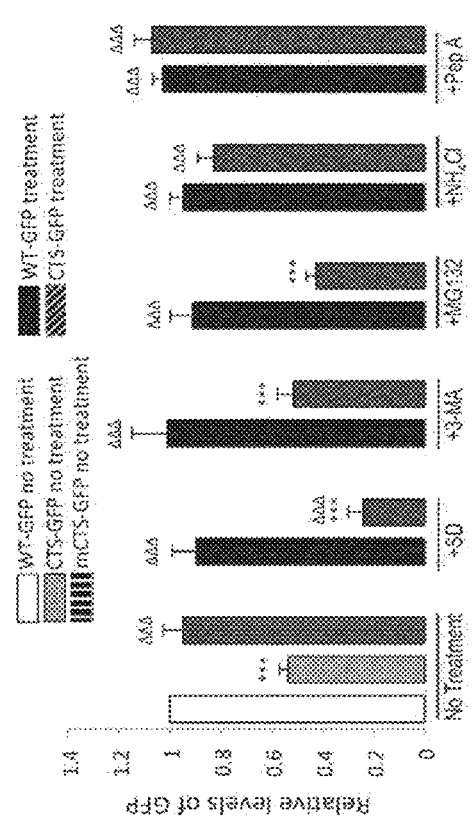
FIG. 1B
FIG. 1D
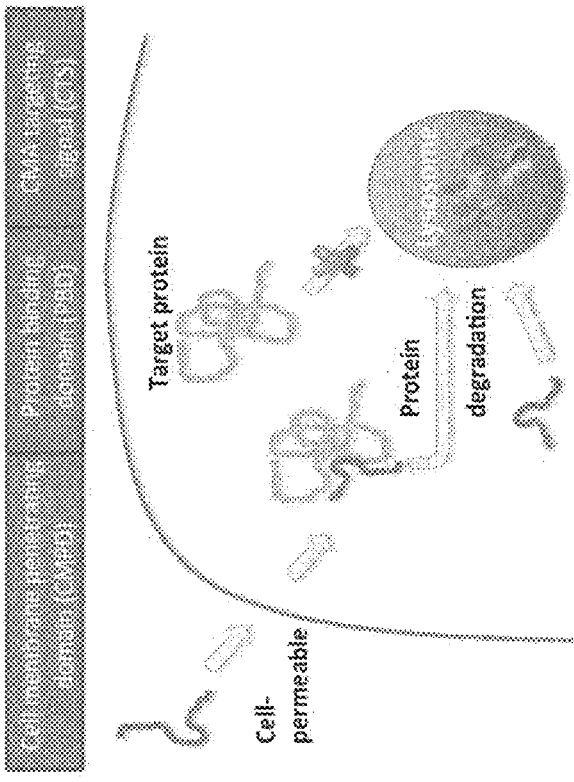
FIG. 1C
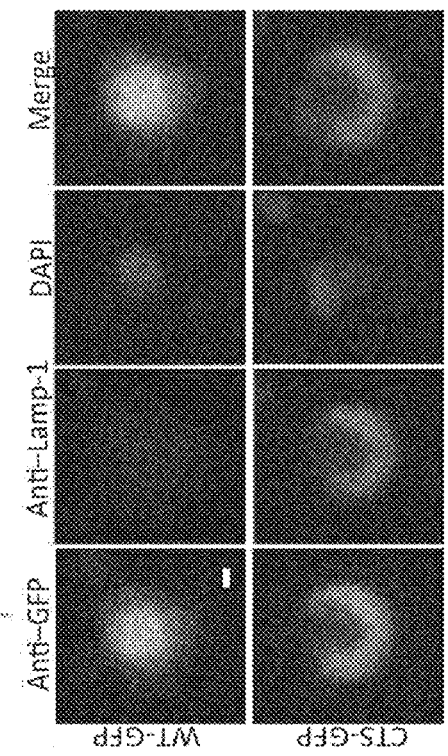

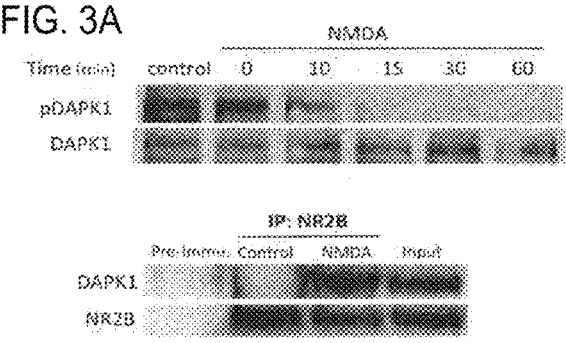
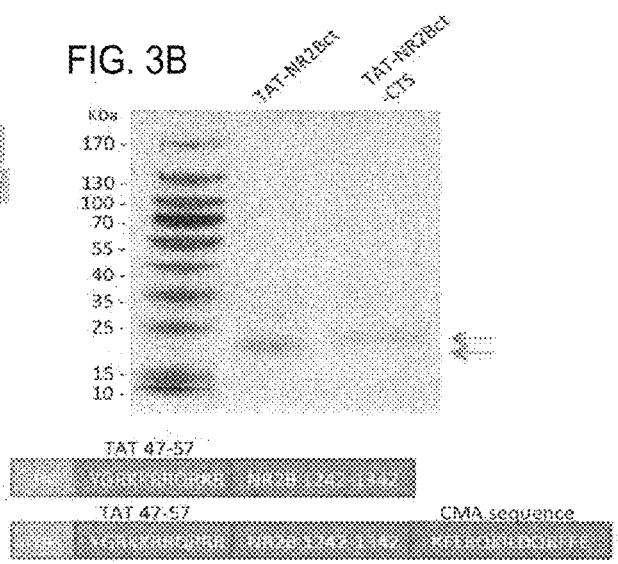
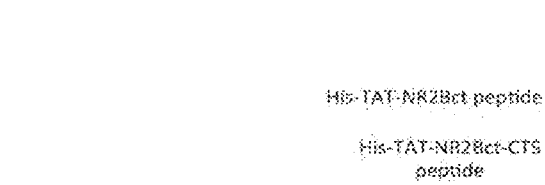
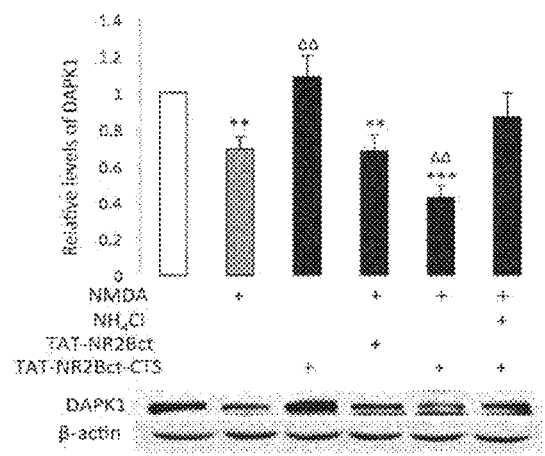
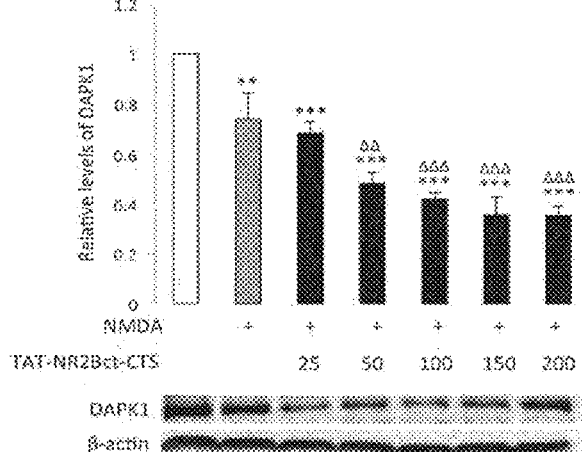
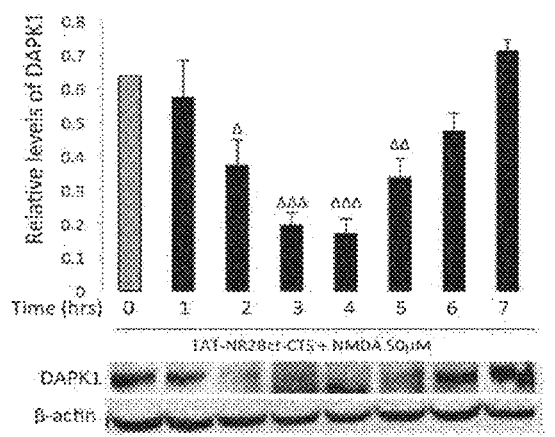
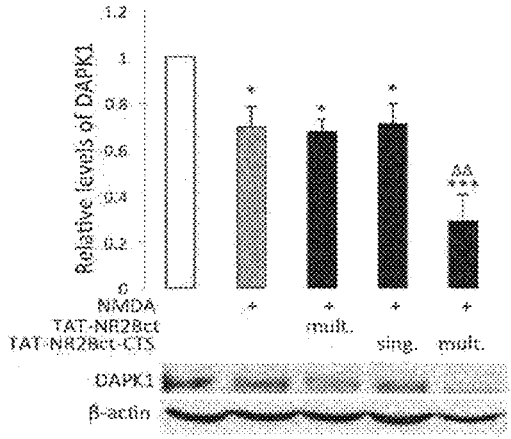
FIG. 3A  FIG. 3B  FIG. 3C  FIG. 3D  FIG. 3E  FIG. 3F

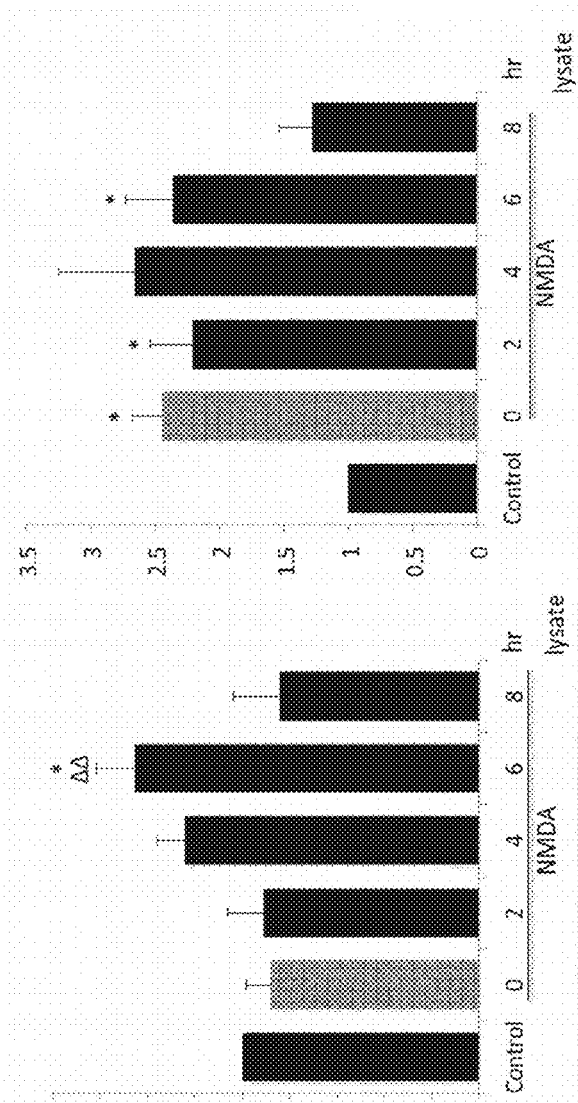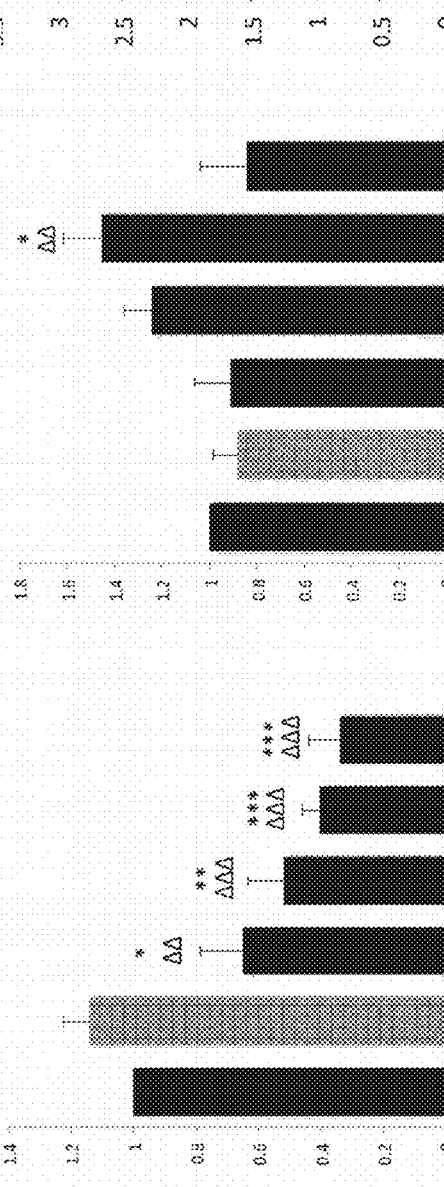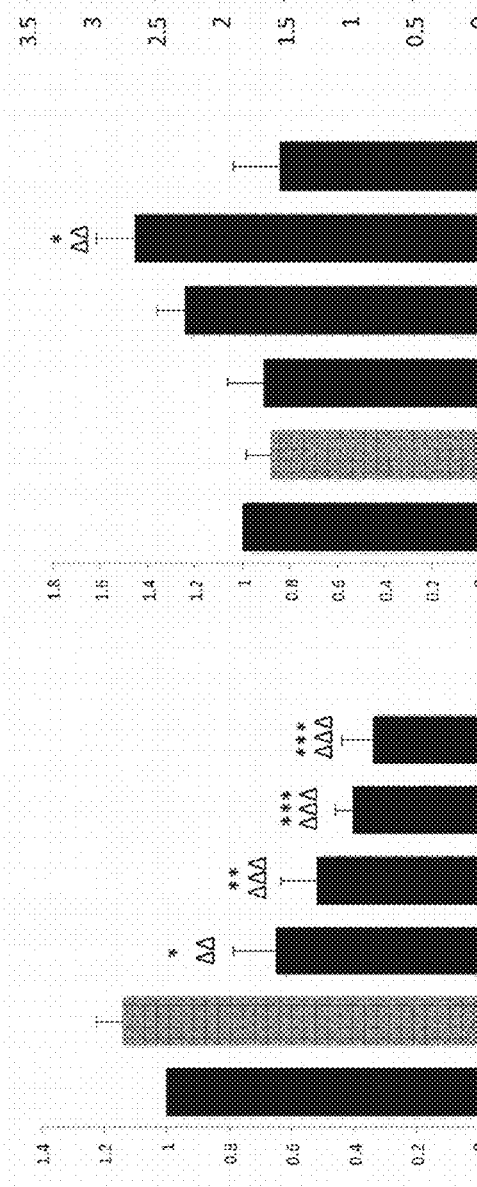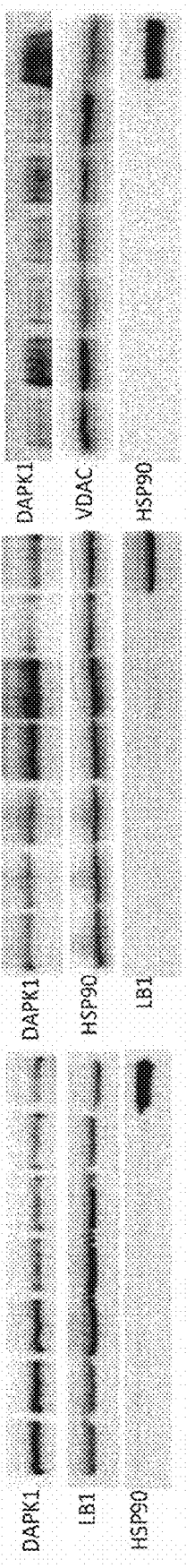
FIG. 7A  FIG. 7B  FIG. 7C

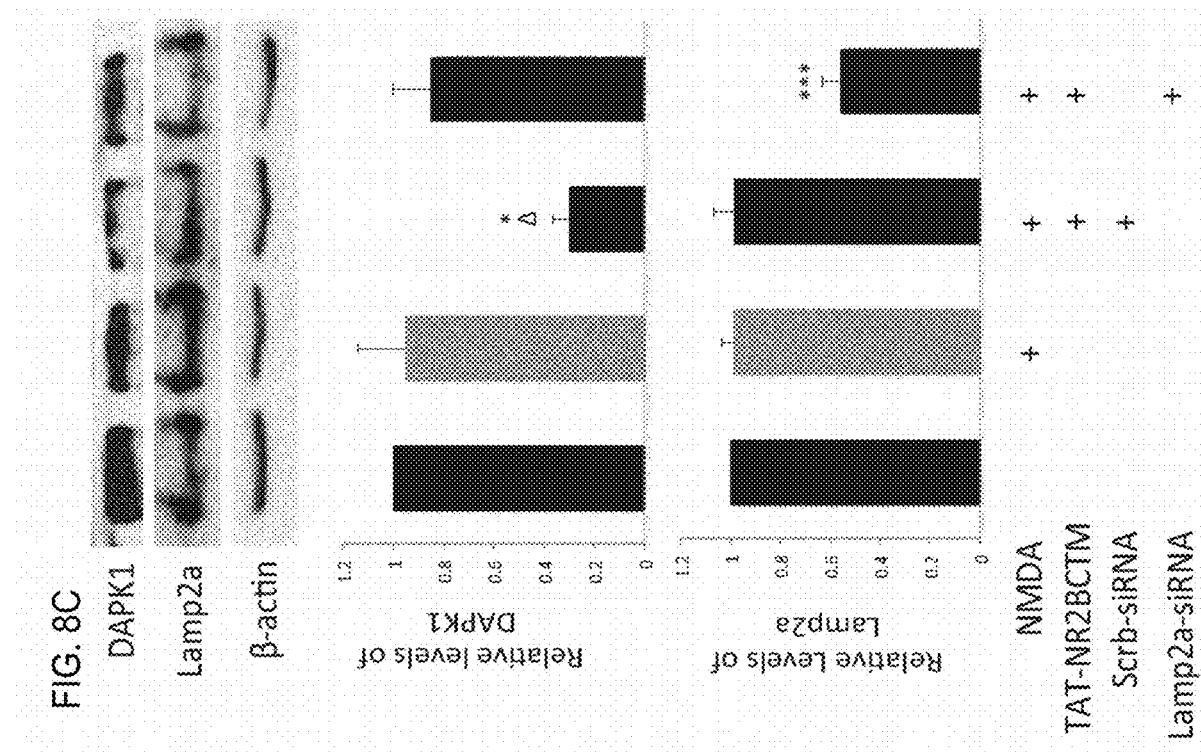
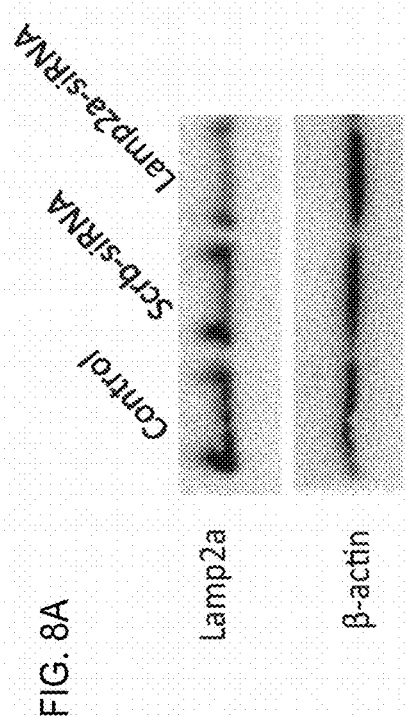
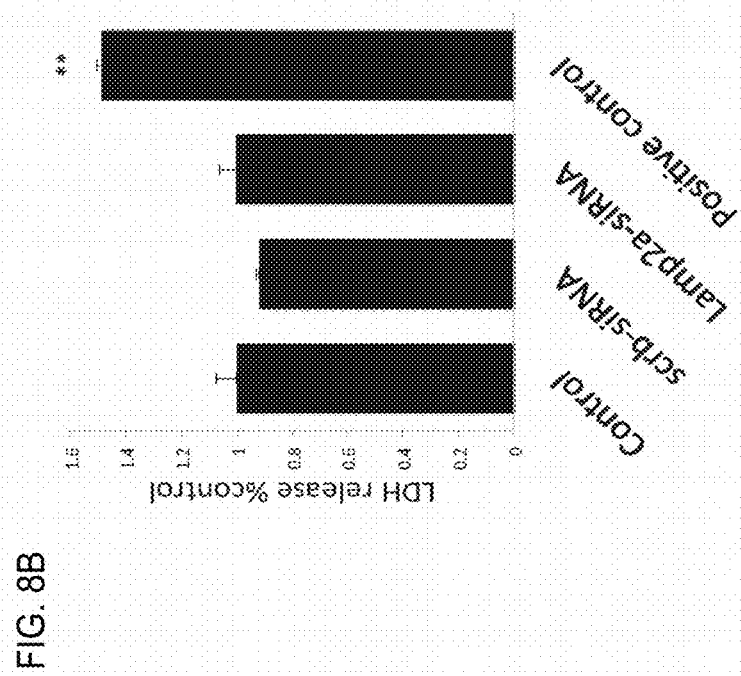

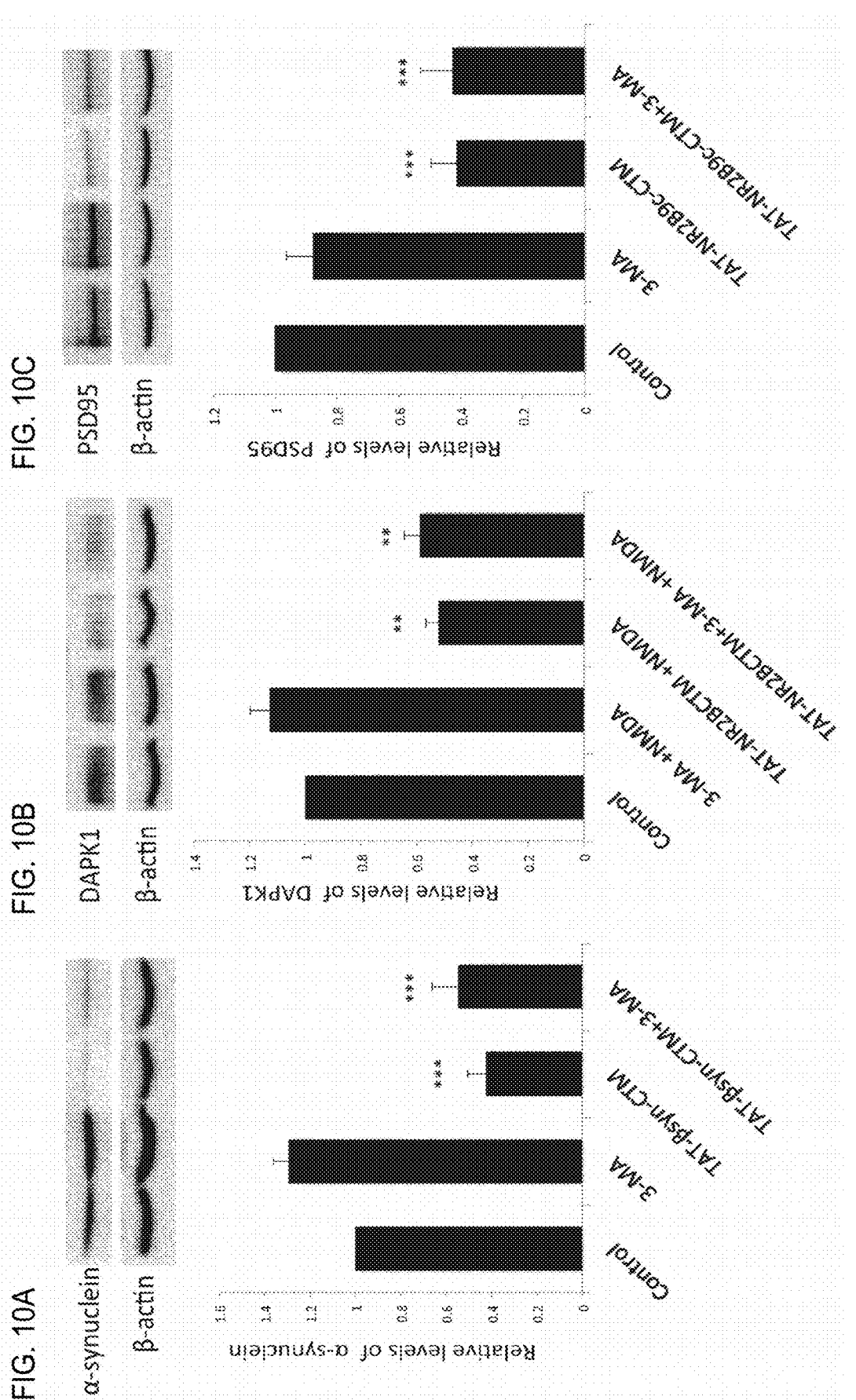

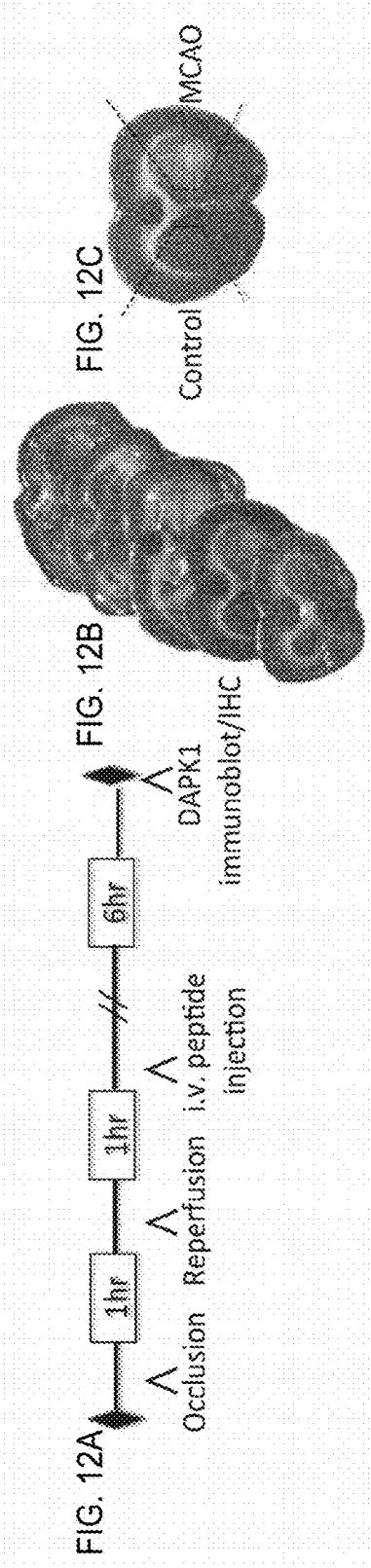
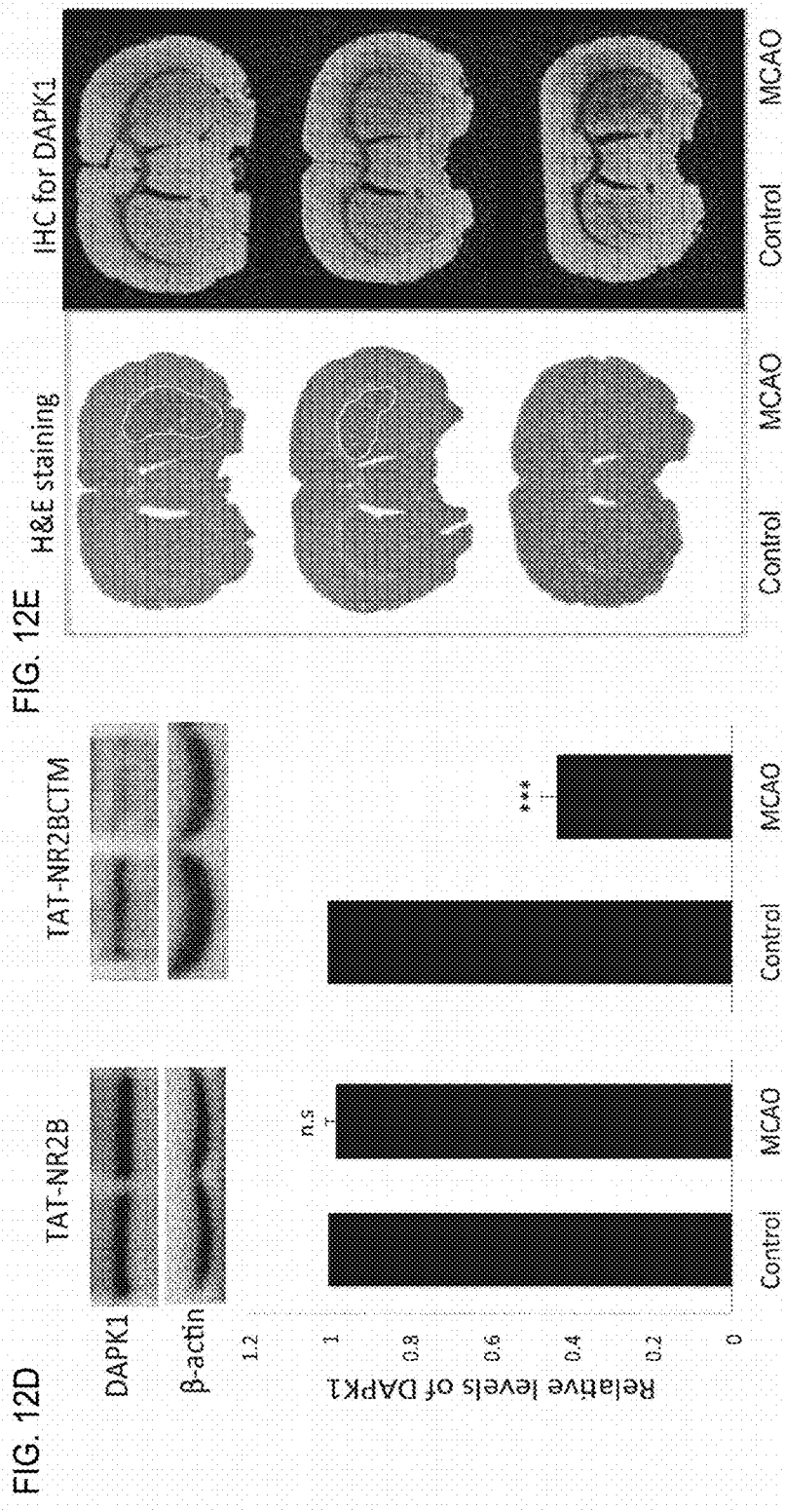

```
                        SEQUENCE LISTING

<160> NUMBER OF SEQ ID NOS: 61

<210> SEQ ID NO 1
<211> LENGTH: 24
<212> TYPE: PRT
<213> ORGANISM: Artificial sequence
<220> FEATURE:
<223> OTHER INFORMATION: Knockdown peptide targeting alpha-synuclein
      without TAT protein transduction domain

<400> SEQUENCE: 1

Gly Val Leu Tyr Val Gly Ser Lys Thr Arg Lys Phe Glu Arg Gln Lys
1               5                   10                  15

Ile Leu Asp Gln Arg Phe Phe Glu
            20

<210> SEQ ID NO 2
<211> LENGTH: 35
<212> TYPE: PRT
<213> ORGANISM: Artificial sequence
<220> FEATURE:
<223> OTHER INFORMATION: Knockdown peptide targeting alpha-synuclein,
      with TAT protein transduction domain

<400> SEQUENCE: 2

Tyr Gly Arg Lys Lys Arg Arg Gln Arg Arg Gly Val Leu Tyr Val
1               5                   10                  15

Gly Ser Lys Thr Arg Lys Phe Glu Arg Gln Lys Ile Leu Asp Gln Arg
            20                  25                  30

Phe Phe Glu
        35

<210> SEQ ID NO 3
<211> LENGTH: 27
<212> TYPE: PRT
<213> ORGANISM: Artificial sequence
<220> FEATURE:
<223> OTHER INFORMATION: Knockdown peptide targeting DAPK1, without TAT
      protein transduction domain

<400> SEQUENCE: 3

Lys Lys Asn Arg Asn Lys Leu Arg Arg Gln His Ser Tyr Lys Phe Glu
1               5                   10                  15

Arg Gln Lys Ile Leu Asp Gln Arg Phe Phe Glu
            20                  25
```

<210> SEQ ID NO 4
<211> LENGTH: 38
<212> TYPE: PRT
<213> ORGANISM: Artificial sequence
<220> FEATURE:
<223> OTHER INFORMATION: Knockdown peptide targeting DAPK1, with TAT
      protein transduction domain

<400> SEQUENCE: 4

Tyr Gly Arg Lys Lys Arg Arg Gln Arg Arg Lys Lys Asn Arg Asn
1               5                   10                  15

Lys Leu Arg Arg Gln His Ser Tyr Lys Phe Glu Arg Gln Lys Ile Leu
            20                  25                  30

Asp Gln Arg Phe Phe Glu
        35

<210> SEQ ID NO 5
<211> LENGTH: 13
<212> TYPE: PRT
<213> ORGANISM: Human influenza virus

<400> SEQUENCE: 5

Gly Arg Lys Lys Arg Arg Gln Arg Arg Arg Pro Pro Gln
1               5                   10

<210> SEQ ID NO 6
<211> LENGTH: 15
<212> TYPE: PRT
<213> ORGANISM: Drosophila melanogaster

<400> SEQUENCE: 6

Arg Gln Ile Lys Trp Phe Gln Asn Arg Arg Met Lys Trp Lys Lys
1               5                   10                  15

<210> SEQ ID NO 7
<211> LENGTH: 21
<212> TYPE: PRT
<213> ORGANISM: Unknown
<220> FEATURE:
<223> OTHER INFORMATION: Buforin II cell-membrane penetrating domain

<400> SEQUENCE: 7

Thr Arg Ser Ser Arg Ala Gly Leu Gln Phe Pro Val Gly Arg Val His
1               5                   10                  15

Arg Leu Leu Arg Lys
            20

<210> SEQ ID NO 8
<211> LENGTH: 13
<212> TYPE: PRT
<213> ORGANISM: Homo sapiens

<400> SEQUENCE: 8

Lys Arg Val Ser Arg Asn Lys Ser Glu Lys Lys Arg Arg
1               5                   10

<210> SEQ ID NO 9
<211> LENGTH: 18
<212> TYPE: PRT
<213> ORGANISM: Unknown
<220> FEATURE:
<223> OTHER INFORMATION: Model amphipathic peptide cell-membrane
      penetrating domain

<400> SEQUENCE: 9

```
Lys Leu Ala Leu Lys Leu Ala Leu Lys Ala Leu Lys Ala Ala Leu Lys
1               5                   10                  15
Leu Ala

<210> SEQ ID NO 10
<211> LENGTH: 16
<212> TYPE: PRT
<213> ORGANISM: Unknown
<220> FEATURE:
<223> OTHER INFORMATION: K-FGF cell-membrane penetrating domain

<400> SEQUENCE: 10

Ala Ala Val Ala Leu Leu Pro Ala Val Leu Leu Ala Leu Leu Ala Pro
1               5                   10                  15

<210> SEQ ID NO 11
<211> LENGTH: 6
<212> TYPE: PRT
<213> ORGANISM: Unknown
<220> FEATURE:
<223> OTHER INFORMATION: Ku70-derived peptide cell-membrane penetrating
      domain

<400> SEQUENCE: 11

Val Pro Met Leu Lys Glu
1               5

<210> SEQ ID NO 12
<211> LENGTH: 5
<212> TYPE: PRT
<213> ORGANISM: Unknown
<220> FEATURE:
<223> OTHER INFORMATION: Ku70-derived peptide cell-membrane penetrating
      domain

<400> SEQUENCE: 12

Val Pro Met Leu Lys
1               5

<210> SEQ ID NO 13
<211> LENGTH: 5
<212> TYPE: PRT
<213> ORGANISM: Unknown
<220> FEATURE:
<223> OTHER INFORMATION: Ku70-derived peptide cell-membrane penetrating
      domain

<400> SEQUENCE: 13

Pro Met Leu Lys Glu
1               5

<210> SEQ ID NO 14
<211> LENGTH: 4
<212> TYPE: PRT
<213> ORGANISM: Unknown
<220> FEATURE:
<223> OTHER INFORMATION: Ku70-derived peptide cell-membrane penetrating
      domain

<400> SEQUENCE: 14

Pro Met Leu Lys
1

<210> SEQ ID NO 15
<211> LENGTH: 28
<212> TYPE: PRT
<213> ORGANISM: Unknown
```

```
<220> FEATURE:
<223> OTHER INFORMATION: Prion, Mouse Prpe cell-membrane penetrating
      domain

<400> SEQUENCE: 15

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 16
<211> LENGTH: 18
<212> TYPE: PRT
<213> ORGANISM: Unknown
<220> FEATURE:
<223> OTHER INFORMATION: pVEC cell-membrane penetrating domain

<400> SEQUENCE: 16

Leu Leu Ile Ile Leu Arg Arg Arg Ile Arg Lys Gln Ala His Ala His
1               5                   10                  15

Ser Lys

<210> SEQ ID NO 17
<211> LENGTH: 21
<212> TYPE: PRT
<213> ORGANISM: Unknown
<220> FEATURE:
<223> OTHER INFORMATION: Pep-I cell-membrane penetrating domain

<400> SEQUENCE: 17

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 18
<211> LENGTH: 18
<212> TYPE: PRT
<213> ORGANISM: Unknown
<220> FEATURE:
<223> OTHER INFORMATION: SynB1 cell-membrane penetrating domain

<400> SEQUENCE: 18

Arg Gly Gly Arg Leu Ser Tyr Ser Arg Arg Arg Phe Ser Thr Ser Thr
1               5                   10                  15

Gly Arg

<210> SEQ ID NO 19
<211> LENGTH: 27
<212> TYPE: PRT
<213> ORGANISM: Unknown
<220> FEATURE:
<223> OTHER INFORMATION: Transportan cell-membrane penetrating domain

<400> SEQUENCE: 19

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 20
<211> LENGTH: 21
<212> TYPE: PRT
<213> ORGANISM: Unknown
```

-continued

```
<220> FEATURE:
<223> OTHER INFORMATION: Transportan-10 cell-membrane penetrating domain

<400> SEQUENCE: 20

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 21
<211> LENGTH: 20
<212> TYPE: PRT
<213> ORGANISM: Unknown
<220> FEATURE:
<223> OTHER INFORMATION: CADY cell-membrane penetrating domain

<400> SEQUENCE: 21

Gly Leu Trp Arg Ala Leu Trp Arg Leu Leu Arg Ser Leu Trp Arg Leu
1               5                   10                  15

Leu Trp Arg Ala
            20

<210> SEQ ID NO 22
<211> LENGTH: 15
<212> TYPE: PRT
<213> ORGANISM: Unknown
<220> FEATURE:
<223> OTHER INFORMATION: Pep-7 cell-membrane penetrating domain

<400> SEQUENCE: 22

Ser Asp Leu Trp Glu Met Met Met Val Ser Leu Ala Cys Gln Tyr
1               5                   10                  15

<210> SEQ ID NO 23
<211> LENGTH: 12
<212> TYPE: PRT
<213> ORGANISM: Unknown
<220> FEATURE:
<223> OTHER INFORMATION: HN-1 cell-membrane penetrating domain

<400> SEQUENCE: 23

Thr Ser Pro Leu Asn Ile His Asn Gly Gln Lys Leu
1               5                   10

<210> SEQ ID NO 24
<211> LENGTH: 26
<212> TYPE: PRT
<213> ORGANISM: Unknown
<220> FEATURE:
<223> OTHER INFORMATION: VT5 cell-membrane penetrating domain

<400> SEQUENCE: 24

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 25
<211> LENGTH: 16
<212> TYPE: PRT
<213> ORGANISM: Unknown
<220> FEATURE:
<223> OTHER INFORMATION: pISL cell-membrane penetrating domain

<400> SEQUENCE: 25
```

-continued

Arg Val Ile Arg Val Trp Phe Gln Asn Lys Arg Cys Lys Asp Lys Lys
1               5                   10                  15

<210> SEQ ID NO 26
<211> LENGTH: 5
<212> TYPE: PRT
<213> ORGANISM: Unknown
<220> FEATURE:
<223> OTHER INFORMATION: Chaperone-mediated autophagy targeting signal,
      pentapeptide motif

<400> SEQUENCE: 26

Lys Phe Glu Arg Gln
1               5

<210> SEQ ID NO 27
<211> LENGTH: 12
<212> TYPE: PRT
<213> ORGANISM: Unknown
<220> FEATURE:
<223> OTHER INFORMATION: AHNP homing peptide conjugated to
      cell-penetrating peptide

<400> SEQUENCE: 27

Phe Cys Asp Gly Phe Tyr Ala Cys Tyr Lys Asp Val
1               5                   10

<210> SEQ ID NO 28
<211> LENGTH: 21
<212> TYPE: PRT
<213> ORGANISM: Unknown
<220> FEATURE:
<223> OTHER INFORMATION: DV1 homing peptide conjugated to
      cell-penetrating peptide

<400> SEQUENCE: 28

Leu Gly Ala Ser Trp His Arg Pro Asp Lys Cys Cys Leu Gly Tyr Gln
1               5                   10                  15

Lys Arg Pro Leu Pro
            20

<210> SEQ ID NO 29
<211> LENGTH: 10
<212> TYPE: PRT
<213> ORGANISM: Unknown
<220> FEATURE:
<223> OTHER INFORMATION: DV3 homing peptide conjugated to
      cell-penetrating peptide

<400> SEQUENCE: 29

Leu Gly Ala Ser Trp His Arg Pro Asp Lys
1               5                   10

<210> SEQ ID NO 30
<211> LENGTH: 9
<212> TYPE: PRT
<213> ORGANISM: Unknown
<220> FEATURE:
<223> OTHER INFORMATION: PEGA homing peptide conjugated to
      cell-penetrating peptide

<400> SEQUENCE: 30

Cys Pro Gly Pro Glu Gly Ala Gly Cys
1               5

<210> SEQ ID NO 31
<211> LENGTH: 5

```
<212> TYPE: PRT
<213> ORGANISM: Unknown
<220> FEATURE:
<223> OTHER INFORMATION: CREKA homing peptide conjugated to
      cell-penetrating peptide

<400> SEQUENCE: 31

Cys Arg Glu Lys Ala
1               5

<210> SEQ ID NO 32
<211> LENGTH: 9
<212> TYPE: PRT
<213> ORGANISM: Unknown
<220> FEATURE:
<223> OTHER INFORMATION: TCP-1 cell-penetrating homing peptide

<400> SEQUENCE: 32

Cys Thr Pro Ser Pro Phe Ser His Cys
1               5

<210> SEQ ID NO 33
<211> LENGTH: 12
<212> TYPE: PRT
<213> ORGANISM: Unknown
<220> FEATURE:
<223> OTHER INFORMATION: HAP-1 cell-penetrating homing peptide

<400> SEQUENCE: 33

Ser Phe His Gln Phe Ala Arg Ala Thr Leu Ala Ser
1               5                   10

<210> SEQ ID NO 34
<211> LENGTH: 11
<212> TYPE: PRT
<213> ORGANISM: Unknown
<220> FEATURE:
<223> OTHER INFORMATION: HAP-2 cell-penetrating homing peptide

<400> SEQUENCE: 34

His Ile Gln Leu Ser Pro Phe Gln Ser Trp Arg
1               5                   10

<210> SEQ ID NO 35
<211> LENGTH: 4
<212> TYPE: PRT
<213> ORGANISM: Unknown
<220> FEATURE:
<223> OTHER INFORMATION: Cell-penetrating homing peptide

<400> SEQUENCE: 35

Pro Tyr Glu Glu
1

<210> SEQ ID NO 36
<211> LENGTH: 4
<212> TYPE: PRT
<213> ORGANISM: Unknown
<220> FEATURE:
<223> OTHER INFORMATION: Cell-penetrating homing peptide

<400> SEQUENCE: 36

Leu Lys Lys Pro
1

<210> SEQ ID NO 37
<211> LENGTH: 4
```

<212> TYPE: PRT
<213> ORGANISM: Unknown
<220> FEATURE:
<223> OTHER INFORMATION: Cell-penetrating homing peptide
<220> FEATURE:
<221> NAME/KEY: MISC_FEATURE
<222> LOCATION: (4)..(4)
<223> OTHER INFORMATION: N-alkyl glycine lysine-like peptoid

<400> SEQUENCE: 37

Glu Pro Lys Xaa
1

<210> SEQ ID NO 38
<211> LENGTH: 4
<212> TYPE: PRT
<213> ORGANISM: Unknown
<220> FEATURE:
<223> OTHER INFORMATION: Cell-penetrating homing peptide
<220> FEATURE:
<221> NAME/KEY: MISC_FEATURE
<222> LOCATION: (3)..(4)
<223> OTHER INFORMATION: N-alkyl glycine lysine-like peptoid

<400> SEQUENCE: 38

Glu Leu Xaa Xaa
1

<210> SEQ ID NO 39
<211> LENGTH: 32
<212> TYPE: PRT
<213> ORGANISM: Unknown
<220> FEATURE:
<223> OTHER INFORMATION: F3 cell-penetrating homing peptide

<400> SEQUENCE: 39

Cys Lys Asp Glu Pro Gln Arg Arg Ser Ala Arg Leu Ser Ala Lys Pro
1               5                   10                  15

Ala Pro Pro Lys Pro Glu Pro Lys Pro Lys Lys Ala Pro Ala Lys Lys
            20                  25                  30

<210> SEQ ID NO 40
<211> LENGTH: 13
<212> TYPE: PRT
<213> ORGANISM: Unknown
<220> FEATURE:
<223> OTHER INFORMATION: Pep42 cell-penetrating homing peptide

<400> SEQUENCE: 40

Cys Thr Val Ala Leu Pro Gly Gly Tyr Val Arg Val Cys
1               5                   10

<210> SEQ ID NO 41
<211> LENGTH: 12
<212> TYPE: PRT
<213> ORGANISM: Unknown
<220> FEATURE:
<223> OTHER INFORMATION: CAP cell-penetrating homing peptide

<400> SEQUENCE: 41

Asp Trp Arg Val Ile Ile Pro Pro Arg Pro Ser Ala
1               5                   10

<210> SEQ ID NO 42
<211> LENGTH: 9
<212> TYPE: PRT
<213> ORGANISM: Unknown
<220> FEATURE:

<223> OTHER INFORMATION: RGD-4C cell-penetrating homing peptide

<400> SEQUENCE: 42

Cys Asp Cys Arg Gly Asp Cys Phe Cys
1               5

<210> SEQ ID NO 43
<211> LENGTH: 9
<212> TYPE: PRT
<213> ORGANISM: Unknown
<220> FEATURE:
<223> OTHER INFORMATION: iRGD cell-penetrating homing peptide

<400> SEQUENCE: 43

Cys Arg Gly Asp Lys Gly Pro Asp Cys
1               5

<210> SEQ ID NO 44
<211> LENGTH: 9
<212> TYPE: PRT
<213> ORGANISM: Unknown
<220> FEATURE:
<223> OTHER INFORMATION: iRGD cell-penetrating homing peptide

<400> SEQUENCE: 44

Cys Arg Gly Asp Arg Gly Pro Asp Cys
1               5

<210> SEQ ID NO 45
<211> LENGTH: 9
<212> TYPE: PRT
<213> ORGANISM: Unknown
<220> FEATURE:
<223> OTHER INFORMATION: iRGD cell-penetrating homing peptide

<400> SEQUENCE: 45

Cys Arg Gly Asp Lys Gly Pro Glu Cys
1               5

<210> SEQ ID NO 46
<211> LENGTH: 9
<212> TYPE: PRT
<213> ORGANISM: Unknown
<220> FEATURE:
<223> OTHER INFORMATION: iRGD cell-penetrating homing peptide

<400> SEQUENCE: 46

Cys Arg Gly Asp Arg Gly Pro Glu Cys
1               5

<210> SEQ ID NO 47
<211> LENGTH: 5
<212> TYPE: PRT
<213> ORGANISM: Unknown
<220> FEATURE:
<223> OTHER INFORMATION: Chaperone-mediated autophagy targeting signal
      identified from Rnase A

<400> SEQUENCE: 47

Lys Phe Glu Arg Gln
1               5

<210> SEQ ID NO 48
<211> LENGTH: 5
<212> TYPE: PRT
<213> ORGANISM: Unknown
<220> FEATURE:

```
<223> OTHER INFORMATION: Chaperone-mediated autophagy targeting signal
      identified from hsc70

<400> SEQUENCE: 48

Gln Lys Ile Leu Asp
1               5

<210> SEQ ID NO 49
<211> LENGTH: 5
<212> TYPE: PRT
<213> ORGANISM: Unknown
<220> FEATURE:
<223> OTHER INFORMATION: Chaperone-mediated autophagy targeting signal
      identified from Hemoglobin

<400> SEQUENCE: 49

Gln Arg Phe Phe Glu
1               5

<210> SEQ ID NO 50
<211> LENGTH: 5
<212> TYPE: PRT
<213> ORGANISM: Unknown
<220> FEATURE:
<223> OTHER INFORMATION: cRGDF cell-penetrating homing peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 50

Arg Gly Asp Phe Xaa
1               5

<210> SEQ ID NO 51
<211> LENGTH: 9
<212> TYPE: PRT
<213> ORGANISM: Unknown
<220> FEATURE:
<223> OTHER INFORMATION: NR2B subunit of N-methyl-D-aspartate receptor

<400> SEQUENCE: 51

Lys Leu Ser Ser Ile Glu Ser Asp Val
1               5

<210> SEQ ID NO 52
<211> LENGTH: 34
<212> TYPE: PRT
<213> ORGANISM: Artificial Sequence
<220> FEATURE:
<223> OTHER INFORMATION: targeted knockdown peptide targeting PSD95,
      with TAT PTD

<400> SEQUENCE: 52

Tyr Gly Arg Lys Lys Arg Arg Gln Arg Arg Lys Leu Ser Ser Ile
1               5                   10                  15

Glu Ser Asp Val Lys Phe Glu Arg Gln Lys Ile Leu Asp Gln Arg Phe
            20                  25                  30

Phe Glu

<210> SEQ ID NO 53
<211> LENGTH: 14
<212> TYPE: PRT
<213> ORGANISM: Artificial Sequence
<220> FEATURE:
<223> OTHER INFORMATION: Synthetic Construct
```

```
<400> SEQUENCE: 53

Lys Phe Glu Arg Gln Lys Ile Leu Asp Gln Arg Phe Phe Glu
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Synthetic Construct

<400> SEQUENCE: 54

Lys Phe Glu Arg Ala Lys Ile Leu Asp Ala Arg Phe Phe Glu
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic Construct

<400> SEQUENCE: 55

Gly Val Leu Tyr Val Gly Ser Lys Thr Arg
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Synthetic Construct

<400> SEQUENCE: 56

Tyr Pro Tyr Asp Val Pro Asp Tyr Ala
1               5

<210> SEQ ID NO 57
<211> LENGTH: 11
<212> TYPE: PRT
<213> ORGANISM: Artificial Sequence
<220> FEATURE:
<223> OTHER INFORMATION: Synthetic Construct

<400> SEQUENCE: 57

Tyr Gly Arg Lys Lys Arg Arg Gln Arg Arg Arg
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Synthetic Construct

<400> SEQUENCE: 58

Lys Lys Asn Arg Asn Lys Leu Arg Arg Gln His Ser Tyr
1               5                   10

<210> SEQ ID NO 59
<211> LENGTH: 24
<212> TYPE: PRT
<213> ORGANISM: Artificial Sequence
<220> FEATURE:
<223> OTHER INFORMATION: Synthetic Construct

<400> SEQUENCE: 59
```

```
Tyr Gly Arg Lys Lys Arg Arg Gln Arg Arg Lys Lys Asn Arg Asn
1               5                   10                  15

Lys Leu Arg Arg Gln His Ser Tyr
            20

<210> SEQ ID NO 60
<211> LENGTH: 21
<212> TYPE: PRT
<213> ORGANISM: Artificial Sequence
<220> FEATURE:
<223> OTHER INFORMATION: Synthetic Construct

<400> SEQUENCE: 60

Tyr Gly Arg Lys Lys Arg Arg Gln Arg Arg Gly Val Leu Tyr Val
1               5                   10                  15

Gly Ser Lys Thr Arg
            20

<210> SEQ ID NO 61
<211> LENGTH: 20
<212> TYPE: PRT
<213> ORGANISM: Artificial Sequence
<220> FEATURE:
<223> OTHER INFORMATION: Synthetic Construct

<400> SEQUENCE: 61

Tyr Gly Arg Lys Lys Arg Arg Gln Arg Arg Lys Leu Ser Ser Ile
1               5                   10                  15

Glu Ser Asp Val
            20
```

PEPTIDE DIRECTED PROTEIN KNOCKDOWN

The present application is a continuation of U.S. patent application Ser. No. 14/431,060, filed Aug. 17, 2015, which claims the benefit under 35 U.S.C. § 119(e) of U.S. provisional patent application Ser. No. 61/706,506, filed Sep. 27, 2012, the contents of which are hereby incorporated by reference.

FIELD OF THE INVENTION

The invention is in the field of molecular cell biology, involving recombinant nucleic acid and protein constructs that may be used to modulate the expression of proteins in cells. In particular, aspects of the invention relate to peptide mediated knockdown of endogenous cellular proteins using constructs that direct targeting proteins to the lysosome for degradation.

BACKGROUND

Rapid and reversible methods for altering the expression level of endogenous proteins are not only indispensable tools for studying complex biological systems, but may potentially drive the development of new therapeutics for the treatment of many diseases. Techniques that manipulate protein expression and function by targeting DNA or mRNA have proven to be powerful tools, but are often plagued by problems such as lack of specificity, speed, reversibility and tunability[1]. Furthermore, their therapeutic use in treating human diseases may be stymied by the lack of an efficient systemic delivery system[2].

To overcome shortcomings of DNA- and mRNA-based protein manipulations[2], attempts have been made to harness cellular protein degradation systems to reduce levels of proteins-of-interest[3-6]. Many of these proposed systems require genetic manipulation of the proteins to facilitate their targeting and degradation via specific cellular protein degradation systems[1].

Cell membrane penetrating domains (CMPDs) (also referred to as cell-penetrating peptides (CPPs) or protein transduction domains (PTDs)) are protein domains that mediate translocation across cellular membranes, such as the Tat protein from the HIV-1 virus and the *Drosophila melanogaster* Antennapedia homeodomain[38,39,40].

SUMMARY OF THE INVENTION

In one aspect, the present invention relates to peptide-based systems that can produce rapid and reversible knockdown of non-genetically modified native proteins by utilizing the endogenous lysosome-dependent autophagy system, chaperone-mediated autophagy (CMA) (FIG. 1a). CMA is a type of autophagy resulting in the selective uptake of substrate proteins in a molecule-by-molecule basis. This specificity is realized by a CMA-targeting signal (CTS) which in some examples may be related to the pentapeptide motif KFERQ (SEQ ID NO: 26). A CTS is necessary to induce CMA, and is found in all substrate proteins of CMA to date. In order to utilize CMA for targeted protein degradation, the peptides of the present invention comprise a protein binding domain (PBD) that can specifically recognize and bind to the target protein, fused to a CTS that can deliver the peptide-protein complex into the lysosome for degradation. The peptides of the invention may further comprise a cell membrane penetrating domain (CMPD) that can deliver the peptide across the plasma membrane (Example shown in FIG. 1). The CMPD may be the protein transduction domain of the HIV-1 Tat protein, GRKKRRQRRRPPQ (SEQ ID NO: 5); the *Drosophila melanogaster* Antennapedia domain Antp (amino acids 43-58), RQIKWFQNRRMKWKK (SEQ ID NO: 6); Buforin II, TRSSRAGLQFPVGRVHRLLRK (SEQ ID NO: 7); hClock-(amino acids 35-47) (human Clock protein DNA-binding peptide), KRVSRNKSEKKRR (SEQ ID NO: 8); MAP (model amphipathic peptide), KLALKLALKAL-KAALKLA (SEQ ID NO: 9); K-FGF, AAVALLPAVLLAL-LAP (SEQ ID NO: 10); Ku70-derived peptide, comprising a peptide selected from the group comprising VPMLKE (SEQ ID NO: 11), VPMLK (SEQ ID NO: 12), PMLKE (SEQ ID NO: 13) or PMLK (SEQ ID NO: 14); Prion, Mouse Prpe (amino acids 1-28), MANLGYWLLA-LFVTMWTDVGLCKKRPKP (SEQ ID NO: 15); pVEC, LLIILRRRIRKQAHAHSK (SEQ ID NO: 16); Pep-I, KETWWETWWTEWSQPKKKRKV (SEQ ID NO: 17); SynB1, RGGRLSYSRRRFSTSTGR (SEQ ID NO: 18); Transportan, GWTLNSAGYLLGKINLKALAALAKKIL (SEQ ID NO: 19); Transportan-10, AGYLLGKINLKA-LAALAKKIL (SEQ ID NO: 20); CADY, Ac-GL-WRALWRLLRSLWRLLWRA-cysteamide (SEQ ID NO: 21); Pep-7, SDLWEMMMVSLACQY (SEQ ID NO: 22); HN-1, TSPLNIHNGQKL (SEQ ID NO: 23); VT5, DPKGDPKGVTVTVTVTVTGKGDPKPD (SEQ ID NO: 24); pISL, RVIRVWFQNKRCKDKK (SEQ ID NO: 25); or any other known CMPD.

Thus, in one aspect of the invention, there is provided a knockdown targeting peptide composition comprising a CMA-targeting signal (CTS) fused to a protein binding domain (PBD), wherein the protein binding domain is a polypeptide sequence that is capable of selectively binding to an endogenous protein such that contacting the knockdown targeting peptide with the endogenous protein in a cellular environment will cause the lysosomal degradation of the endogenous protein. The targeting peptide composition may further comprise a cell membrane penetrating domain (CPMD). The CPMD may be the protein transduction domain of the HIV-1 Tat protein, GRKKRRQRRRPPQ (SEQ ID NO: 5); the *Drosophila melanogaster* Antennapedia domain Antp (amino acids 43-58), RQIKWFQNRRMKWKK (SEQ ID NO: 6); Buforin II, TRSSRAGLQFPVGRVHRLLRK (SEQ ID NO: 7); hClock-(amino acids 35-47) (human Clock protein DNA-binding peptide), KRVSRNKSEKKRR (SEQ ID NO: 8); MAP (model amphipathic peptide), KLALKLALKAL-KAALKLA (SEQ ID NO: 9); K-FGF, AAVALLPAVLLAL-LAP (SEQ ID NO: 10); Ku70-derived peptide, comprising a peptide selected from the group comprising VPMLKE (SEQ ID NO: 11), VPMLK (SEQ ID NO: 12), PMLKE (SEQ ID NO: 13) or PMLK (SEQ ID NO: 14); Prion, Mouse Prpe (amino acids 1-28), MANLGYWLLA-LFVTMWTDVGLCKKRPKP (SEQ ID NO: 15); pVEC, LLIILRRRIRKQAHAHSK (SEQ ID NO: 16); Pep-I, KETWWETWWTEWSQPKKKRKV (SEQ ID NO: 17); SynB1, RGGRLSYSRRRFSTSTGR (SEQ ID NO: 18); Transportan, GWTLNSAGYLLGKINLKALAALAKKIL (SEQ ID NO: 19); Transportan-10, AGYLLGKINLKA-LAALAKKIL (SEQ ID NO: 20); CADY, Ac-GL-WRALWRLLRSLWRLLWRA-cysteamide (SEQ ID NO: 21); Pep-7, SDLWEMMMVSLACQY (SEQ ID NO: 22); HN-1, TSPLNIHNGQKL (SEQ ID NO: 23); VT5, DPKGDPKGVTVTVTVTVTGKGDPKPD (SEQ ID NO: 24); pISL, RVIRVWFQNKRCKDKK (SEQ ID NO: 25); or any other known CMPD.

Therefore, the present invention provides a peptide comprising a CMA-targeting signal domain, a protein binding domain that selectively binds to a target protein, and a cell membrane penetrating domain. In one aspect of the invention, the target protein is an endogenous target protein. In another aspect, the peptide is systemically administered to an animal to reduce the cellular expression level of an endogenous target protein.

In another aspect of the invention, there is provided a method for reducing the intracellular expression level of a target protein in vitro or in vivo in an animal in need thereof. When used in vitro, the method comprises co-expression of the target protein and a peptide comprising a CTS domain and a PBD that selectively binds to the target protein. The in vivo method comprises administration to an animal in need thereof the peptide described herein, which comprises a CTS domain, a PBD that selectively binds to a target protein, and a cell membrane penetrating domain.

Also provided is a use of a peptide comprising a CTS domain, a PBD that selectively binds to a target protein, and a cell membrane penetrating domain for reducing the intracellular expression level of the target protein in vitro or in vivo. Also provided is a use of a peptide described herein in the manufacture of a medicament for reducing the intracellular expression level of the target protein. In another aspect, there is provided a peptide described herein for use in reducing the intracellular expression level of the target protein in vitro or in vivo.

In another aspect of the invention, there is provided a method of treatment of a disease for which it would be desirable to knockdown the cellular expression of a particular endogenous protein, the method comprising administering to a subject having or suspected of having such disease a therapeutically effective amount of a knockdown targeting peptide, wherein the knockdown targeting peptide comprises a CMA-targeting signal (CTS) fused to a protein binding domain (PBD), wherein the protein binding domain is a polypeptide sequence that is capable of selectively binding to the endogenous protein. The knockdown targeting peptide may further comprise a cell membrane penetrating domain (CMPD) that can deliver the peptide across the plasma membrane. The CMPD may be the protein transduction domain of the HIV-1 Tat protein, GRKKRRQRRRPPQ (SEQ ID NO: 5); the *Drosophila melanogaster* Antennapedia domain Antp (amino acids 43-58), RQIKWFQNRRMKWKK (SEQ ID NO: 6); Buforin II, TRSSRAGLQFPVGRVHRLLRK (SEQ ID NO: 7); hClock-(amino acids 35-47) (human Clock protein DNA-binding peptide), KRVSRNKSEKKRR (SEQ ID NO: 8); MAP (model amphipathic peptide), KLALKLALKAL-KAALKLA (SEQ ID NO: 9); K-FGF, AAVALLPAVLLAL-LAP (SEQ ID NO: 10); Ku70-derived peptide, comprising a peptide selected from the group comprising VPMLKE (SEQ ID NO: 11), VPMLK (SEQ ID NO: 12), PMLKE (SEQ ID NO: 13) or PMLK (SEQ ID NO: 14); Prion, Mouse Prpe (amino acids 1-28), MANLGYWLLA-LFVTMWTDVGLCKKRPKP (SEQ ID NO: 15); pVEC, LLIILRRRIRKQAHAHSK (SEQ ID NO: 16); Pep-I, KETWWETWWTEWSQPKKKRKV (SEQ ID NO: 17); SynBl, RGGRLSYSRRRFSTSTGR (SEQ ID NO: 18); Transportan, GWTLNSAGYLLGKINLKALAALAKKIL (SEQ ID NO: 19); Transportan-10, AGYLLGKINLKA-LAALAKKIL (SEQ ID NO: 20); CADY, Ac-GL-WRALWRLLRSLWRLLWRA-cysteamide (SEQ ID NO: 21); Pep-7, SDLWEMMMVSLACQY (SEQ ID NO: 22); HN-1, TSPLNIHNGQKL (SEQ ID NO: 23); VT5, DPKGDPKGVTVTVTVTVTGKGDPKPD (SEQ ID NO: 24); pISL, RVIRVWFQNKRCKDKK (SEQ ID NO: 25); or any other known CMPD.

In another aspect, there is provided a use of a peptide comprising a CTS domain, a PBD that selectively binds to an endogenous target protein, and a cell membrane penetrating domain for reducing the intracellular expression level of the endogenous target protein in an animal to treat a disease in the animal. Also provided is a use of a peptide described herein in the manufacture of a medicament for reducing the intracellular expression level of the endogenous target protein to treat a disease in the animal. In another aspect, there is provided a peptide described herein for use in reducing the intracellular expression level of the endogenous target protein to treat a disease in the animal.

The compounds described herein may be used for in vivo or in vitro research uses (i.e. non-clinical) to investigate alternative treatments for diseases for which it would be desirable to knockdown an endogenous protein. Furthermore, these isolated polypeptides may be used individually or as part of a kit for in vivo or in vitro research to investigate mechanisms of lysosomal degradation, nucleotides encoding the isolated polypeptides, cells maintained in culture, and/or animal models.

The endogenous target protein may be any endogenous, native protein that has a binding partner or for which a binding domain sequence is known or can be obtained. For example, the target protein may be α-synuclein, Post Synaptic Density 95 (PSD 95), death-associated protein kinase 1 (DAPK1), or any cytosolic protein kinase for which a peptide binding domain has been or can be identified.

The present invention, therefore, also relates to a novel knockdown targeting peptide composition capable of targeting and knocking down α-synuclein, a protein implicated in neurodegenerative synucleinopathies such as Parkinson's disease. In one aspect, there is provided an isolated polypeptide having substantial similarity to SEQ ID NO:1. In another aspect, there is provided an isolated polypeptide having at least 90% identity to any one of: SEQ ID NO:1; wherein the identity may be calculated over the length of the sequence, and wherein the isolated polypeptide causes degradation of α-synuclein. In another aspect, there is provided an isolated polypeptide having at least 95% identity to any one of: SEQ ID NO:1; wherein the identity may be calculated over the length of the sequence, and wherein the isolated polypeptide causes degradation of α-synuclein. In another aspect, there is provided an isolated polypeptide comprising any one of: SEQ ID NO:1.

The isolated polypeptide may cause degradation or knockdown of α-synuclein. The isolated polypeptide may further include a delivery and targeting moiety conjugated to the isolated polypeptide. The delivery and targeting moiety may be selected from one or more of: ligands; protein transduction domains; or antibodies. The protein transduction domain may be the cell-membrane transduction domain of the HIV-1 Tat protein. In one aspect, there is provided an isolated polypeptide having substantial similarity to SEQ ID NO:2. In another aspect, there is provided an isolated polypeptide having at least 90% identity to any one of: SEQ ID NO:2; wherein the identity may be calculated over the length of the sequence, and wherein the isolated polypeptide causes degradation of α-synuclein. In another aspect, there is provided an isolated polypeptide having at least 95% identity to any one of: SEQ ID NO:2; wherein the identity may be calculated over the length of the sequence, and wherein the isolated polypeptide causes degradation of α-synuclein. In another aspect, there is provided an isolated polypeptide comprising any one of: SEQ ID NO:2.

In another aspect of the invention, there is provided a method of treating a subject having or suspected of having a disease for which it would be desirable to reduce the level of α-synuclein, the method comprising administering to the subject a therapeutically effective amount of a knockdown targeting peptide that targets α-synuclein. The peptide may cause degradation or knockdown of α-synuclein. The peptide may further include a delivery and targeting moiety conjugated to the isolated polypeptide. The knockdown targeting peptide may be substantially similar to SEQ ID NO: 1 or 2. The knockdown targeting peptide may be 90%, 95%, 99%, or 100% identical to SEQ ID NO: 1 or 2. The disease may be Parkinson's Disease.

The present invention also relates to a novel knockdown targeting peptide composition capable of selectively targeting and knocking down a cytosolic protein kinase. In certain embodiments, the present invention relates to the selective knockdown of an activated cytosolic protein kinase. For example, the protein kinase may be death-associated protein kinase 1 (DAPK1). DAPK1 is a calcium-calmodulin regulated protein kinase, which when inactive does not interact with the N-methyl-D-aspartate (NMDA) receptor NR2B subunit. DAPK1 is a cell death promoting protein kinase in many cell types, and is known to be required for cell death under pathological conditions such as excitotoxic/ischemic neuronal injuries or oxidative stress. These processes are known to be involved in various neurodegenerative diseases such as Alzheimer's Disease, Parkinson's Disease, amyotrophic lateral sclerosis (ALS), as well as other conditions such as stroke In one aspect, there is provided an isolated polypeptide having substantial similarity to SEQ ID NO:3. In another aspect, there is provided an isolated polypeptide having at least 90% identity to any one of: SEQ ID NO:3; wherein the identity may be calculated over the length of the sequence, and wherein the isolated polypeptide causes degradation of DAPK1. In another aspect, there is provided an isolated polypeptide having at least 95% identity to any one of: SEQ ID NO:3; wherein the identity may be calculated over the length of the sequence, and wherein the isolated polypeptide causes degradation of DAPK1. In another aspect, there is provided an isolated polypeptide comprising any one of: SEQ ID NO:3.

The isolated polypeptide may cause degradation or knockdown of DAPK1. The isolated polypeptide may further include a delivery and targeting moiety conjugated to the isolated polypeptide. The delivery and targeting moiety may be selected from one or more of: ligands; protein transduction domains; or antibodies. The protein transduction domain may be the cell-membrane transduction domain of the HIV-1 Tat protein. In one aspect, there is provided an isolated polypeptide having substantial similarity to SEQ ID NO:4. In another aspect, there is provided an isolated polypeptide having at least 90% identity to any one of: SEQ ID NO:4; wherein the identity may be calculated over the length of the sequence, and wherein the isolated polypeptide causes degradation of DAPK1. In another aspect, there is provided an isolated polypeptide having at least 95% identity to any one of: SEQ ID NO:4; wherein the identity may be calculated over the length of the sequence, and wherein the isolated polypeptide causes degradation of DAPK1. In another aspect, there is provided an isolated polypeptide comprising any one of: SEQ ID NO:4.

In another aspect of the invention, there is provided a method of treating a subject having or suspected of having a disease for which it would be desirable to reduce the level of DAPK1, the method comprising administering to the subject a therapeutically effective amount of a knockdown targeting peptide that targets DAPK1. The peptide may cause degradation or knockdown of DAPK1. The peptide may further include a delivery and targeting moiety conjugated to the isolated polypeptide. The knockdown targeting peptide may be substantially similar to SEQ ID NO: 3 or 4. The knockdown targeting peptide may be 90%, 95%, 99%, or 100% identical to SEQ ID NO: 3 or 4. The disease may be associated with oxidative stress or excitotoxic stress. The disease may be a neurodegenerative disease. The disease may be Alzheimer's Disease, Parkinson's Disease, ALS or stroke.

In another aspect of the invention, there is provided a method of treating a pathological condition in an animal in need thereof, the method comprising administering to the animal a therapeutically effective amount of a peptide comprising a CTS domain, a PBD that selectively binds to a target protein, and a cell membrane penetrating domain, wherein the peptide reduces the intracellular expression level of the target protein in the animal. The pathological condition may be a neurodegenerative disease of the central nervous system, such as Alzheimer's disease, amyotrophic lateral sclerosis (ALS), Parkinson's disease or Huntington's disease. The pathological condition may also be a spinal cord injury, stroke, a traumatic brain injury, alcoholism or alcohol withdrawal.

In another aspect, there is provided an isolated polynucleotide, including a series of nucleotides encoding the polypeptide described herein.

In another aspect, there is provided a composition comprising the polypeptide as described herein and a carrier. The carrier may be a pharmaceutically acceptable carrier. Therefore, also provided herein is a pharmaceutical composition comprising the peptide described herein and a pharmaceutically acceptable carrier, diluent, or excipient.

In another aspect, there is provided a method for treating a disease comprising co-administration of the pharmaceutical composition described herein and another pharmaceutically active agent.

In another aspect, there is provided a vector comprising an isolated polynucleotide as described herein. In another aspect, there is provided a cell including the vector as described herein. In another aspect, there is provided a cell including a polynucleotide as described herein, wherein the polynucleotide may be operably linked to an expression control sequence.

In another aspect, there is provided a method of protecting a cell from cell death and/or apoptosis, the method including delivering an isolated polypeptide as described herein to the cell.

In another aspect, there is provided a method of protecting a cell from cell death and/or apoptosis, the method including: (a) delivering the vector as described herein to the cell; and (b) expressing the polynucleotide carried by the vector.

In another aspect, there is provided a method of expressing a polypeptide, the method including: (a) delivering the vector of as described herein to a cell; and (b) maintaining the cell under conditions permitting expression of the polynucleotide carried by the vector.

The delivering of the vector to the cell may be carried out in vivo. The delivering of the vector to the cell may be carried out ex vivo. The delivering of the vector to the cell may be carried out in vitro.

In another aspect, there is provided a proteasome-targeting peptide comprising a proteasome-targeting signal domain, a protein-binding domain that selectively binds to a target protein, and a cell membrane penetrating domain, wherein the proteasome-targeting peptide is for reducing the intracellular expression level of the target protein using proteasomal degradation.

In another aspect, there is provided a method for reducing the intracellular expression level of a target protein comprising co-administration of the peptide comprising a CTS domain and the proteasome-targeting peptide described herein.

Other aspects and features of the present invention will become apparent to those ordinarily skilled in the art upon review of the following description of specific embodiments of the invention in conjunction with the accompanying figures.

BRIEF DESCRIPTION OF FIGURES

FIG. 1(a-d). Method to rapidly and reversibly knockdown an endogenous protein of interest by peptide-directed lysosomal protein degradation in accordance with an exemplary embodiment of the present invention. (a) Schematic representation of the targeting peptide-mediated protein degradation. Following administration, the targeting peptide enters the cell through its cell membrane penetrating domain (CMPD), binds to the target protein via its protein binding domain (PBD), and chaperones the peptide-protein complex to the lysosome for degradation via its chaperone-mediated autophagy targeting signal (CTS). (b-d) The CTS is sufficient to direct the tagged GFP protein to the lysosome for degradation. (b) Linear representation of constructs CTS-GFP and mCTS-GFP. CTS-GFP was constructed by linking amino acid sequence of CTS to GFP at its C terminal. mCTS-GFP was constructed by mutating the two glutamine amino acid residues (Q, highlighted in red) of the CTS-GFP into alanines (A, highlighted in red) that render the CTS (mCTS) functionally incompetent. Sequences in FIG. 1b: KFERQKILDQRFFE (SEQ ID NO:53) and KFERAKILDARFFE (SEQ ID NO:54). (c) Representative confocal images of colocalization of GFP with the lysosome marker lamp1 in COS7 cells transfected with either wild-type GFP (WT-GFP; top) or CMA-tagged GFP (CTS-GFP; bottom). CTS-GFP, but not WT-GFP, was directed to the lysomomal compartment. Scale bar: 20 µM. (d) Quantification of CTS-GFP and mCTS-GFP levels relative to WT-GFP in COS7 cells 24 hours after individual transfections with WT-GFP, mCTS-GFP or CTS-GFP. Cells transfected with WT-GFP or CTS-GFP were treated without (No Treatment) or with serum deprivation (+SD; n=5; to enhance CMA activity) or macroautophagy inhibitor (+3-MA; 10 mM; n=5), proteasome inhibitor (+MG132; 5 µM; n=6), or lysosome inhibitor ammonium chloride (+NH$_4$Cl; 20 mM; n=6) or pepstatin A (+PepA; 10 µM; n=5). Top panels are representative immunoblotting of cell lysates for GFP. Membrane re-probing for β-actin was used as loading control. Bars in bottom panel represent relative protein levels, normalized to WT-GFP (arbitrarily set as 1; white bar). *$p<0.05$, $p<0.01$, *$p<0.001$ versus WT-GFP (white bar); $^{\triangle}p<0.05$, $^{\triangle\triangle}p<0.01$, $^{\triangle\triangle\triangle}p<0.001$ relative to non-treated CTS-GFP levels (grey bar). Bars represent mean values±s.e.m.

FIG. 3(a-f). Reversible and dose- and activity dependent knock-down of native DAPK1 by plasma membrane permeant recombinant CMA-targeting peptide in cultured cortical neurons. (a) NMDA treatment (50 µM; 30 min) activates DAPK1, and induces its association with NMDA receptors. Sequential immunoblots for phosphorylated DAPK1 (pDAPK1) and for total DAPK1 (DAPK1) in the top panel revealed that NMDA stimulation activates DAPK1 as demonstrated by the time dependent decrease in its phosphorylation levels. Bottom panel: Co-immunoprecipitation of DAPK1 with anti-NR2B followed by sequential immunoblotting for DAPK1 (DAPK1) and NR2B subunit (NR2B) showed an induced association between DAPK1 and NR2B following NMDA stimulation. (b) Design and production of the membrane permeable recombinant TATNR2Bct-CTS and TAT-NR2Bct peptides (schematically shown in bottom panel) using *E. coli* expression system. The purity of peptides was visualized by Coomassie blue staining on SDS-PAGE (top panel). Sequences in FIG. 3b: YGRKKRRQRRR (SEQ ID NO:57) and KFERQKILDQRFFE (SEQ ID NO:53). (c-f) TAT-NR2Bct-CTS, but not TAT-NR2Bct decreases the level of DAPK1 by directing it for lysosomal degradation in a NMDA activation dependent manner. In all graphs, relative levels of DAPK1 were normalized to the DAPK1 levels in non-treated naïve group (white bar, arbitrarily set as 1), and compared to naïve (white bar, *) or NMDA-treated group (grey bar, Δ). Membrane reprobing for β-actin was used as loading control. (c) TAT-NR2Bct-CTS (n=9), but not TAT-NR2Bct (n=6), knocked down the DAPK1 activated by NMDA stimulation and this knockdown was prevented in the presence of lysosome inhibitor $NH_4Cl$ (20 mM; n=5). Peptides were bath applied to the neurons at 200 μM 60 min prior to and during the NMDA stimulation (50 μM; 30 min) and DAPK1 levels were then determined 2 hours after washing off NMDA and the peptides. TAT-NR2Bct-CTS-mediated DAPK1 knockdown is dose-dependent (d; n=4) and time-dependent (e; n=6). (f) The DAPK1 knockdown is persistent in the presence of TAT-NR2Bct-CTS. DAPK1 levels were determined 7 hours after washing off NMDA and the peptides. The single pretreatment of His-TAT-NR2Bct-CTS (sing.; 200 μM, 60 min prior to and during the 30 min NMDA stimulation) resulted in a transient reduction of DAPK1, returning to the untreated levels within 7 hours (n=4; p=0.888 compared to NMDA-treated group (grey bar)). However, an additional dose of the peptide after NMDA washout produced persistent reduction in DAPK1, remaining low at 7 hours (n=4; $^{ΔΔ}$p=0.002, compared to NMDA-treated group).

FIG. 8(a-c). siRNA-directed knockdown of Lamp2a reduces TAT-NR2BCTM induced DAPK1 degradation. (a and b) Immunoblots of Lamp2a showing siRNA (60 pmol)-directed knockdown of Lamp2a 3 days after siRNA treatment, without apparent cell toxicity measured by LDH assay (b) Positive control was obtained by lysing cells with Triton X-100 prior to LDH assay. n=3, One way ANOVA, p=0.024, F(3,8)=5.474. Scrb-siRNA: scrambled siRNA, Lamp2a-siRNA: Lamp2a-targeting siRNA. (c) Sequential immunoblotting showing the inhibition of TAT-NR2BCTM induced knockdown of DAPK1 by specifically blocking CMA with siRNA-mediated Lamp2a knockdown. 3ds days following siRNA treatment, cells were incubated in TAT-NR2BCTM (25 μM) for 1 hour before and during NMDA (50 μM; 30 min). Cells were harvested 2 hours after the peptide and NMDA washout. β-actin was used as loading control. Lamp2a-knockdown: n=7, One way ANOVA p<0.001, F(3, 24)=13.455; DAPK1 Knockdown: n=7, Kruskal-Wallis One Way Analysis of Variance on Ranks with Tukey post-hoc, p=0.002, H(3)=15.047; *compared to naïve control, Δ compared to NMDA-treated group (grey bar). *,Δp<0.05, p<0.01 and *p<0.001; bars represent relative mean values±s.e.m. normalized to the naïve non-treated control (arbitrarily set as 1).

FIG. 10(a-c). Immunoblots showing that the macroautophagy inhibitor 3-methyladenine (3-MA) cannot rescue targeting-peptide mediated degradation. (a) α-synuclein targeting peptide TAT-βsyn-CTM (25 μM) significantly decreased native α-synuclein in the presence of 3-MA (10 mM). Basal level of α-synuclein showed a non-significant trend of increase with the addition of 3-MA (N=5, p<0.001, F(3,16)=47.013). (b) 3-MA did not alter either the basal levels or NMDA activation-dependent knockdown of DAPK1 by its targeting peptide TAT-NR2BCTM (n=4, p<0.001, F(3,12)=21.675). (c) Similarly, 3-MA failed to affect either the basal or the TAT-NR2B9c reduced level of PSD95 (n=4, p<0.001, F(3,12)=14.836). β-actin was used as loading control. One way ANOVA with Tukey's post-hoc. *p<0.05, p<0.01 and *p<0.001; bars represent relative mean values±s.e.m. normalized to the naïve non-treated control (arbitrarily set as 1).

FIG. 12(a-e). Systemic applications of TAT-NR2BCTM specifically knock down DAPK1 in the ischemic brain areas and reduce ischemic neuronal damage in the rat middle cerebral artery occlusion focal ischemia model in vivo. (a) Schematic showing experimental protocol including timeline of tissue collection for immunoblot and immunohistochemistry analysis of DAPK1 degradation in rats subjected to 1 hour transient MCAO. (b) Images of 2,3,5-triphenyltetrazolium chloride (TTC) staining of a series of transverse brain sections showing the MCAO challenge reliably induces damage/infarct areas in the ipsilateral side of the brain. (c) Black-dashed lines in a representative TTC-stained brain section showing brain areas removed for immunoblotting. (d) Immunoblots for DAPK1 demonstrate a specific knockdown of DAPK1 only in tissues collected from the infract side (MCAO), but not the contralateral side (Control) following systemic application of TAT-NR2BCTM (10 mg/kg, i.v.; n=3; two-tailed student's t-test, t(4)=14.459, p<0.001), but not its control TAT-NR2B (10 mg/kg, i.v.; n=3; two-tailed student's t-test, t(4)=0.739, p=0.501). Membranes re-probed for β-actin were used as a loading control. ***p<0.001; bars represent relative mean values±s.e.m. normalized to non-occluded control side (arbitrarily set as 1). (e) Representative images of Hematoxylin & Eosin (H&E staining; pink; left panels) and immunohistochemical DAPK1 staining (IHC for DAPK1; green; right panels) of adjacent brain sections rats showing that in comparison with saline (top panels) and TAT-NR2B-treated (middle panels) controls, TAT-NR2BCTM treatment (bottom panels) selectively reduced the level of DAPK1 (right; green) and infarct areas (left; pink) in MCAO side of the brain. Note: TAT-NR2BCTM only reduces DAPK1 in regions corresponding to infarct brain areas. The efficient knockdown of DAPK1 is associated with a dramatic reduction of brain damage.

DETAILED DESCRIPTION

Figure 2A:
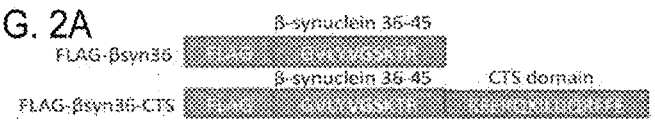
FIG. 2(a-h). CTS-containing peptide can target its binding partner for CMA-mediated lysosomal degradation through a peptide-protein interaction. (a-c). Dose-dependent knocking down of α-synuclein by targeting peptide directed lysosomal protein degradation. Sequences in FIG. 2a: GVLYVGSKTR (SEQ ID NO:55), KFERQKILDQRFFE (SEQ ID NO:53) and GVLYVGSKTRKFERQKILDQRFFE (SEQ ID NO:1). Schematic representation of FLAG-βsyn36 and FLAG-βsyn36-CTS peptide constructs is shown in b. The β-synuclein 36-45 amino acid sequence constitutively binds to α-synuclein, forming the α-synuclein-binding domain of the targeting peptide. α-synuclein was co-expressed with either FLAG-βsyn36-CTS (b) or FLAG-βsyn36 (c) at various ratios in HEK cells and immunoblots for α-synuclein was performed 48 hrs after transfection. Quantifications of α-synuclein levels relative to α-synuclein alone (ratio 0:1; white bar) in bar graphs on top and representative immunoblots shown on bottom revealed that co-expression of βsyn36-CTS (b; n=8), but not βsyn36 (c; n=4), peptide with α-synuclein in HEK cells constitutively reduced α-synuclein in a dose-dependent manner. FLAG-βsyn36-CTS induced α-synuclein reduction was prevented by lysosomal inhibitor NH$_4$Cl (b; 20 mM; n=7). (d-h) Dose-dependent knock-down of active, but not inactive, DAPK1 by the targeting peptide directed lysosomal degradation. Anti-HA was used to detect HA-NR2Bct-CTS and HA-NR2Bct-CTSm, while anti-FLAG was used to detect wtDAPK and cDAPK. (d) Schematic illustration of the exemplary DAPK1 targeting peptide HA-NR2Bct-CTS and its non-functional CTS (CTSm) control peptide HA-NR2Bct-CTSm. The DAPK1-binding domain of the HA-NR2Bct-CTS contains the amino acid sequence between the residue of 1242-1342 of the carboxyl tail region of NR2B subunit of NMDA receptors that can only specifically bind to active, but not inactive DAPK1. Flag-tagged wild type (inactive) DAPK1 (wtDAPK1) or constitutively active mutant of DAPK1 (cDAPK1) was co-expressed with either HA-NR2Bct-CTS or HA-NR2Bct-CTSm at various ratios in HEK cells, and co-IP and/or immunoblotting was performed 24 hours thereafter. Reciprocal co-immunoprecipitation followed by immunoblotting revealed that NR2Bct specifically interacts with cDAPK1, but not wtDAPK1 (e) HA-NR2Bct-CTS specifically and dose-dependently decreases the levels of cDAPK1 (f; n=4), but not wtDAPK1 (g; n=3). The HA-NR2Bct-CTS mediated cDAPK1 knockdown is significantly prevented by lysosomal inhibition with NH$_4$Cl (20 mM; n=4; $^{\triangle\triangle\triangle}$ $p<0.001$, compared to HA-NR2Bct-CTS: cDAPK1=8:1 group) and by mutational inactivation of the CMA targeting signal (h); HA-NR2Bct-CTSm; n=8). Levels of α-synuclein (b-c), cDAPK1 or wtDAPK1 (e-g) co-transfected with pcDNA3.0 vector (0:1, white bar) represent the control values, being arbitrarily set as 1. Membrane-probing for β-actin was used as loading control. Sequences in FIG. 2d: YPYDVPDYA (SEQ ID NO:56), KFERQKILDQRFFE (SEQ ID NO:53), and KFERAKILDARFFE (SEQ ID NO:54). *$p<0.05$ $p<0.01$ *$<0.001$, compared with the control. Bars represent relative mean values±s.e.m.

As used herein, the term "knockdown" is used to refer to the reduction in the expression level of a protein in a cell.

Accordingly, "knockdown" may be used interchangeably with the phrases "reduction of the levels of the protein," "reduction in the expression level of a protein," "reduction of the intracellular expression level of a protein" or any variation of these phrases.

The term "identity" as used herein refers to the measure of the identity of sequence between two peptides or between two nucleic acids molecules. Identity can be determined by comparing a position in each sequence which may be aligned for purposes of comparison. Two amino acid or nucleic acid sequences are considered substantially identical if they share at least about 80% sequence identity or at least about 81% sequence identity, or at least about 82% sequence identity, or at least about 83% sequence identity, or at least about 84% sequence identity, or at least about 85% sequence identity, or at least about 86% sequence identity, or at least about 87% sequence identity, or at least about 88% sequence identity, or at least about 89% sequence identity, or at least about 90% sequence identity. Alternatively, two amino acid or nucleic acid sequences are considered substantially identical if they share at least about 91% sequence identity, or at least about 92% sequence identity, or at least about 93% sequence identity, or at least about 94% sequence identity, or at least about 95% sequence identity, or at least about 96% sequence identity, or at least about 97% sequence identity, or at least about 98% sequence identity, or at least about 99% sequence identity.

Sequence identity may be determined by the BLAST algorithm currently is use and which was originally described in Altschul et al. (1990) J. Mol. Biol. 215:403-410. The BLAST algorithm may be used with the published default settings. When a position in the compared sequence is occupied by the same base or amino acid, the molecules are considered to have shared identity at that position. The degree of identity between sequences is a function of the number of matching positions shared by the sequences and the degree of overlap between the sequences. Furthermore, when considering the degree of identity with SEQ ID NOs:1-4, it is intended that the equivalent number of amino acids be compared to SEQ ID NOs:1-4, respectively. Additional sequences (i.e. other than those corresponding to the 20, 10, or 15 amino acids of SEQ ID NOs:1-4, respectively), are not intended to be considered when determining the degree of identity with SEQ ID NOs:1-4. The sequence identity of a given sequence may be calculated over the length of the reference sequence (i.e. SEQ ID NOs:1-4).

In certain embodiments, there is provided an isolated polypeptide composition having an amino acid composition substantially similar to SEQ ID NO: 1-4. Wherein substantially similar is meant to encompass a degree of sequence identity when an equivalent region (i.e. ~20 or 10 or 15 amino acids, respectively) is compared. Furthermore, substantially similar is meant to encompass conservative substitutions and modified amino acids provided that cell protection activity or other activities described herein are maintained.

As used herein, 'peptide' or 'polypeptide' may be used interchangeably, and generally refer to a compound comprised of at least two amino acid residues covalently linked by peptide bonds or modified peptide bonds. However, when specifically used with reference to a specific SEQ ID NO, it is meant to comprise an amino acid sequence of α-synuclein represented by SEQ ID NO:1 or 2, or DAPK1 represented by SEQ ID NO:3 or 4, wherein the polypeptide has cell protective activity. Modified peptide bonds may include for example peptide isosteres (modified peptide bonds) that may provide additional desired properties to the peptide, such as increased half-life. A peptide may comprise at least two amino acids. The amino acids comprising a peptide or polypeptide described herein may also be modified either by natural processes, such as posttranslational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide.

Amino acids are molecules containing an amine group, a carboxylic acid group and a side chain that varies between different amino acids. An amino acid may be in its natural form or it may be a synthetic amino acid. An amino acid may be described as, for example, polar, non-polar, acidic, basic, aromatic or neutral. A polar amino acid is an amino acid that may interact with water by hydrogen bonding at biological or near-neutral pH. The polarity of an amino acid is an indicator of the degree of hydrogen bonding at biological or near-neutral pH. Examples of polar amino acids include serine, proline, threonine, cysteine, asparagine, glutamine, lysine, histidine, arginine, aspartate, tyrosine and glutamate. Examples of non-polar amino acids include glycine, alanine, valine, leucine, isoleucine, methionine, phenylalanine, and tryptophan. Acidic amino acids have a net negative charge at a neutral pH. Examples of acidic amino acids include aspartate and glutamate. Basic amino acids have a net positive charge at a neutral pH. Examples of basic amino acids include arginine, lysine and histidine. Aromatic amino acids are generally nonpolar, and may participate in hydrophobic interactions. Examples of aromatic amino acids include phenylalanine, tyrosine and tryptophan. Tyrosine may also participate in hydrogen bonding through the hydroxyl group on the aromatic side chain. Neutral, aliphatic amino acids are generally nonpolar and hydrophobic. Examples of neutral amino acids include alanine, valine, leucine, isoleucine and methionine. An amino acid may be described by more than one descriptive category. Amino acids sharing a common descriptive category may be substitutable for each other in a peptide. An amino acid residue may be generally represented by a one-letter or three-letter designation, corresponding to the trivial name of the amino acid, in accordance with the following Table A. Amino acids comprising the peptides described herein will be understood to be in the L- or D-configuration. Amino acids described herein, may be modified by methylation, amidation, acetylation or substitution with other chemical groups which may change the circulating half-life of the peptide without adversely affecting their biological activity. Additionally, a disulfide linkage may be present or absent in the peptides of the invention. Nonstandard amino acids may occur in nature, and may or may not be genetically encoded. Examples of genetically encoded nonstandard amino acids include selenocysteine, sometimes incorporated into some proteins at a UGA codon, which may normally be a stop codon, or pyrrolysine, sometimes incorporated into some proteins at a UAG codon, which may normally be a stop codon. Some nonstandard amino acids that are not genetically encoded may result from modification of standard amino acids already incorporated in a peptide, or may be metabolic intermediates or precursors, for example. Examples of nonstandard amino acids include 4-hydroxyproline, 5-hydroxylysine, 6-N-methyllysine, gamma-carboxyglutamate, desmosine, selenocysteine, ornithine, citrulline, lanthionine, 1-aminocyclopropane-1-carboxylic acid, gamma-aminobutyric acid, carnitine, sarcosine, or N-formylmethionine. Synthetic variants of standard and non-standard amino acids are also known and may include chemically derivatized amino acids, amino acids labeled for identification or tracking, or amino acids with a variety of side groups on the alpha carbon. Examples of such side groups are known in the art and may include aliphatic, single aromatic, polycyclic aromatic, heterocyclic, heteronuclear, amino, alkylamino, carboxyl, carboxamide, carboxyl ester, guanidine, amidine, hydroxyl, alkoxy, mercapto-, alkylmercapto-, or other heteroatom-containing side chains. Other synthetic amino acids may include alpha-amino acids, non-alpha amino acids such as beta-amino acids, des-carboxy or des-amino acids. Synthetic variants of amino acids may be synthesized using general methods known in the art, or may be purchased from commercial suppliers, for example RSP Amino Acids LLC (Shirley, Mass.).

It will be appreciated by a person of skill in the art the aspects of the individual amino acids in a peptide or polypeptide described herein may be substituted. Amino acid sequence identity may be computed by using the BLASTP and TBLASTN programs which employ the BLAST (basic local alignment search tool) 2.0 algorithm. Techniques for computing amino acid sequence similarity or identity are well known to those skilled in the art, and the use of the BLAST algorithm is described in ALTSCHUL et al. 1990, J Mol. Biol. 215: 403-410 and ALTSCHUL et al. (1997), Nucleic Acids Res. 25: 3389-3402.

Furthermore, it will be appreciated by a person of skill in the art that certain substitutions are more likely to result in retention of activity. For example, amino acids may be described as, for example, polar, non-polar, acidic, basic, aromatic or neutral. A polar amino acid is an amino acid that may interact with water by hydrogen bonding at biological or near-neutral pH. The polarity of an amino acid is an indicator of the degree of hydrogen bonding at biological or near-neutral pH. Examples of polar amino acids include serine, proline, threonine, cysteine, asparagine, glutamine, lysine, histidine, arginine, aspartate, tyrosine and glutamate. Examples of non-polar amino acids include glycine, alanine, valine leucine, isoleucine, methionine, phenylalanine, and tryptophan. Acidic amino acids have a net negative charge at a neutral pH. Examples of acidic amino acids include aspartate and glutamate. Basic amino acids have a net positive charge at a neutral pH. Examples of basic amino acids include arginine, lysine and histidine.

Aromatic amino acids are generally nonpolar, and may participate in hydrophobic interactions. Examples of aromatic amino acids include phenylalanine, tyrosine and tryptophan. Tyrosine may also participate in hydrogen bonding through the hydroxyl group on the aromatic side chain. Neutral, aliphatic amino acids are generally nonpolar and hydrophobic. Examples of neutral amino acids include alanine, valine, leucine, isoleucine and methionine. An amino acid may be described by more than one descriptive category. Amino acids sharing a common descriptive category may be substitutable for each other in a peptide.

Nomenclature used to describe the peptides or polypeptides may follow the conventional practice where the amino group is presented to the left and the carboxy group to the right of each amino acid residue. In the sequences representing selected specific embodiments of the present invention, the amino- and carboxy-terminal groups, although not specifically shown, will be understood to be in the form they would assume at physiologic pH values, unless otherwise specified. In the amino acid structure formulae, each residue may be generally represented by a one-letter or three-letter designation, corresponding to the name of the amino acid, in accordance TABLE A.

TABLE A

Nomenclature and abbreviations of the 20 standard L-amino acids commonly found in naturally occurring peptides

| Full name | Three-letter abbreviation | One-letter abbreviation |
|---|---|---|
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asp | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | T |

Peptides may be modified in a variety of conventional ways well known to the skilled artisan. Examples of modifications include the following. The terminal amino group and/or carboxyl group of the peptide and/or amino acid side chains may be modified by alkylation, amidation, or acylation to provide esters, amides or substituted amino groups. Heteroatoms may be included in aliphatic modifying groups. This is done using conventional chemical synthetic methods. Other modifications include deamination of glutamyl and asparaginyl residues to the corresponding glutamyl and aspartyl residues, respectively; hydroxylation of proline and lysine; phosphorylation of hydroxyl groups of serine or threonine; and methylation of amino groups of lysine, arginine, and histidine side chains (see, for e.g.: T. E. Creighton, Proteins: Structure and Molecular Properties, W.H. Freeman & Co. San Francisco, Calif., 1983).

As used herein 'isolated' is meant to encompass a substance (such as, a polynucleotide or polypeptides or peptide) that has been substantially separated or purified away from other components, such as biological components, with which it would otherwise be associated, for example in vivo, so that the isolated substance may be itself be manipulated or processed. The term 'isolated' therefore includes substances purified by purification methods known in the art, as well as substances prepared by recombinant expression in a host, as well as chemically synthesized substances. In some embodiments, a compound is 'isolated' when it is separated from the components that naturally accompany it so that it is at least 60%, more generally 75% or over 90%, by weight, of the total relevant material in a sample. Thus, for example, a polypeptides that is chemically synthesized or produced by recombinant technology may be generally substantially free from its naturally associated components. A polynucleotide may be substantially pure when it is not immediately contiguous with (i.e., covalently linked to) the coding sequences with which it is normally contiguous in the naturally occurring genome of the organism from which the DNA of the invention is derived. An isolated compound can be obtained, for example, by extraction from a natural source; by expression of a recombinant nucleic acid molecule encoding a polypeptides compound; or by chemical synthesis. Purity can be measured using any appropriate method such as column chromatography, gel electrophoresis or HPLC.

One or both, but usually one terminus of the peptide, may be substituted with a lipophilic group, usually aliphatic or aralkyl group, which may include heteroatoms. Chains may be saturated or unsaturated. Conveniently, commercially available aliphatic fatty acids, alcohols and amines may be used, such as caprylic acid, capric acid, lauric acid, myristic acid and myristyl alcohol, palmitic acid, palmitoleic acid, stearic acid and stearyl amine, oleic acid, linoleic acid, docosahexaenoic acid, etc. (see, for e.g.: U.S. Pat. No. 6,225,444). Preferred are unbranched, naturally occurring fatty acids between 14-22 carbon atoms in length. Other lipophilic molecules include glyceryl lipids and sterols, such as cholesterol. The lipophilic groups may be reacted with the appropriate functional group on the oligopeptide in accordance with conventional methods, frequently during the synthesis on a support, depending on the site of attachment of the oligopeptide to the support. Lipid attachment is useful where oligopeptides may be introduced into the lumen of the liposome, along with other therapeutic agents for administering the peptides and agents into a host.

Depending upon their intended use, particularly for administration to mammalian hosts, the subject peptides may also be modified by attachment to other compounds for the purposes of incorporation into carrier molecules, changing peptide bioavailability, extending or shortening half-life, controlling distribution to various tissues or the blood stream, diminishing or enhancing binding to blood components, and the like. The prior examples serve as examples and are non-limiting.

Peptides may be prepared in a number of ways. Chemical synthesis of peptides is well known in the art. Solid phase synthesis is commonly used and various commercial synthetic apparatuses are available, for example automated synthesizers by Applied Biosystems Inc., Foster City, Calif.; Beckman; etc. Solution phase synthetic methods may also be used, particularly for large-scale productions.

Peptides may also be present in the form of a salt, generally in a salt form which is pharmaceutically acceptable. These include inorganic salts of sodium, potassium, lithium, ammonium, calcium, magnesium, iron, zinc, copper, manganese, and the like. Various organic salts of the peptide may also be made with, including, but not limited to, acetic acid, propionic acid, pyruvic acid, maleic acid, succinic acid, tartaric acid, citric acid, benozic acid, cinnamic acid, salicylic acid, etc.

The exemplary isolated polypeptides as described herein may cause lysosomal degradation of target proteins. The polypeptides comprise a protein binding domain specific for binding to the target endogenous protein which is desired to be degraded or knocked down, fused to a chaperone mediated autophagy (CMA)-targeting signal (CTS). A CTS is necessary to induce CMA, and is found in all substrate proteins of CMA to date. Numerous examples of CTS's are known in the art, and these are generally biochemically related to the pentapeptide motif KFERQ[7] (SEQ ID NO: 26). The peptides of the invention described in SEQ ID NOs: 1-4 comprise a certain CTS including the KFERQ (SEQ ID NO: 26) motif, however other examples of CTS's are known in the art (for example, Kaushik, S and Cuervo, A. M. Trends in Cell Biology 22(8), 407-17) and thus the peptides of the invention may include alternative CTS domains attached to the protein binding domains, and the identification and replacement of such CTS domains is within the capability of the skilled artisan. The scope of the present invention would thus encompass these peptides comprising alternative CTS domains. As used herein, CMA-targeting signal (CTS) and CMA-targeting motif (CTM) are used interchangeably to refer to the CTS' described above.

The exemplary peptides of the present invention may also be in the soluble form once delivered to the cytosol of a cell where the target protein is located.

The isolated polypeptides may therefore further comprise a delivery and targeting moiety conjugated to the isolated polypeptides to assist in the transportation of the exemplary polypeptides across cell membranes. Optionally, the delivery and targeting moiety may be selected from one or more of: ligands, protein transduction domains, or antibodies. Optionally, the protein transduction domain may be the cell-membrane transduction domain of the HIV-1 Tat protein. The HIV-1 Tat protein may form a fusion protein with the isolated polypeptides described herein (for example, SEQ ID NOs:2 and 4).

Delivery of bioactive molecules, such as the polypeptides or peptides described herein, to a cell or cells in a reasonably efficient manner may require more than just the "dumping" of the naked peptide on to the cell, or administering the naked peptide into the patient or test subject. Agents that enable delivery or targeting of bioactive molecules into cells in a suitable manner so as to provide an effective amount, such as a pharmacologically effective amount are known in the art, and are described in, for e.g.: Dietz et al. (2004). *Mol Cell. Neurosci* 27: 85-131. The peptides or polypeptides described herein may be conjugated to such a cell membrane penetrating domain (CPMD). The term cell membrane penetrating domain (CPMD) as used herein is meant to encompass any moiety that assists in delivering and/or targeting the peptides or polypeptides described herein to a target cell or tissue or within a target cell or within the cells of a target tissue. Furthermore, a cell membrane penetrating domain (CPMD) may "assist" in delivery and/or targeting by virtue of promoting the biological efficacy of the peptides or polypeptides described herein.

Examples of cell membrane penetrating domain (CPMD) may include liposomes, lipid particles, antibodies, receptor ligands, protein transduction domains (PTD), and viral vectors. For example, where delivery to the brain is desired, isolated peptides or polypeptides described herein may be conjugated to antibodies that bind brain endothelial cell receptors resulting in endocytosis/transcytosis of the receptor and bound ligands (for example, U.S. Pat. No. 7,744,879). Peptides or polypeptides may be conjugated to a PTD, for example the HIV TAT protein (trans-activating transcriptional activator protein), which allows peptides to transverse cell membranes via endocytosis.

Examples of PTDs include, but are not limited to: Antennapedia homeodomain (Perez et al. (1992) *J. Cell Sci* 102: 717-722); transportan (Pooga et al. (1998) *FASEB J* 12: 67-77); the translocation domains of diphtheria toxin (Stenmark et al. (1991) *J Cell Biol* 113:1025-1032) and Wiedlocha et al. (1994) *Cell* 76: 1039-1051); and HIV-TAT (Demarchi et al. (1996) *J Virol*. 70: 4427-4437). Other examples and related details of such protein transduction domains are described in Dietz, supra and references cited therein. Furthermore, to reduce peptide degradation during whole body delivery, peptides may be conjugated to small micelles or liposomes using modified PEG, or subject to end-modifications, such as C-terminal amidation or N-terminal acetylation. In addition, the delivery moiety may be a peptide carrier that does not require fusion to the peptide comprising the CTS and PBD, for example the short amphipathic peptide carrier, Pep-1.

A ligand may function as a delivery and targeting moiety by selectively binding or having a specific affinity for another substance. A ligand may be recognized and bound by a specific binding body or binding partner, or receptor. Examples of ligands suitable for targeting may be selected from antigens, haptens, biotin, biotin derivatives, lectins, galactosamine and fucosylamine moieties, receptors, substrates, coenzymes and cofactors among others.

Another type of delivery and targeting moiety is an antibody, which is defined to include all classes of antibodies, including, without limitation: monoclonal antibodies, chimeric antibodies, Fab fractions, fragments and derivatives thereof. Other delivery and targeting moieties may include enzymes, especially cell surface enzymes such as neuraminidases, plasma proteins, avidins, streptavidins, chalones, cavitands, thyroglobulin, intrinsic factor, globulins, chelators, surfactants, organometallic substances, staphylococcal protein A, protein G, cytochromes, lectins, certain resins, and organic polymers.

Delivery and targeting moieties may also include various substances such as any proteins, protein fragments or polypeptides with affinity for the surface of any cells or tissues to be targeted by the peptide or polypeptides described herein. These proteins may be produced through recombinant DNA, genetic and molecular engineering techniques know in the art. For example, SEQ ID NOs:2 and 4 show the isolated polypeptides of SEQ ID NOs:1 and 3 conjugated to the HIV TAT protein. Of particular use would be any suitable membrane transfer proteins to facilitate the transfer of the peptide or polypeptides described herein to the target cell interior (for example, a PTD as described herein).

In certain embodiments, the peptide may further comprise a homing peptide motif to assist in the delivery of the peptide to a specific tissue in vivo. Such homing peptides may include, for example, homing peptides conjugated to CMPDs (such as, AHNP: FCDGFYACYKDV (SEQ ID NO: 27); DV1: lgaswhrpdkcclgyqkrplp (SEQ ID NO: 28); DV3: lgaswhrpdk (SEQ ID NO: 29); PEGA: CPGPEGAGC (SEQ ID NO: 30); and CREKA (SEQ ID NO: 31)) and homing peptides that have cell-penetrating properties themselves (such as, TCP-1: CTPSPFSHC (SEQ ID NO: 32); HAP-1: SFHQFARATLAS (SEQ ID NO: 33); HAP-2: HIQLSPFQSWR (SEQ ID NO: 34); PYEE (SEQ ID NO: 35), LKKP (SEQ ID NO: 36), EPKK* (SEQ ID NO: 37) and ELK*K* (SEQ ID NO: 38) (K*=N-alkyl glycine lysine-like peptoid); F3: CKDEPQRRSARLSAKPAPPKPEPKPK-KAPAKK (SEQ ID NO: 39); Pep42: CTVALPGGYVRVC (SEQ ID NO: 40); CAP: DWRVIIPPRPSA (SEQ ID NO: 41); RGD-4C: CDCRGDCFC (SEQ ID NO: 42); iRGD: CRGDK/RGPD/EC (SEQ ID NOs: 43-46); cRGD: cRGDf (NMeV) (SEQ ID NO: 50); and NGR) (see, for example, Svensen et al., *Trends in Pharmacological Sciences*, 33(4): 186-192, 2012).

As described herein, the exemplary peptides of the present invention comprise a protein binding domain having specificity for a particular target protein or protein-of-interest. Such target protein may be any endogenous, native protein that has a binding partner or for which a binding domain sequence is known or can be obtained. The binding partner or binding domain sequence can be used in the design of the protein binding domain of the peptide. Routine methods known in the art may be used to identify potential binding domain sequences for specific target proteins of interest, such as the yeast two-hybrid method (for example: Protein Kinase C Protocols, Methods in Molecular Biology, Volume 233, 2003, pp 327-343, Detection of Protein Kinase-Binding Partners by the Yeast Two-Hybrid Analysis, Chang and Cartwright), co-immunoprecipitation, in vitro binding assays, protein cross-linking, and blue native gel electrophoresis. Exemplary target proteins are α-synuclein, Post Synaptic Density 95 (PSD 95), death-associated protein kinase 1 (DAPK1), and other protein kinases with peptide binding domains identified (for example, the protein kinases described in Bogoyevitch et al., *Biochimica et Biophysica Acta* 1754: 79-99, 2005).

The protein-binding domain of the exemplary peptides target the peptides to the protein-of-interest. As exemplified below, such protein-binding domains in the exemplary peptides are specific for the target proteins and do not affect non-targeted proteins, thereby demonstrating the reliability and specificity of the exemplary peptides. Accordingly, the exemplary peptides of the present invention are specific for their target proteins, thereby providing a targeted drug delivery mechanism. As further exemplified below, the peptides of the present invention may also be conditional and designed to target only those proteins of interest that are in an active form, rather than an inactive form, thereby increasing the specificity of the exemplary peptides. The ability to target proteins in a diseased form (for example, an active form), rather than a non-diseased form (for example, an inactive form), is a useful therapeutic application of the exemplary peptides.

In therapeutic applications, the compositions described herein may be administered to a subject suffering from one or more symptoms of a disease, for example, a disease associated with cell death and/or apoptosis. The composition described herein may be administered to a subject in an amount sufficient to cure or at least partially prevent or arrest the disease and/or its complications or to help alleviate the symptoms associated therewith. The exemplary peptides and compositions described herein may, therefore, be used as a treatment or as a prophylactic to reduce the risk of a disease or to reduce the symptoms of a disease. An amount adequate to accomplish a treatment, cure or prophylactic treatment is defined as a "therapeutically effective dose" or "a therapeutically effective amount". Amounts effective for this use will depend upon the severity of the disease, the intended use (treatment, cure, prophylactic, alleviation of symptoms, etc.) and the general state of the subject's health. Single or multiple administrations of the compositions may be administered depending on the dosage and frequency as required and tolerated by the patient. A composition generally would provide a sufficient quantity of the active peptide or polypeptides described herein to effectively treat (for example, to at least ameliorate one or more symptoms) in the subject.

The concentration of peptide or polypeptides described herein can vary widely, and may be selected primarily based on fluid volumes, viscosities, body weight and the like in accordance with the particular mode of administration selected and the subject's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages may range from about 20 mg to about 50 mg given orally twice daily. It will be appreciated that such dosages may be varied to optimize a therapeutic regimen in a particular subject or group of subjects.

Therefore, the exemplary peptides of the present invention may be formulated for therapeutic use. Certain exemplary embodiments of the present invention thus relate to pharmaceutical compositions comprising an exemplary peptide of the present invention and a pharmaceutically acceptable carrier, diluent, or excipient. The pharmaceutical compositions can be prepared by known procedures using well-known and readily available ingredients.

In certain embodiments, pharmaceutical compositions comprising the peptide or polypeptides described herein may be formulated for administration orally (including, for example, buccally or sublingually, via a tablet or capsule), topically, parenterally, intranasally, or by inhalation or spray, in unit dosage formulations containing conventional non-toxic pharmaceutically acceptable carriers, adjuvants and vehicles. The term parenteral as used herein includes subcutaneous injections, intraperioneal injections, intradermal, intra-articular, intravenous, intramuscular, intravascular, intrasternal, intrathecal injection or infusion techniques, such as cerebrospinal fluid infusion techniques. The exemplary peptide may be formulated, for example, as a syrup, elixir, tablet, troche, lozenge, hard or soft capsule, pill, oily or aqueous suspension, dispersible powder or granules, emulsion, injectable, or solution.

In some embodiments, the peptide or polypeptides described herein, may be delivered through the skin using conventional transdermal drug delivery systems, i.e., transdermal "patches" wherein the active agent(s) are typically contained within a laminated structure that serves as a peptide or polypeptides delivery device to be affixed to the skin. In such a structure, the composition is typically contained in a layer, or "reservoir", underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In some embodiments, the exemplary peptide or polypeptides described herein may be administered orally. Oral administration of the exemplary peptides may include the use of protective excipients. This is typically accomplished either by complexing the polypeptides with a composition to render it resistant to acidic and enzymatic hydrolysis or by packaging the polypeptides in an appropriately resistant carrier such as a liposome. Means of protecting polypeptides for oral delivery are well known in the art.

Oral administration may be in either solid or fluid unit dosage forms. Fluid unit dosage forms can be prepared according to procedures known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. An elixir is prepared by using a hydroalcoholic (for example, ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Solid formulations such as tablets contain the exemplary peptide in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate: granulating and disintegrating agents for example, corn starch, or alginic acid: binding agents, for example starch, gelatin or acacia, and lubricating agents, for example magnesium stearate, stearic acid or talc and other conventional ingredients such as dicalcium phosphate, magnesium aluminum silicate, calcium sulfate, starch, lactose, methylcellulose, and functionally similar materials. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the exemplary peptide is mixed with an inert solid diluent, for example, calcium carbonate, calcium phosphate or kaolin, or as soft gelatin capsules wherein the exemplary peptide is mixed with water or an oil medium, for example peanut oil, liquid paraffin or olive oil. Soft gelatin capsules are prepared by machine encapsulation of a slurry of the compound with an acceptable vegetable oil, light liquid petrolatum or other inert oil.

Aqueous suspensions contain the exemplary peptide in admixture with excipients suitable for the manufacture of aqueous suspensions. Such excipients are suspending agents, for example sodium carboxylmethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example hepta-decaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl-p-hydroxy benzoate, one or more colouring agents, one or more flavouring agents or one or more sweetening agents, such as sucrose or saccharin.

Oily suspensions may be formulated by suspending the exemplary peptide in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Dispersible powders and granules suitable for preparation of an aqueous suspension by the addition of water provide the exemplary peptide in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions may also be in the form of oil-in-water emulsions. The oil phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

The pharmaceutical compositions may be in the form of a sterile injectable aqueous or oleaginous suspension. This suspension may be formulated according to known art using those suitable dispersing or wetting agents and suspending agents that have been mentioned above. The sterile injectable preparation may also be a sterile injectable solution or a suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Adjuvants such as local anaesthetics, preservatives and buffering agents can also be included in the injectable solution or suspension.

Other pharmaceutical compositions and methods of preparing pharmaceutical compositions are known in the art and are described, for example, in "Remington: The Science and Practice of Pharmacy" (formerly "Remingtons Pharmaceutical Sciences"); Gennaro, A., Lippincott, Williams & Wilkins, Philadelphia, Pa. (2000).

Additional pharmacologically active agents may be delivered along with the primary active agents, e.g., the exemplary peptides or polypeptides described herein. The exemplary peptide or polypeptides may be co-administered with another pharmaceutically active agent to enhance the therapeutic effect on the target cell or tissue by delivering a second compound with a similar or complimentary activity. In one embodiment, such agents include, but are not limited to agents that reduce the risk of a stroke or ischemic injury and/or complications thereof. Such agents include, but are not limited to Anti-coagulants (for example, Acenocoumarol, Coumatetralyl, Dicoumarol, Ethyl biscoumacetate, Phenprocoumon, Warfarin, Clorindione, Diphenadione, Phenindione, Tioclomarol, Bemiparin, Certoparin, Dalteparin, Enoxaparin, Nadroparin, Parnaparin, Reviparin, Tinzaparin, Fondaparinux, Idraparinux, Danaparoid, Sulodexide, Dermatan sulfate, Apixaban, Betrixaban, Edoxaban, Otamixaban, Rivaroxaban, Hirudin, Bivalirudin, Lepirudin, Desirudin, Argatroban, Dabigatran, Melagatran, Ximelagatran, REG1, Defibrotide, Ramatroban, Antithrombin III, and Drotrecogin alfa), Anti-platelet drugs (for example, Abciximab, Eptifibatide, Tirofiban, Clopidogrel, Prasugrel, Ticlopidine, Ticagrel or, Beraprost, Prostacyclin, Iloprost, Treprostinil, Acetylsalicylic acid/Aspirin, Aloxiprin, Carbasalate calcium, Indobufen, Triflusal, Dipyridamole, Picotamide, Terutroban, Cilostazol, Dipyridamole, Triflusal, Cloricromen, Ditazole), and Thrombolytic and Firbrinolytic drugs (for example, tissue plasminogen activator (tPA) or recombinant tissue plasminogen activator (rtPA) such as Alteplase, Reteplase, Tenecteplase, Urokinase, Saruplase, Streptokinase, Anistreplase, Monteplase, Ancrod, Fibrinolysin, and Brinase), and the like or in combination with other neuroprotective agents.

Depending upon their intended use, particularly for administration to mammalian hosts, the subject peptides may also be modified by attachment to other compounds for the purposes of incorporation into carrier molecules, changing peptide bioavailability, extending or shortening half-life, controlling distribution to various tissues or the blood stream, diminishing or enhancing binding to blood components, and the like. The prior examples serve as examples and are expressly non-limiting.

An isolated polynucleotide may comprise a nucleotide sequence encoding an isolated polypeptides as described herein. The compositions described herein may include a polypeptide as described herein and a carrier. Optionally, the carrier may be a pharmaceutically acceptable carrier.

A vector may include an isolated polynucleotide as described herein. A cell may include a vector described herein. Furthermore, a cell comprising the polynucleotide described herein, may have the polynucleotide operably linked to an expression control sequence.

Methods of targeting an endogenous protein for lysosomal degradation are described herein. The methods may involve delivering an isolated polypeptide as described herein to a cell. Such delivery may cause the polypeptide to bind to the target endogenous protein, which may then cause the bound protein to be transported to the lysosome where it is degraded. A method may involve: (a) delivering the vector described herein to the cell; and (b) expressing the polynucleotide carried by the vector. A method may involve: (a) delivering the vector described herein to a cell; and (b) maintaining the cell under conditions permitting expression of the polynucleotide carried by the vector. Optionally, the methods may involve delivering a vector to a cell in an in vivo setting. Optionally, a method may involve delivering the vector to the cell in an ex vivo setting. Optionally, a method may involve delivering the vector to the cell in an in vitro setting.

Certain embodiments of the invention relate to the use of the exemplary peptides described herein to inhibit or reduce the expression of native proteins in a cell in vitro and in vivo. Certain embodiments of the invention further relate to the use of the exemplary peptides described herein to inhibit or reduce the expression of native endogenous proteins in a cell in vitro and in vivo.

Another exemplary embodiment of the invention relates to the use of the exemplary peptides described herein to treat disease.

'Excitotoxic stress' as used herein is an important component of disorders such as stroke and other neurodegenerative diseases. There is evidence that the toxic effects of excitotoxic stress may be exerted through mechanisms that result in both acute and delayed forms of cell death, when receptors for the excitatory neurotransmitter glutamate (glutamate receptors) such as the NMDA receptor and AMPA receptor are overactivated. Excitotoxins like NMDA and kainic acid which bind to these receptors, as well as pathologically high levels of glutamate, can cause excitotoxicity by allowing high levels of calcium ions (Ca2+) to enter the cell. Ca' influx into cells can activate a number of enzymes, including phospholipases, endonucleases, and proteases such as calpain. These enzymes are capable of damaging cell structures like the cytoskeleton, cell membranes, and DNA. Excitotoxicity may be involved in spinal cord injury, stroke, traumatic brain injury, alcoholism or alcohol withdrawal, and neurodegenerative diseases of the central nervous system (CNS) such as multiple sclerosis, Alzheimer's disease, amyotrophic lateral sclerosis (ALS), Parkinson's disease, and Huntington's disease.

Therefore, certain embodiments of the invention contemplate the therapeutic use of the peptides described herein to treat pathological conditions, such as neurodegenerative diseases of the central nervous system (CNS), including multiple sclerosis, Alzheimer's disease, amyotrophic lateral sclerosis (ALS), Parkinson's disease, and Huntington's disease, or to treat spinal cord injury, stroke, traumatic brain injury, alcoholism and alcohol withdrawal.

An exemplary embodiment of the present invention therefore also relates to a method of treating a disease associated with cell death and/or apoptosis. The method may comprise: administering a biologically effective amount of the polypeptides described herein or the pharmaceutical compositions described herein to a subject in need thereof. The biologically effective amount may be an amount sufficient to prevent cell death and/or apoptosis. The disease associated with cell death and/or apoptosis may be selected from the following without limitation: amyotrophic lateral sclerosis (ALS), frontotemporal lobe dementia, stroke, multiple sclerosis, Alzheimer's disease, Parkinson's disease, Huntington's disease, spinal cord injury, traumatic brain injury, alcoholism or alcohol withdrawal.

WORKING EXAMPLES

Materials and Methods

General antibodies and reagents. Anti-GFP (Clontech, 632381), anti-α-synuclein (BD Transduction Laboratories, 610786), Monoclonal anti-FLAG M2 antibody (Sigma-Aldrich, F1804-200UG), anti-DAPK1 (Sigma, D1803-200UL), Monoclonal anti-phospho-DAPK1 (pSer308, Sigma, D4941), anti-NR2B (lab generated), anti-HA (Roche applied science, 11867431001), anti-lamp1 (Abcam, ab13523), anti-GAPDH (Abcam, ab9485), anti-actin (Abcam, ab8227), anti-lamp2a (Abcam, ab18528), anti-Labmin B1 (Abcam, ab16048), anti-HSP90 (BD Transduction Laboratories, 610418), anti-VDAC1 (Porin) (MitoSciences, MSA03). Antibodies were validated for their intended purpose (immunoblotting, immunocytochemistry, immunohistochemistry and co-immunoprecipitation), in accordance with the manufacturer's product sheet and/or laboratory procedures. Ammonium chloride (Sigma, A0171), 3-methyladenine (Sigma, M9281), MG132 (Sigma, C2211), Pepstatin A (Sigma), N-Methyl-D-aspartic acid (NMDA, Tocris Asc-052), $H_2O_2$ (Sigma, 7722-84-1), Catalase (Sigma, C1345), (2R)-amino-5-phosphonopentanoic acid (APV, Ascent Scientific, Asc-003). TAT-NR2B-CTS and TAT-NR2B was synthesized by GL Biochem and Brain Research Center peptide synthesis facility at UBC.

Plasmid construction. CTS-GFP was constructed by introducing a BamHI fragment containing the CTS coding sequence into the pEGFP-N2 vector (Clontech #6081-1). The CTS coding sequence was prepared by annealing custom design oligonucleotides (Integrated DNA Technologies). mCTS-GFP was constructed by performing single point mutations to CTS-GFP plasmid. FLAG-βsyn36 was constructed by annealing oligonucleotides and inserting into pcDNA3.0 using HindIII and NotI restriction sites (HindIII, Fermentas, FD0504; NotI Fermentas, FD0594). FLAG-βsyn36-CTS was constructed by PCR using FLAG-βsyn36 as template and adding CTS coding sequence to the reverse primer. FLAG-cDAPK1 was constructed by deleting the autoinhibitory domain from WT-DAPK1 (789-936 bp). NR2Bct (1242-1342aa) was prepared by PCR using NR2B expression vector. NR2Bct-CTS fragment was obtained by inserting NR2Bct fragment into CTS-GFP using EcoRI and BglII restriction sites (EcoRI, Fermentas, FD0274; BglII, Fermentas, FD0084), then PCR, introducing NcoI and EcoRI to the fragment (NcoI, Fermentas, FD0574). His-TAT-NR2Bct-CTS was constructed by cloning NR2Bct-CTS into the pTAT/pTAT-HA plasmids (generous gift of S. Dowdy, Washington University, St. Louis, Mo.[31]) using NcoI and EcoRI restriction sites. His-TAT-NR2Bct was constructed by mutating the first amino acid in CTS sequence into a stop codon. HA-NR2Bct-CTS was constructed by PCR using His-TAT-NR2Bct-CTS as template, with BamHI site in both forward and reverse primers, and then inserted into pcDNA3.0 with BamHI (Fermentas, FERFD0054). HA-NR2Bct-CTSm was constructed by point mutations.

His peptide purification. His-TAT-NR2Bct and His-TAT-NR2Bct-CTS plasmids were transformed into BL21, plated onto Amp resilient plates and incubated overnight at 37° C. Single colony from each plasmid was resuspended in LB(Amp+) and incubated at 37° C. until $OD_{600}$ reached 0.5. Expression was induced by adding IPTG (1 mM) and incubating for 5 hours. Pellets were then collected by centrifugation and discarding the medium. Pellets were sonicated and centrifuged before purification. His peptide purification was done according to the manufacturer's protocols (Thermo Scientific, 88223). Briefly, Ni-NTA resin columns were equilibrated before prepared peptide extracts were added to the resin. The columns were then washed before eluted using elution buffer. The purified peptides were then monitored for purity using Coomassie staining, and peptide concentration measured by absorbance at 280 nm.

Cell culture, transfection and treatments. HEK293 cells and COS7 cells were cultured in DMEM (Sigma, D6429-24X500ML) supplemented with 10% Fetal Bovine Serum (Invitrogen, 12483020). Cells were grown to 80% confluence in 6-well plates before transiently transfected with Lipofectamine 2000 (Invitrogen, 11668019), as according to the manufacturer's protocols. Cells were transfected for either 24 or 48 hours at 37° C. before harvesting for biochemical analyses. For experiments involving TAT or His-TAT peptides, unless otherwise specified, peptides were added 1 hour prior to NMDA insult.

Primary culture of cortical neurons. Dissociated cultures of rat cortical neurons were prepared from Sprague Dawley rat embryos collected from euthanized mothers 18 days after fertilization as previously described[35]. Briefly, hippocampi and cerebral cortices were extracted from embryos and incubated for 30 min in 0.25% trypsin-EDTA. Digested tissues were dissociated by trituration and plated on poly-D-lysine-coated (Sigma, P7280) plates. Plating medium consisted of Neurobasal Media (Invitrogen, 21103-049) supplemented with B27 (Invitrogen, 17504044), glutamic acid (Sigma, G8415) and GlutaMax (Invitrogen, 35050-061). After 2 days, ⅔ of the media was replaced with fresh Neurobasal feeding media consisting of Neurobasal Media, B27 and GlutaMax. Cultures were maintained at 37° C. in a humidified 5% $CO_2$ atmosphere. Mature neurons (14-18 days in vitro (DIV)) were used for experiments.

Immunoblotting. Immunoblotting assays were carried out as previously described[36]. Briefly, proteins were extracted from neurons using a lysis buffer composed of 150 mM NaCl, 50 mM Tris, pH 7.4, 0.1% SDS, 1% NP-40, 0.5% sodium deoxycholate, 1 mM EDTA, 1 mM $Na_3VO_4$, and proteinase inhibitor mixture (Thermo Fisher, PI78442). Samples were separated on 10% SDS-PAGE gels, transferred to polyvinylidene difluoride (PVDF) membrane, and immunoblotted with respective antibodies. Blots were enhanced with chemiluminescence detection reagent kit (Fisher, 32106) and visualized with Bio-Rad imager and Quantity One software. Signal intensities from each band was quantified with Bio-Rad Image Lab software, and the bands were analyzed relative to their controls from the same membrane and experiment.

Co-immunoprecipitation. Co-immunoprecipitation (Co-IP) assays were performed as previously described with minor modifications[37]. Cortical neuronal cultures lysed in ice-cold lysis buffer without SDS. The extracts (0.5 mg) were pre-cleared for 1 hour with 10 μl Protein A-sepharose beads (GE Life Sciences, 17-0780-01), then incubated with nonspecific IgG (4 μg), polyclonal anti-NR2B (lab, 4 μg) overnight at 4° C., followed by addition of 60 ul Protein A-sepharose beads (Sigma) for 3 hours at 4° C. Samples were washed two times with lysis buffer, two times with sterile PBS and denatured with SDS sample buffer. SDS-PAGE and immunoblotting were subsequently performed as described above.

Immunocytochemistry. Immunocytochemistry was carried out as previously described[37]. COS cells were washed with ice-cold PBS, then fixed in pre-warmed 4% PFA/PBS solution at 37° C. for 60 min, permeabilized in 0.1% Triton X-100 for 5 min, and blocked with 5% fetal bovine serum (FBS) in PBS for 30 min at 37° C. with extensive PBS washings between each step. Primary antibodies were diluted in 3% FBS. Cells were incubated with anti-lampla (1:50) for 24-48 hours at 4° C., then washed 6×2 min with PBS. Secondary antibody Alexa 555 was diluted in 3% FBS/PBS at 1:1000 and incubated for 30 min at 37° C. and then washed extensively. Nuclei was stained with DAPI (1:5000, 10 min RT) prior to mounting on slides in ProLong Gold medium (Invitrogen, P36930). Captured images were obtained from a confocal microscope (Leica DMIRE2 & CTRMIC). Representative images have been adjusted to maximize the signal:noise ratio.

Cellular fractionation. Cytoplasm/nuclei fractionation was performed on cultured cortical neurons ($6.0*10^6$ cells/100 mm dish). Briefly, cells were washed with ice cold PBS and rocked in lysis buffer for 30 min. Cells were then collected and centrifuged to obtain a rough cytoplasmic and nuclear fraction. Supernatant was collected and further centrifuged to obtain purified cytosolic fraction. The original pellet was washed and vortexed to obtain a nuclear lysis. Mitochondrial fractionation was performed as described in the Pierce Mitochondria Isolation Kit for Cultured Cells (Thermo Scientific, 89874) user guide. Purity was assessed by immunoblotting for the presence of LB1 (nucleus only), HSP90 (cytosol only) and VDAC1 (mitochondria only).

Assessment of neuronal death. Cytotoxic damage of primary neuron cultures was assessed by measuring LDH released into culture media as previously described[38]. Cortical neurons were exposed to $H_2O_2$-induced excitotoxicity (300 μM for 30 min) in the presence and absence of His-TAT-NR2Bct-CTS, control peptide His-TAT-NR2Bct (50 μM, 1 hour pretreatment and throughout the experiment), APV (1 mM, 30 min pretreatment and throughout experiment) or catalase (100U, 15 min pretreatment and throughout experiment), their culture media were collected 12 hours post insult for LDH enzymatic activity. Peptide toxicity was assessed by treating neurons with 25 μM synthetic peptide or 200 μM recombinant peptide for 24 hrs. Media was collected for LDH assay. Positive control was obtained by lysing the cells with 100% Trixton X-100 prior media collection. The amount of LDH in the medium was determined using a LDH cytotoxicity detection kit (Sigma, TOX7) according to the manufacturer's instructions. The absorbance at 490 nm was determined using a microplate reader (μQuant, Bio-TEK instruments), which was adjusted by background reading deduction.

Middle cerebral arterial occlusion (MCAO). All animal experiments were performed according to protocols approved by the University of British Columbia Committee on Animal Care. Adult naïve male Sprague-Dawley rats (300-350 g, Charles River) were group housed (3-4 animals/cage) in 12 hr:12 hr light-dark cycles and had free access to rat pellet chow and water prior to surgery. Reversible MCAO with suture-insertion method was performed as described previously[37]. Briefly, a nylon suture with a blunted tip was entered through the right external carotid artery of anesthetized rats and advanced to the right internal carotid artery until the right MCA was occluded. After 60 min of occlusion, the rat was reanesthetized to facilitate the removal of the occlusion. Body temperature was maintained at between 36.5 and 37.5° C. throughout the surgical procedure with a heating pad. Peptides (10 mg/kg) or vehicle control (saline; 1 ml/kg) was injected via the jugular vein. Rats were then sewn up and allowed to recover until tissue collection.

Immunohistochemistry. Rats were anesthetized and perfused with double-filtered saline and 4% paraformaldehyde (PFA) in PBS. Brains were collected, immersed in 4% PFA before subjected to cryoprotection by 30% sucrose/PBS. After the brains had sunk, they were flash frozen with dry ice before overnight freezing in −80° C. They were then sliced at 30 μm with a cryostat, and stored in 0.1M PB (sodium phosphate dibasic and sodium phosphate monobasic). Prior to staining, slices were washed 3×10 min with 0.1M PB, permeablized and blocked in 0.1M PB with 1% BSA and 0.2% Triton X-100 for 30 min, and stained with anti-DAPK1 (1:100) at 4° C. for 3 days. They were then washed and stained with Alexa 488 (1:1000) at 4° C. overnight before washing and mounting.

Hematoxylin & Eosin (H&E) staining. Slices were mounted and dried on glass slides prior staining. Slides were immersed in Hematoxylin solution (Sigma, MHS1-100ML) for 15 min away from light, followed by 5 min blueing under tap water. Slides were then counterstained with 0.5% Eosin Y (Sigma, E4009-5G) and dipped in $ddH_2O$ until the eosin stopped streaking. They were then dehydrated with EtOH (50%, 70%, 95% and 100%) and cleared 2 times with Xylene. Permount (Fischer Scientific, SP15-500) was used for coverslips.

Statistical analyses. Data are expressed as means±s.e.m. Quantifications were conducted using at least three independent experiments. Statistical significance was defined as * or $^{\Delta}$ P<0.05,  or $^{\Delta\Delta}$ P<0.01, * or $^{\Delta\Delta\Delta}$ p<0.001. ANOVA (Fischer LSD method) was used unless otherwise specified. One way ANOVA (Fischer LSD method) was used unless otherwise specified, data was tested for normality (Shapiro-Wilk test, power 0.05) and equal variance (power 0.05) prior commencing ANOVA analysis.

Results/Discussion

As illustrated in FIG. 1a, we designed a targeting peptide comprising a cell membrane penetrating domain (CMPD), a protein binding domain (PBD) that has specification for a target protein and a CMA-targeting signal (CTS) or CMA-targeting motif (CTM). As used herein, "CTS" and "CTM" in the exemplary peptides are used interchangeably. When a targeting peptide of the present invention (as illustrated in FIG. 1a) is applied to a cellular environment in vitro or in vivo, the targeting peptide enters the cells via its CMPD, where it forms a stable complex with its target protein via the PBD, and through the interaction between its CTS with cytosolic heat shock chaperone (hsc)70 and various co-chaperones[8], delivers the target protein into the lysosomal compartments for rapid knock-down via CMA-mediated protein degradation.

CTS targeting of proteins to lysosomes for degradation. Using HEK cells, we showed that the CTS can efficiently direct a CTS-containing protein into the lysosome for degradation by fusing the CTS to Green Fluorescent Protein (GFP) at its amino terminal (CTS-GFP). To increase targeting efficiency, we simultaneously tagged GFP with three different CMA targeting signals identified from three different CMA substrate proteins—Rnase A (KFERQ)[9] (SEQ ID NO: 47), hsc70 (QKILD)[10] (SEQ ID NO: 48) and hemoglobin (QRFFE)[11] (SEQ ID NO: 49) (FIG. 1b). We then transiently expressed the CTS-GFP construct, along with a non-CTS-tagged wild type GFP construct (WT-GFP) as a control, in HEK or COS-7 cells. As shown in FIG. 1c, co-immunofluorescent staining revealed that while WT-GFP was diffusely expressed in most compartments of the cell including the nucleus, CTS-GFP was predominantly directed into the lysomomal compartment, as evidenced by its high degree of co-localization with lysosome marker protein lamp1 a. Consistent with the ability of the CTS to direct CTS-GFP for lysosomal degradation, immunoblot analysis showed that CTS-GFP protein levels were decreased in a time-dependent manner, decreasing by 47.97%±5.66% (mean±s.e.m.) of the WT-GFP levels 24 hours after transfection. (Suppl. FIG. 1).

Figure 6:
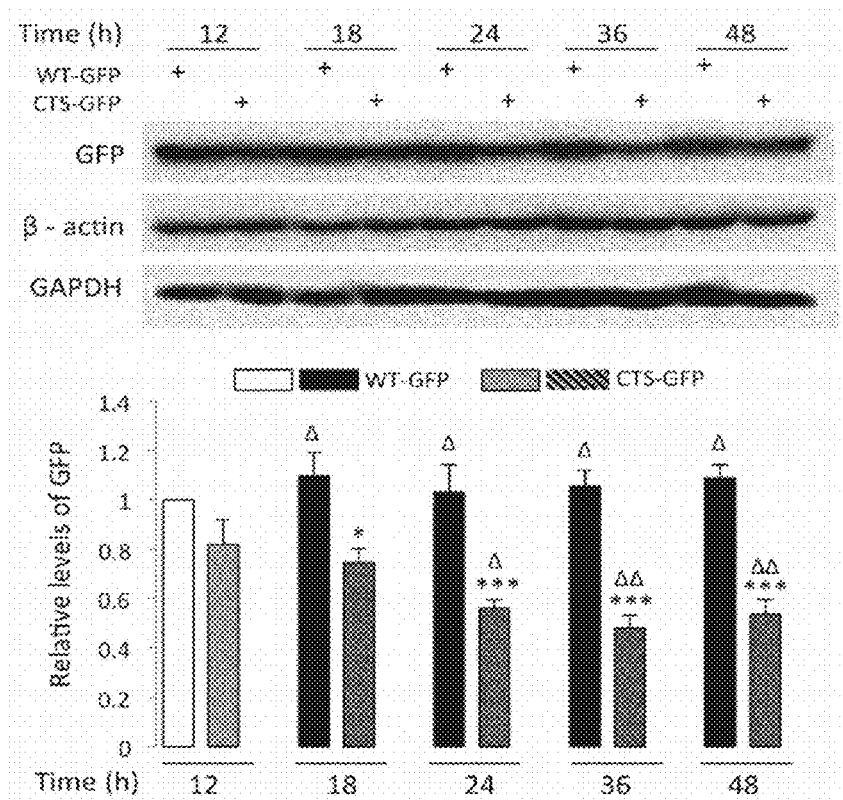
FIG. 6. CTS-GFP is degraded in a time-dependent manner, while endogenous CMA-substrate GAPDH remains stable in COST cells transiently transfected with CTS-GFP. Bars represent protein levels normalized to 12 hr WT-GFP group (white bar), and compared to 12 hr WT-GFP group (white bar, *) or 12 hr CTS-GFP group (grey bar, Δ) *,Δp<0.05, ,$^{ΔΔ}$p<0.01 and *,$^{ΔΔΔ}$p<0.001, bars represent relative mean values±s.e.m.

Several lines of evidence indicate that the reduction of CTS-GFP levels is a result of increased lysosomal targeting and degradation. First, the reduction in CTS-GFP levels was fully prevented by treatment with the lysosomal degradation inhibitor ammonium chloride[12] ($NH_4Cl$; 20 mM; 82.65%±6.28%; n=6; p=0.001 compared with non-treated CTS-GFP group) or pepstatin A (Pep A), an inhibitor of the two primary lysosomal proteases, cathepsins A and E[13,14] (Pep A; 10 µM; 106.98%±6.68%; n=5; p=0.001, compared with non-treated CTS-GFP group) (FIG. 1d). In contrast, inhibition of other protein degradation systems, such as macroautophagy with 3-methyladenine (3-MA; 10 mM) or proteasomal degradation with MG132 (MG132; 5 µM), did not prevent the reduction in CTS-GFP levels (being respectively reduced in 3-MA and MG132 groups to 51.61%±6.09% and 42.55%±3.78% of wild type GFP levels; n=6 in each group; p=0.610 and p=0.213 for 3-MA and MG132, respectively, compared to untreated CTS-GFP group) (FIG. 1d). Second, CMA can be activated or enhanced under conditions of stress, such as starvation induced by removal of serum in culture media[15]. Indeed, serum deprivation (SD) caused a further decrease in the levels of CTS-GFP (SD; 23.95%±5.94% of WT-GFP level; n=5; p=0.0001 compared with the WT-GFP) (FIG. 1d). Third, mutation of the glutamine residue (Q) in the CTS of CMA substrate proteins impairs the association of mutant proteins with lysosomal membrane and thereby reduces their targeting into the lysosomal lumen and degradation through CMA[16]. Consistently, we found that mutation of the 2Qs into alanines (2A) within the CTS of CTS-GFP (mCTS-GFP) prevented the reduction of mCTS-GFP levels (FIG. 1d; mCTS-GFP; 94.87%±7.82% of WT-GFP; n=9; p=0.990, compared with WT-GFP). This result confirms the necessary role of CTS in specifically directing the CTS-tagged GFP for lysosomal degradation. Finally, overexpressing CTS-GFP did not significantly alter the stability of the endogenous CMA substrate glyceraldehyde 3-phosphate dehydrogenase (GAPDH)[17] (FIG. 6), suggesting that the CTS in the CTS-GFP only specifically increase the lysosomal degradation of the CTS-tagged GFP, instead of generally increasing CMA activity in the transfected cells. Together, these experiments show that the addition of CTS to a non-CMA substrate protein is sufficient to specifically channel the protein for degradation through the CMA pathway.

Indirect targeting of DAPK1 to lysosome using a peptide comprising CTS and binding domain having specificity for DAPK1. Having confirmed the efficiency and specificity of CTS in targeting CTS-fused protein for lysosomal degradation, we proceeded to demonstrate that a non-CMA protein substrate can be indirectly tagged for CMA-mediated lysosomal degradation using a short peptide composed of the CTS and a binding domain to the target protein.

Figure 2B:
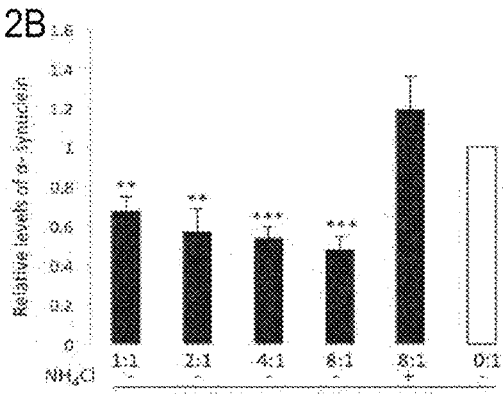
Figure 2C:
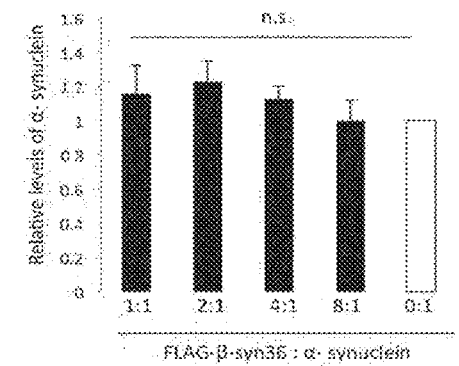
Figure 2D:
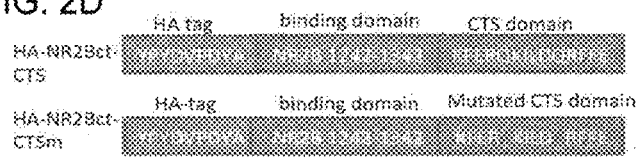

Death-associated protein kinase 1 (DAPK1) is a calcium-calmodulin regulated protein kinase normally inactive in the brain. When inactive, DAPK1 does not interact with the N-methyl-D-aspartate (NMDA) receptor NR2B subunit[20]. However, under certain pathological conditions such as excitotoxic stimulation with NMDA or cerebral ischemia[20], DAPK1 can be activated and recruited into NMDA receptor complexes by its interaction with the C-terminal (CT) residues 1292-1304 of the NR2B subunit (NR2Bct$_{1292-1304}$)[20]. Because NR2B can only bind to the active, but not inactive form of DAPK1, we showed that a peptide containing the DAPK1 binding sequence of NR2B and CTS can conditionally target the active (but not inactive) form of DAPK1 for CMA-mediated lysosomal degradation. Two NR2B carboxyl tail constructs bearing an HA tag were designed, the CT fragment of NR2B (NR2Bct$_{1242-1342}$) containing the 100 amino acid sequence for binding to DAPK1 and either a functional (HA-NR2Bct-CTS) or a non-functional mutated CTS (HA-NR2Bct-CTSm) (FIG. 2d).

Figure 2E:
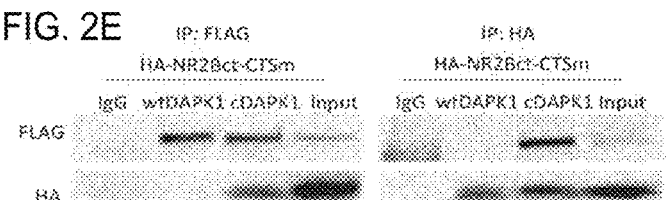

The HA-NR2Bct-CTSm (which cannot be degraded by the lysosomal system) was co-expressed in HEK cells with either a Flag-tagged constitutively active form of DAPK1 (cDAPK1)[21] or wild-type DAPK1 (wtDAPK1) to demonstrate that the peptide can sufficiently and specifically bind to the active form of DAPK1 via the interaction between NR2Bct and active DAPK1. Reciprocal co-immunoprecipitation experiments with either anti-Flag or HA were performed. As shown in FIG. 2e, co-immunoprecipitation experiments revealed the interaction of HA-NR2Bct-CTSm with cDAPK1, but not wtDAPK1, confirming previous results that NR2B and DAPK1 binding is conditionally dependent on the activation of the latter[20].

Figure 2G:
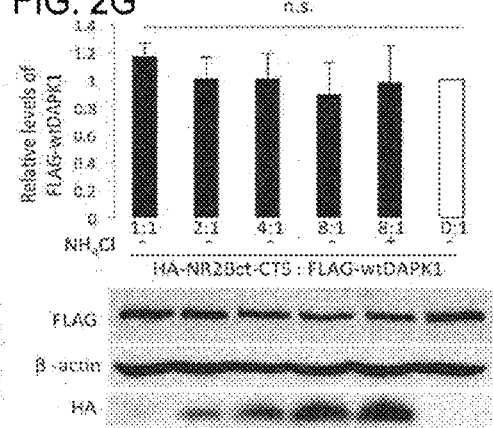
Figure 2F:
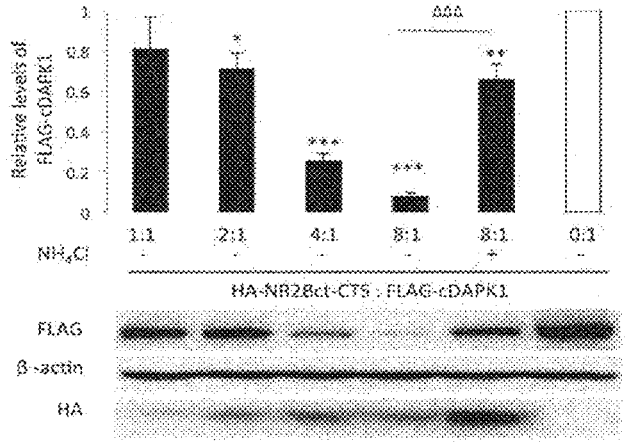
Figure 2H:
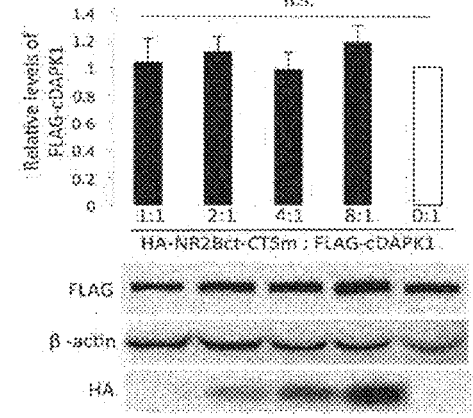

Consistent with the specific interaction between NR2Bct and cDAPK1, but not wtDAPK1, co-expression of HA-NR2Bct-CTS at various ratios efficiently decreased the levels of cDAPK1 in a dose-dependent manner, 24 hours after transfection (FIG. 2f). At a 1:2 transfection ratio, the levels of cDAPK1 were decreased by 29.18±1.91% of cDAPK1 transfected alone (n=4; p=0.021 compared to that of cDAPK1 expressed alone (0:1, white bar)), whereas at 8:1, the levels of cDAPK1 were reduced by 92.85%±2.30% (n=4; p=0.001, compared to that of cDAPK1 expressed alone (0:1, white bar)). In contrast, co-expression of the HA-NR2Bct-CTS even at the highest ratio (8:1) with wtDAPK1 did not significantly affect the expression levels of wtDAPK1 (FIG. 2g; n=3; p=0.933), strongly suggesting that the ability of the peptide to interact with DAPK1 is required for the peptide-induced reduction of cDAPK1. The HA-NR2Bct-CTS-induced reduction of cDAPK1 appears to be mediated by increased lysosomal degradation, as it was significantly prevented by lysosomal inhibitor $NH_4Cl$ (FIG. 2f; n=4) or by mutating CTS within the peptide (FIG. 2h; HA-NR2Bct-CTSm; n=8). Taken together, these data suggest that the specific reduction of cDAPK1 is due to increased lysosomal degradation, and that this is dependent on both the peptide-protein interaction and functional CTS of the peptide.

Therefore, an exemplary embodiment of the present invention is the indirect tagging of a non-CMA substrate protein, i.e., DAPK1, using a CTS containing protein-binding peptide that can effectively target the protein for lysosomal degradation, thereby representing a new method for a rapid reduction of the expression levels of a protein in a cell.

Targeted peptide-mediated reduction of endogenous DAPK1 levels in primary neuronal cultures. Cultured cortical neurons were used to illustrate the use of an exemplary embodiment of the peptide-mediated system of the present invention in efficiently reducing the expression level of an endogenous protein, DAPK1, in primary cells in situ.

Figure 7F:
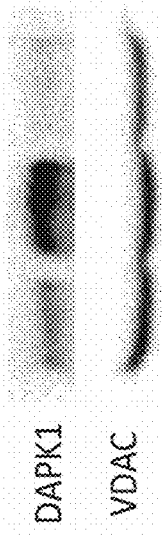
FIG. 7(a-f). TAT-NR2BCTM-induced degradation of DAPK1 reduces DAPK1 levels in various subcellular compartments in neuron cultures. (a-c) Immunoblotting of various subcellular fractions showing that NMDA treatments (50 μM, 30 min) produce a time-dependent translocation of DAPK1 from the (a) nuclear fraction (Nucleus; Left panels) to the (b) cytosolic (Cytosol; Middle panels) and (c) mitochondrial (Mitochondria; Right panels) fractions. β-actin was used as a loading control. LB1, HSP90 and VDAC were used as loading control for nuclear, cytosol and mitochondrial fractions, respectively. After treatment with NMDA, DAPK1 levels were significantly decreased in the nucleus (left; n=4; p<0.001, F(5,18)=12.349) at 2 hrs, which continued up to 8 hours. Conversely, DAPK1 levels significantly increased in the cytosol (middle; n=4; p=0.034, F(5,18)=3.112) at 4 hours and returned to baseline at 8 hours, while DAPK1 immediately increased in the mitochondria (right; n=5; p=0.020, F(5,20)=3.499) post NMDA-washout, which persisted up to 6 hours after NMDA washout. (d-f) Bath applications of TAT-NR2BCTM (25 μM, 1 hr prior to and during NMDA treatment) significantly decreased DAPK1 in (d) nuclear (left, n=4, p<0.001, F(2, 9)=19.139), (e) cytosolic (middle, n=4, p=0.006, F(2,8)=10.417) and (f) mitochondrial (right, n=4, p<0.001, F(2,9)=18.597) subcellular fractions 2 hours after NMDA treatment and washout, as compared to naïve control and NMDA-treated group (grey bar). One way ANOVA with Tukey post-hoc was used. *compared to control, Δ compared to NMDA-treated group (grey bar). *,Δp<0.05, ,ΔΔp<0.01; *,ΔΔΔp<0.001 bars represent relative mean values±s.e.m. normalized to the naïve non-treated control (arbitrarily set as 1).
Figure 7E:
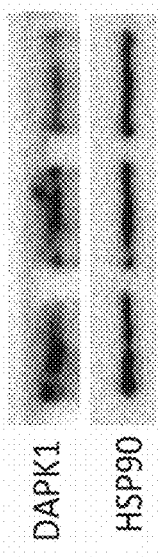
Figure 7D:
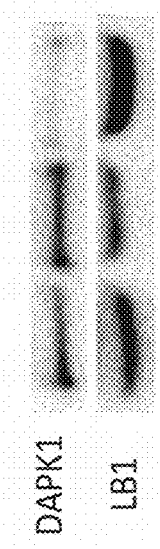

We first showed, as previously reported[20], that NR2B can interact with the activated, but not inactivated, DAPK1 in cultured cortical neurons under our experimental conditions. We activated DAPK1 in cultured cortical neurons by treating the neurons with 50 μM NMDA for 30 min as previously described[20]. As shown by the immunoblots in FIG. 3a, NMDA treatment resulted in a significant activation of DAPK1, as evidenced by the decrease in the level of the phosphorylated form of DAPK1[20]. In addition, there was a notable reduction in the total amount of DAPK1 following NMDA treatment, consistent with a previous report[22]. On the subcellular level, NMDA stimulation of DAPK1 resulted in increased levels of DAPK1 in the mitochondria and cytosol, and decreased levels in the nucleus (FIG. 7a). Co-immunoprecipitation experiments further revealed that while there was no obvious association between NR2B and DAPK1 under basal conditions, NMDA treatment resulted in complex formation between the two proteins (FIG. 3b). These results therefore demonstrate that, similar to previous studies[20], NMDA receptor activation not only activates DAPK1, but also recruits the active DAPK1 to NR2B-containing NMDA receptors in the cultured cortical neurons.

Given this activity-dependent association between NR2B and DAPK1, we then showed that the NR2Bct-CTS peptide described above could be used to reduce the intracellular expression levels of DAPK1 in a NMDA stimulation (excitotoxicity)-dependent manner. We subcloned the NR2Bct-CTS or NR2Bct without CTS, along with the cell membrane-penetrating sequence TAT (to render the constructs plasma membrane permeable), into bacterial expression vectors, and then expressed and purified them as His-tagged recombinant peptides (TAT-NR2Bct-CTS and TAT-NR2Bct; FIG. 3b). As shown in FIG. 3c, bath application of TAT-NR2Bct-CTS (200 μM; 90 min; n=4; p=0.47) produced no observable effect on the basal level of DAPK1 on its own. However, when co-applied with NMDA, TAT-NR2Bct-CTS (200 μM; 60 min prior to and during 30 min NMDA treatment) decreased the level of DAPK1 by 57.50%±6.70% 2 hours after NMDA washout (n=9; p=0.007, compared to NMDA-treated group in the absence of TAT-NR2Bct-CTS; FIG. 3c). In contrast, co-application of the same amount of control peptide TAT-NR2Bct (i.e., without CTS) with NMDA did not produce any notable reduction of DAPK1 relative to NMDA treatment alone (n=6; p=0.897 compared to NMDA alone-treated group; FIG. 3c). TAT-NR2Bct-CTS-mediated reduction of DAPK1 expression levels was rescued by the lysosome inhibitor NH$_4$Cl (n=5; p=0.118 compared to NMDA-treated group). These results strongly suggest that the observed decrease in DAPK1 is mediated by lysosomal degradation, and that it requires the specific interaction of NR2Bct with the activated DAPK1 and the presence of the CTS in the targeting peptide.

As described below, an exemplary embodiment of the present invention is a dose-dependent and time-dependent conditional knock-down of active DAPK1 TAT-NR2Bct-CTS. As shown in FIG. 3d, following NMDA stimulation, increasing TAT-NR2Bct-CTS from 25 μM to 200 μM produced a dose-dependent DAPK1 degradation. Furthermore, a single dose of TAT-NR2Bct-CTS (200 μM; 60 min prior to, and 30 min during NMDA stimulation) resulted in a time-dependent reduction in DAPK1 levels, which became significant by 2 hours (n=6; p=0.018 compared to 0 hr group), peaked at 4 hours (n=6; p=0.001 compared to 0 hr group), and then gradually returned to baseline levels within 7 hours post-treatment (FIG. 3e). However, administrating a second dose of His-TAT-NR2Bct-CTS immediately after NMDA washout allowed DAPK1 degradation to persist up to 7 hours of observation period (FIG. 3f; n=4; p=0.002 compared to NMDA-treated group). The reversibility and time-dependency of the reduction of DAPK1 levels strongly support the supposition that the reduction is not due to non-specific cellular processes, such as toxicity-induced cell death, but is a result of TAT-NR2Bct-CTS mediated rapid and reversible degradation of its target protein. As shown, the degree and time course of the reduction can also be easily controlled by varying the concentrations and/or times of the peptide application.

Figure 4A:
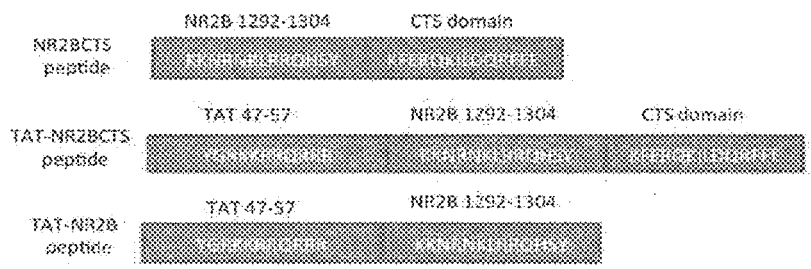
FIG. 4(a-e). Intracellular delivery of short synthetic NR2B-CTS peptides specifically knocks down active native DAPK1 in cultured neurons. (a) Schematic illustration of synthetic peptides NR2B-CTS, TAT-NR2B and TAT-NR2B-CTS. Sequences in FIG. 4a: KKNRNKLRRQHSY (SEQ ID NO:58), KFERQKILDQRFFE (SEQ ID NO:53), YGRKKRRQRRR (SEQ ID NO:57), KKNRNKLRRQHSYKFERQKILDQRFFE (SEQ ID NO:3), YGRKKRRQRRRKKNRNKLRRQHSYKFERQKILDQRFFE (SEQ ID NO:4), and YGRKKRRQRRRKKNRNKLRRQHSY (SEQ ID NO:59). (b-e) NR2B-CTS, when delivered into cortical neurons, specifically decreases the level of native DAPK1 in an NMDA-stimulation dependent manner. NR2B-CTS was mixed with intracellular delivering carrier peptide Pep-1 at a 1:4 ratio for 30 min to form a plasma membrane permeable peptide complex and the complex was then bath applied into neurons 60 min prior to and during NMDA treatments (50 μM; 30 min). Levels of DAPK1 were determined by the quantification of immunoblots in each bar graph and corresponding representative immunoblots were given below the bars. Bars represent relative DAPK1 levels normalized to non-treated naïve group (white bar, arbitrarily set as 1), and compared to both naïve (white bar, *) or NMDA-treated group (grey bar, $^Δ$). Membrane-probing for β-actin was used as loading control. NR2B-CTS plus Pep-1 (but not the Pep-1 alone) dose- (b; n=5), and time-dependently (c; n=4) decreased the level of endogenous DAPK1 in cultured cortical neurons following NMDA treatment. The reduction required NMDA stimulation (b) and was rescued by inhibiting lysosome function with $NH_4Cl$ (d; $NH_4Cl$ 20 mM; n=8; p=0.118 compared to NMDA-treated group). (e) The synthetic cell-penetrating peptide TAT-NR2B-CTS (25 μM; n=6; p=0.001, compared to NMDA-treated group), but not the CTS-lacking control TAT-NR2B (25 μM; n=4; p=0.223 compared to NMDA-treated group), decreased native DAPK1 and this reduction was prevented by in the presence of lysosomal inhibitor $NH_4Cl$ (20 mM; n=5; p=0.302, compared to NMDA-treated group).
Figure 4B:
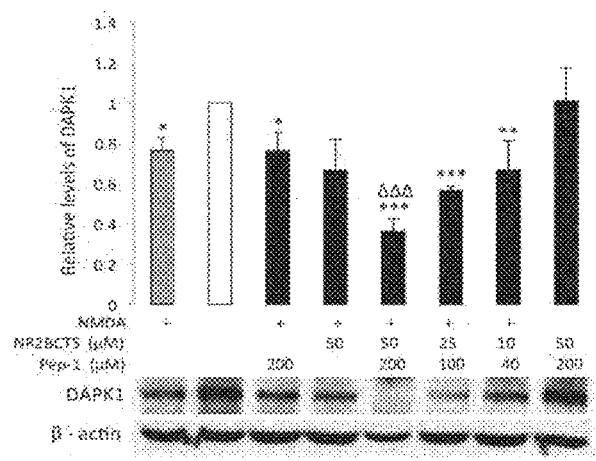
Figure 4C:
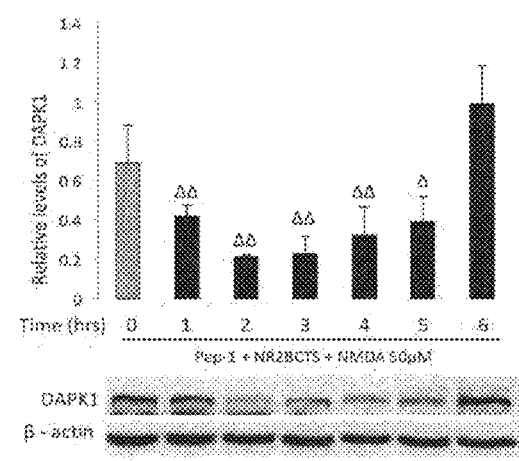
Figure 4D:
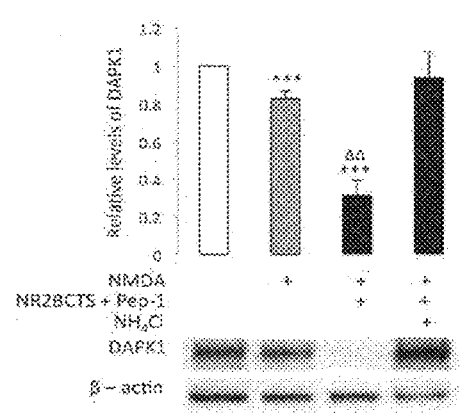
Figure 4E:
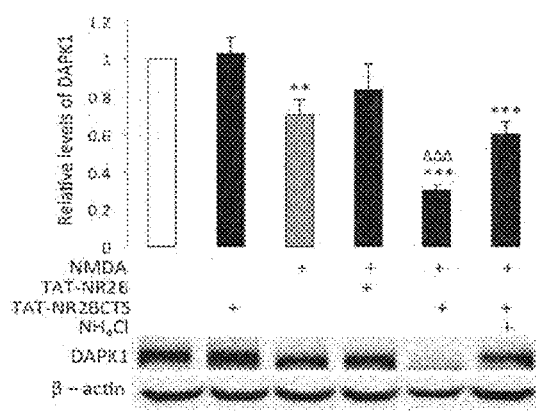

Although the above experiments have demonstrated the ability of recombinant peptide TAT-NR2Bct-CTS to efficiently and conditionally knock-down the active form of native DAPK1 in cells, the requirement of molecular biological apparatuses to express and purify such a recombinant protein at the required quality and amount may limit its widespread use. In addition, the 100 amino acids within the NR2B C-terminal contain multiple proteolytic sites[36] making it vulnerable to fast clearance from the cell, lowering its bioavailability, and increasing the chance of off-target effects. Since the binding to activated DAPK1 by NR2B only requires a short stretch of 18 amino acid residues of NR2B$_{1292-1340}$[20], we designed and synthesized a minimal 28-amino acid DAPK1 degradation targeting peptide, NR2B-CTS, which comprises the DAPK1 binding sequences of NR2B (NR2B1292-1340) and the CTS (FIG. 4a). The TAT cell-penetrating sequence was directly added to the N-terminal of the NR2B-CTS to generate the short synthetic cell-membrane penetrating peptide TAT-NR2B-CTS and its control TAT-NR2B (lacking the CTS sequence) (FIG. 4a). As shown in FIG. 4e, bath application of TAT-NR2B-CTS (25 μM; prior to and during NMDA application) resulted in significant reduction of DAPK1 following NMDA-treatment (n=6; p=0.001 compared to NMDA-treated group), while the TAT-NR2B control peptide did not affect DAPK1 levels (n=5; p=0.223 compared to NMDA-treated group). Again, TAT-NR2B-CTS induced DAPK1 reduction was rescued by NH$_4$Cl application (n=5; p=0.302 compared to NMDA-treated group) (FIG. 4e). Further analysis showed that TAT-NR2B-CTS reduced the levels of DAPK1 in nuclear, cytosolic and mitochondrial fractions (FIG. 7b). siRNA-mediated knockdown of Lamp2a, a crucial component of the CMA machinery, significantly rescued DAPK1 knockdown (FIG. 8), further supporting the mediation by lysosome-dependent degradation. Thus, the synthetic peptide NR2B-CTS, delivered into neurons using the TAT cell-penetrating sequence, is sufficient to rapidly and reversibly reduce the protein levels of active DAPK1 via CMA.

We further showed that other cell-penetrating peptides could replace TAT to make this targeted knockdown method more generalizable. For example, we delivered the small peptide NR2B-CTS (FIG. 4a) to intracellular compartments using the short intracellular delivering carrier peptide, Pep-1, at a ratio of 1:4[23,24]. The NR2B-CTS:Pep-1 complex was administered 1 hour prior to and during NMDA stimulation, and then washed out along with NMDA. As shown in FIG. 4b, 2 hours after NMDA-washout, the levels of endogenous DAPK1 were significantly reduced in a NR2B-CTS concentration dependent manner, being reduced by 33.60±14.48%, 43.65±2.05% and 63.88±6.18% at 10 µM, 25 µM and 50 µM, respectively. Similar to the recombinant peptide TAT-NR2Bct-CTS, NR2B-CTS delivered by Pep-1 did not affect DAPK1 levels in control, non-NMDA treated neurons (FIG. 4b). The reduction of activated DAPK1 was not produced by application of either NR2B-CTS or Pep-1 alone (FIG. 4b; n=4; p=0.941 and p=0.981, respectively, as compared to NMDA-treated group), suggesting that the carrier Pep-1 is not responsible for DAPK1 degradation, but it is required for delivering NR2B-CTS peptide into intracellular compartments of the neurons. Similar to the recombinant TAT-NR2B-CTS, NR2B-CTS delivered with Pep-1 resulted in a rapid and reversible reduction of activated DAPK1 levels. Thus, the DAPK1 reduction was apparent within 1 hour following NMDA and peptide washout (n=3; 58.27±5.48% decrease), reaching a maximum level (n=3; 78.79±1.15% decrease) at 2 hours, and then gradually recovered over the next 4 hours (FIG. 4c). Moreover, NR2B-CTS mediated reduction was fully rescued by application of $NH_4Cl$, further supporting our hypothesis that the reduction in protein levels is a result of increased lysosome-dependent degradation (FIG. 4d).

Accordingly, an exemplary embodiment of the present invention is the use of NR2B-CTS degradation peptides (His-tagged recombinant peptide, or Pep-1 or TAT-mediated synthetic peptides) to rapidly and reversibly degrade its endogenous binding partner DAPK1 in primary neuronal cultures in a dose-, time and condition-dependent manner.

Targeted peptide-mediated reduction of endogenous α-synuclein and PSD95 levels in vitro and in situ. Following confirmation of the success of the targeted peptide-mediated DAPK1 degradation system of the present invention, we showed the generalizability of our method by illustrating the ability of a CTS-containing peptide to mediate lysosomal targeting and degradation of two other proteins, α-synuclein and Post Synaptic Density Protein 95 (PSD95).

α-synuclein, a protein implicated in neurodegenerative synucleinopathies such as Parkinson's disease[18], was recently found to strongly interact with a short amino acid stretch (between amino acids 36-45) of β-synuclein (βsyn36)[19]. Therefore, an exemplary embodiment of the present invention is a short peptide containing both the α-synuclein-binding domain of β-synuclein (βsyn36) and the CTS (FLAG-βsyn36-CTS), which we showed was able to target α-synuclein for lysosomal degradation. In contrast, a peptide (FLAG-βsyn36) containing βsyn36 but not the CTS, while having the ability to interact with α-synuclein, was insufficient for targeting it for lysosomal degradation (FIG. 2a). We showed that 48 hours following co-transfection in HEK cells, co-expression of FLAG-βsyn36-CTS significantly decreased α-synuclein levels in a dose-dependent manner (FIG. 2b; α-synuclein reduced by 32.40%±7.14%, 42.89%±11.34%, 46.49%±5.72% and 52.18%±6.61% of control α-synuclein levels, for co-expression ratios of FLAG-βsyn36-CTS: α-synuclein at 1:1, 2:1, 4:1, 8:1, respectively; n=8). On the contrary, co-transfection of FLAG-βsyn36 did not significantly affect the expression levels of α-synuclein (FIG. 2c; n=4). The FLAG-βsyn36-CTS peptide-induced reduction of α-synuclein was completely rescued by addition of the lysosome inhibitor $NH_4Cl$ (20 mM for 24 hours), indicating that the reduction is a result of increased lysosome-dependent protein degradation (FIG. 2b).

Figures 9A, 9B:
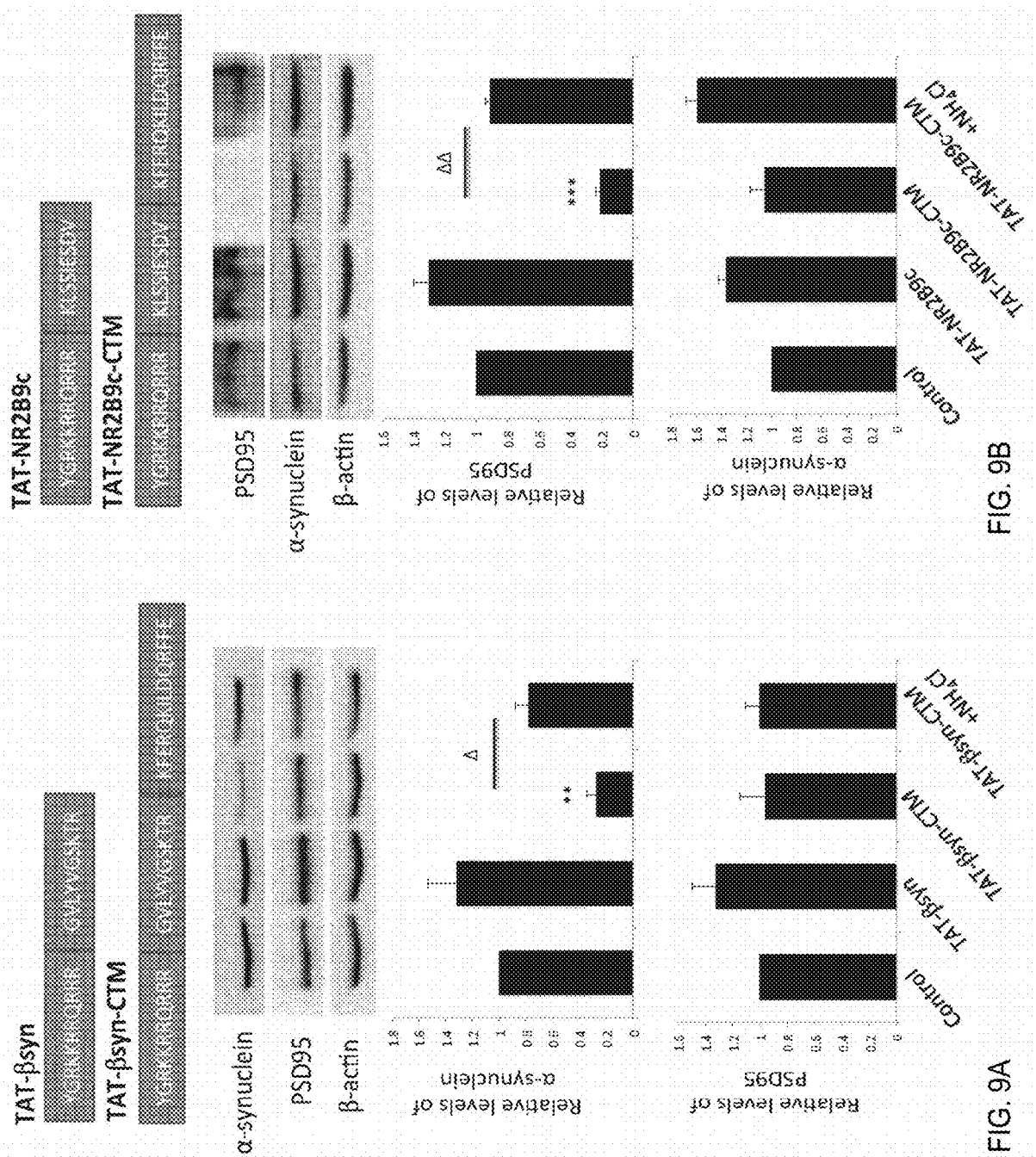
FIG. 9(a-b). Target Peptide-mediated respective degradation of α-synuclein and PSD95 in cultured neurons. (a) Top: Schematics of the synthetic cell-penetrating α-synuclein targeting peptide, TAT-βsyn-CTM, and its control, TAT-βsyn. Middle: Immunoblots demonstrate that TAT-βsyn-CTM (25 μM; n=5), but not the CTM-lacking control peptide TAT-βsyn (25 μM; n=5), specifically decreased the targeted endogenous α-synuclein (One way ANOVA Tukey post-hoc, p<0.001, F(3,16)=12.435), without affecting the level of unrelated control proteins PSD-95 at 4 hours (bottom). This reduction was prevented in the presence of lysosomal inhibitor NH$_4$Cl (20 mM; n=5). Sequences in FIG. 9a: YGRKKRRQRRR (SEQ ID NO:57), GVLYVGSKTR (SEQ ID NO:55), KFERQKILDQRFFE (SEQ ID NO:53), YGRKKRRQRRRGVLYVGSKTR (SEQ ID NO:60), and YGRKKRRQRRRGVLYVGSKTRKFERQKILDQRFFE (SEQ ID NO:2). (b) Top: Schematics of PSD-95 targeting peptide, TAT-NR2B9c-CTM, and control TAT-NR2B9c. Middle: TAT-NR2B9c-CTM (25 μM; n=4), but not Tat-NR2B9c (25 μM; n=4), effectively degraded endogenous PSD95 (One way ANOVA Tukey post-hoc, p<0.001, F(3,12)=18.154) without perturbing untargeted protein α-synuclein (Bottom). NH$_4$Cl rescued PSD95 degradation. Membrane re-probing for β-actin was used as additional specificity and loading controls. Sequences in FIG. 9b: YGRKKRRQRRR (SEQ ID NO:57), KLSSIESDV (SEQ ID NO:51), KFERQKILDQRFFE (SEQ ID NO:53), YGRKKRRQRRRKLSSIESDV (SEQ ID NO:61), and YGRKKRRQRRRKLSSIESDVKFERQKILDQRFFE (SEQ ID NO:52). *p<0.05, ,ΔΔp<0.01 and *p<0.001; bars represent relative mean values±s.e.m. normalized to the naïve non-treated control (arbitrarily set as 1).

We further designed a targeting peptide containing βsyn36 and the CMA-targeting signal or CMA-targeting motif (CTM) (TAT-βsyn-CTM; FIG. 9a, top) to target endogenous α-synuclein in primary cultured neurons. TAT-βsyn-CTM, but not the control TAT-βsyn, was sufficient to target α-synuclein to the lysosome for degradation. Specifically, TAT-βsyn-CTM (25 µM; n=5; p<0.001), but not its control TAT-βsyn (25 µM; n=5), when bath applied, significantly degraded native α-synuclein in primary cultured neurons (FIG. 9a, middle panel). In addition, bath application of TAT-βsyn-CTM degraded native α-synuclein, its intended target, without affecting the non-intended target PSD95 (FIG. 9a, bottom panel). Reduction of α-synuclein levels was rescued by concomitant treatment with the lysosome inhibitor $NH_4Cl$ (FIG. 9a, middle), but not by inhibition of macroautophagy with 3-methyladenine (FIG. 10a), further demonstrating that the reduction in protein levels is a result of increased lysosome-dependent degradation.

Figure 11A:
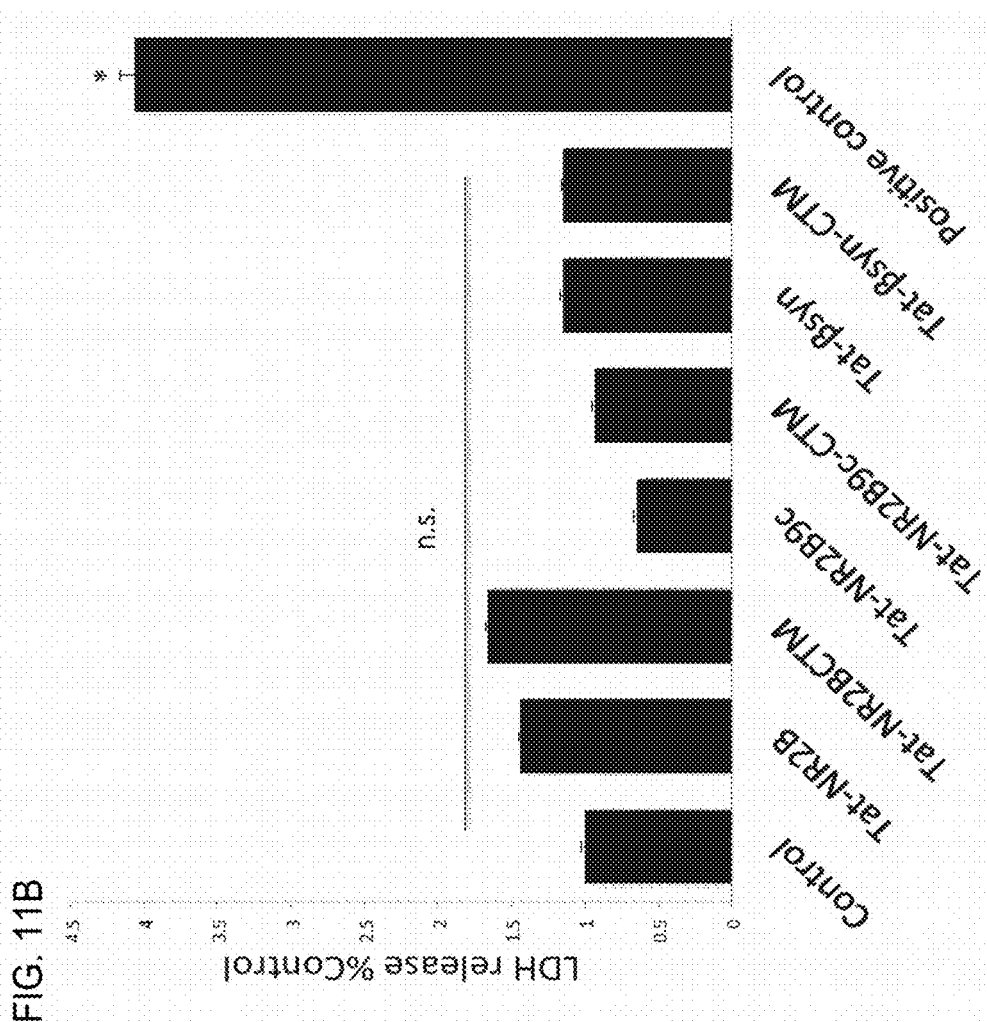
FIG. 11(a-b). Targeting peptides do not show significant cell toxicity 24 hours after treatments. Cortical neurons were treated with 25 μM of (a) recombinant (left, n=4, p=0.005 H(3)=12.706) or (b) synthetic (right, n=4, p<0.001, H(7)=28.074) peptides, and 24 hours later, cell death was assessed by lactate dehydrogenase (LDH) assay. For positive control, cells were lysed with Triton-X 100 as per the manufacture's instruction. Kruskal-Wallis One Way Analysis of Variance on Ranks was used for analysis. *p<0.05. Bars represent relative mean values±s.e.m. normalized to the naïve non-treated control (arbitrarily set as 1). N=4 in each group.
Figure 11B:
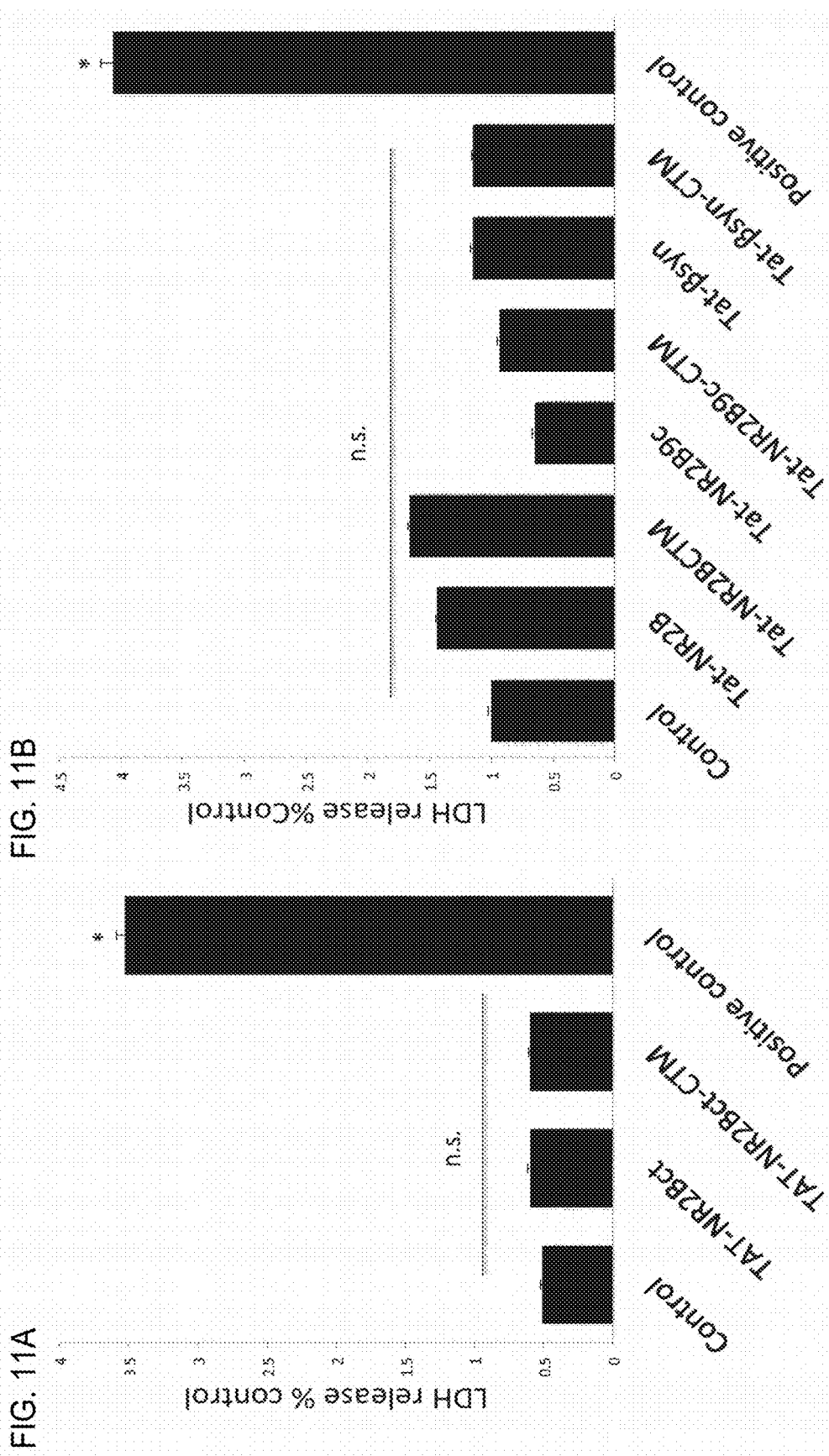

PSD95 is a membrane-associated guanylate kinase (MAGUK) concentrated at glutamatergic synapses and is involved in synapse stabilization and plasticity. PSD95 acts as a scaffold to assemble a specific set of signaling proteins around the NMDAR, and binds to 9 amino acids at the NR2B subunit C-terminal tail[31] (NR2B9c; KLSSIESDV; SEQ ID NO:51). We therefore synthesized the PSD-95 targeting peptide TAT-NR2B9c-CTM (SEQ ID NO:52; FIG. 9b, top). TAT-NR2B9c-CTM, and not the control TAT-NR2B9c, was sufficient to target PSD95 to the lysosome for degradation. Specifically, TAT-NR2B9c-CTM (25 µM; n=4; p<0.01), but not its control TAT-NR2B9c (25 µM; n=4), significantly reduced PSD95 but not α-synuclein levels in a lysosome-dependent fashion (FIG. 9b). Reduction of PSD95 levels was rescued by concomitant treatment with the lysosome inhibitor $NH_4Cl$ (FIG. 9b, bottom), but not by inhibition of macroautophagy with 3-methyladenine (FIG. 10c), further demonstrating that the reduction in protein levels is a result of increased lysosome-dependent degradation. Importantly, none of the βsyn or NR2B9c peptides showed apparent toxicity at the concentrations used, even after 24 hours of application (FIG. 11).

The targeting peptide-mediated degradation of the present invention can therefore be generalized to degrade most, if not all, native cytosolic proteins in situ, and the targeting peptide comprising a protein binding domain is specific for its intended targeted protein.

Neuroprotective actions of targeting peptide-mediated DAPK1 degradation in vitro and in vivo. The above results therefore demonstrate that a targeting peptide comprising a protein binding domain specific for a protein of interest and a CTS can result in the degradation of the protein of interest and that this system can be used to degrade a variety of native proteins. This peptide-mediated reduction of native protein levels can also have physiologically and/or pathologically relevant phenotypes, as described below.

Figure 5A:
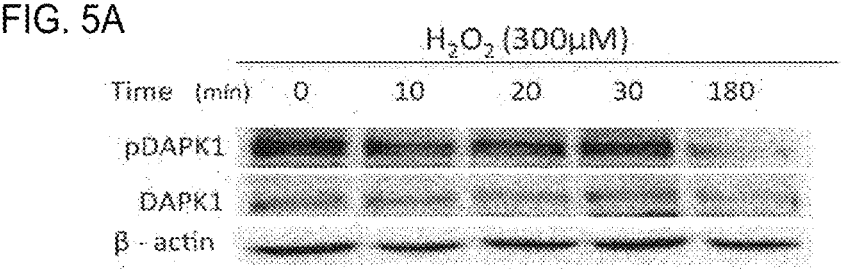
FIG. 5(a-c). TAT-NR2Bct-CTS peptide knocks down $H_2O_2$-activated native DAPK1, protecting neurons against $H_2O_2$-induced neurotoxicity. (a) Immunoblotting for phosphorylated DAPK1 (pDAPK1) revealed a time-dependent activation (reduction in phosphorylation) of native DAPK1 by $H_2O_2$ treatment (300 μM; 30 min; n=4). (b) DAPK1 blotting showed that bath application of TAT-NR2Bct-CTS (36.54±7.1%, n=8; p=0.001, compared with control), but not TAT-NR2Bct (n=7; 89.13±10.78%; p=0.311 compared to control) 60 min prior to and during $H_2O_2$ treatment at 100 μM produced a significant reduction in the level of DAPK1 at 2 hours and this was significantly inhibited by lysosomal inhibitor $NH_4Cl$ (20 mM; n=8; p=0.003, compared to control; and p=0.106, compared to $H_2O_2$ group). Bars represent DAPK1 levels relative to non-treatment naïve group (white bar, arbitrarily set as 1), and compared to naïve group (white bar, *) or $H_2O_2$-treated group (grey bar, $^Δ$). Membrane re-probing for β-actin was used as loading control. (c) LDH cell death assay revealed that $H_2O_2$ treatment (300 μM; 30 min) resulted in a significant increase in neuronal death at 12 hours after treatment (n=4; 2.38±2.70; p=0.001, compared to control), which can be rescued by the addition of $H_2O_2$ decomposition enzyme catalase (n=4; 1.17±1.76; p=0.001, compared to $H_2O_2$ group). This $H_2O_2$-induced neurotoxicity was significantly reduced by treatment of the neurons with TAT-NR2Bct-CTS (50 μM; applied 60 min prior to and maintained throughout the experiments; n=3; 1.56±0.08; p=0.001, compared to $H_2O_2$ group), but not by TAT-NR2Bct (50 μM; n=3; 2.63±17.85; p=0.105, compared to $H_2O_2$ group) or the NMDA receptor antagonist APV (50 μM; n=4; 2.16±13.8; p=0.169 compared to $H_2O_2$ group). *Δp<0.05, $^{ΔΔ}$p<0.01 and *$^{ΔΔΔ}$p<0.001; bars represent relative mean values±s.e.m. normalized to the naïve non-treated control (white bar, arbitrarily set as 1).
Figure 5B:
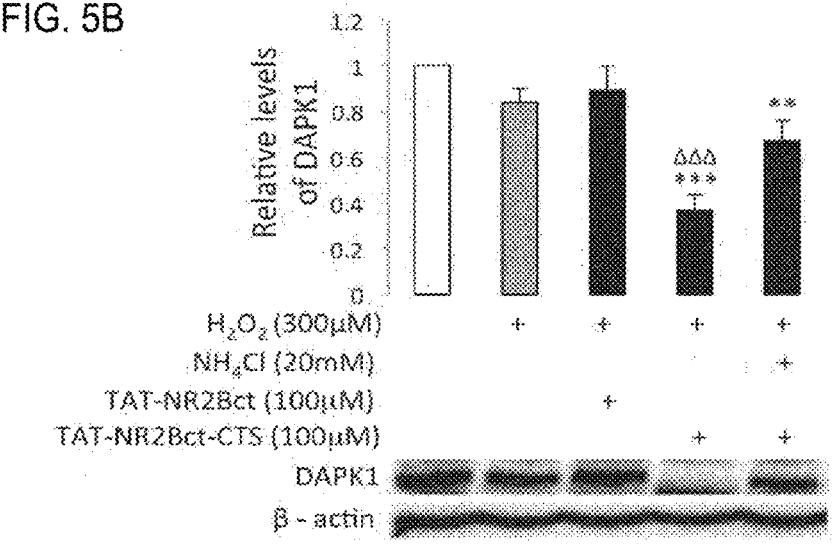
Figure 5C:
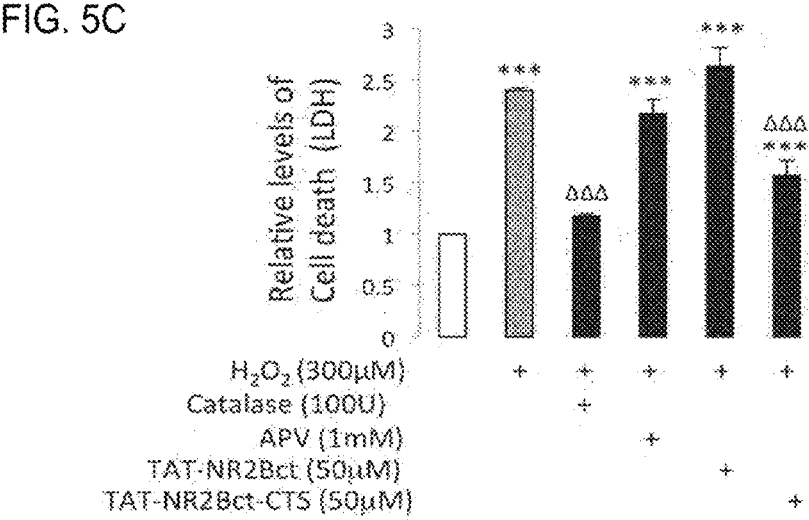

As mentioned above, DAPK1 is a cell death promoting protein kinase in many cell types, and is known to be required for cell death under pathological conditions such as excitotoxic/ischemic neuronal injuries[20] or oxidative stress[25]. Accordingly, an exemplary embodiment is the membrane-permeable DAPK1 knock-down peptides described above, for protecting neurons against various damaging insults by rapidly decreasing the level of activated DAPK1 in the neurons. As NMDA-induced excitotoxic neuronal damage requires DAPK1, it can be prevented by dissociation of the kinase from NMDARs by the membrane permeable NR2B peptide without CTS[20,26]. Hence, it can be difficult to distinguish between the effects of blocking DAPK1-NR2BR protein interaction and the effects of DAPK1 knock-down. To avoid this complication, we demonstrated the neuroprotective effects of DAPK1 knockdown by TAT-NR2Bct-CTS using the non-NMDA receptor-dependent oxidative stress-induced neuronal death, a process that has been implicated in a wide variety of human neurodegenerative conditions, such as Alzheimer's Disease (AD) and Amyotrophic Lateral Sclerosis (ALS)[25]. Oxidative stress is the result of an excess of reactive oxygen species (ROS) production and hence excessive direct exposure of cells to free radicals that can induce subsequent neuronal death. Hydrogen peroxide ($H_2O_2$) is a potent generator of ROS[27] and, exposure of cells to $H_2O_2$ can activate DAPK1, resulting in cell death[28]. As shown in FIG. 5a, exposure of cultured cortical neurons to $H_2O_2$ (300 μM; 30 min) significantly activated DAPK1, as demonstrated by its decreased levels of phosphorylation. In contrast to NMDA, $H_2O_2$ did not significantly affect total DAPK1 (n=8; p=0.125 compared to control). Pretreatment of these neurons with TAT-NR2Bct-CTS, but not TAT-NR2Bct, resulted in a more than 60% reduction in the level of DAPK1 (36.54±7.1%; n=8; p=0.001 compared with control) in $H_2O_2$ treated neurons (FIG. 5b). Consistent with a result of specific lysosomal degradation, the TAT-NR2Bct-CTS induced reduction of DAPK1 was significantly inhibited by $NH_4Cl$ (n=8; p=0.005 compared to TAT-NR2Bct-CTS group) (FIG. 5b). As depicted in FIG. 5c, an LDH (lactate dehydrogenase)-based cell death assay performed 12 hours post-$H_2O_2$ insult revealed that $H_2O_2$ exposure significantly increased neuronal death (n=4; 2.38±2.70; p=0.001 compared to control), and this neuronal damage is reduced by catalase, which catalyzes the decomposition of $H_2O_2$[29] (n=4; 1.17±1.76; p=0.001 compared to $H_2O_2$ group). The $H_2O_2$-induced neurotoxicity was significantly reduced by treating the neurons with TAT-NR2Bct-CTS (50 μM; 60 min prior to and continuously present during and following $H_2O_2$ washout; n=3; 1.56±0.08; p=0.001 compared to $H_2O_2$ group). On the contrary, the same treatment with control peptide TAT-NR2Bct showed no protection (n=3; 2.63±17.85; p=0.105 compared to $H_2O_2$ group). Furthermore, the neuroprotective effect seen with TAT-NR2Bct-CTS is not due to a disruption of DAPK1 from NMDARs by the peptide, as the selective NMDAR antagonist (2R)-amino-5-phosphonovaleric acid (APV) does not protect against $H_2O_2$-induced neurotoxicity (n=4; 2.16±13.8; p=0.169 compared to $H_2O_2$ group). Accordingly, TAT-NR2B-CTS protects neurons against oxidative stress insults via degradation of DAPK1.

We further showed that systemic application of TAT-NR2BCTM can knockdown DAPK1, thereby producing neuroprotection against ischemic insult in vivo, by using a well-characterized rat model of focal ischemia (Middle Carotid Artery Occlusion; MCAO) that was previously shown to reliably activate DAPK1 in vivo[20]. In order to measure the efficacy of DAPK1 knockdown using both western blots and immunocytochemistry, we used a relatively a minor (60 min unilateral occlusion) ischemic insult. As shown in FIG. 12a, rats subjected to 60 min of MCAO were injected intravenously (i.v.) with either saline, TAT-NR2BCTM or TAT-NR2B 1 hour following reperfusion. 2,3,5-triphenyltetrazolium chloride (TTC) staining of transverse brain sections from saline-treated rats revealed that unilateral MCAO reliably induced ischemic brain damage mostly in the ipsilateral striatum (FIG. 12b). As DAPK1 is activated by MCAO-induced ischemic stimulation and the TAT-NR2BCMT knockdown of DAPK1 is DAPK1 activation-dependent, we reasoned that DAPK1 would be maximally activated and degraded in regions most affected by ischemic insult. To determine ischemia-induced knockdown of DAPK1 by TAT-NR2BCTM, we excised tissues from both MCAO-challenged and contralateral sides of the striatum and nearby cortex as indicated in FIG. 12c and immunoblotted for DAPK1 levels. While TATNR2B (10 mg/kg, i.v.) produced no obvious change in the levels of DAPK1 in the brain tissues of either ischemic or contralateral sides, TAT-NR2BCTM (10 mg/kg; i.v.) resulted in a significant reduction in DAPK1 levels only in the ischemic side of the brain; the level of DAPK1 was reduced to 43.3% of that on the contralateral side (FIG. 6d; p<0.001, n=3; two-tailed student's t-test). Given that the collected tissues included some non-infarct areas (FIG. 12c), the actual efficiency of targeting peptide-mediated reduction of DAPK1 levels would be expected to be even greater.

To further assess region-specific DAPK1 degradation in a more straightforward manner, we used immunohistochemistry to probe for DAPK1 in brain transverse brain sections (FIG. 12e, right). As expected, DAPK1 knockdown was specific to stroke-damaged areas, as visualized with Hematoxylin & Eosin (H&E) staining (FIG. 12e, left) of the adjacent sections, which further confirms the in vitro results demonstrating that TAT-NR2BCTM is capable of specific knockdown of the active (but not inactive) form of DAPK1. Although TAT-NR2B also partially decreased ischemic damage by uncoupling DAPK1 from NR2BR signaling complex as previously reported[20], the neuroprotective effect of TAT-NR2BCTM appeared much more prominent (FIG. 12e, left).

Together, the above data provides proof-of-concept evidence for the feasibility of the targeting peptide-based protein knockdown strategy in vivo. Furthermore, the data illustrates the method's utility in achieving region and/or disease specific knockdown of endogenous proteins, depending on the nature of the interaction between targeting peptide and its protein substrate. Finally, given that efficient protein knockdown was obtained following systemic application of the targeting peptide, the data suggests that targeting peptide may be suitable for use in designing clinically relevant therapeutics.

Discussion

In the above experiments and results, a novel targeting peptide-based method is demonstrated to reduce the expression levels of native proteins in cells. This method offers a robust, reversible, dose- and time-dependent and conditional degradation of native proteins. The efficient knockdown of both small (19 kDa, α-synuclein) and large (160 kDa, DAPK1) cytoplasmic proteins, as well as the synaptic scaffolding protein PSD95, further demonstrate the feasibility and versatility of this targeting peptide-based method, providing proof-of-concept evidence for using it to efficiently modulate the expression levels of a number of different endogenous cytosolic proteins for which their binding partners and binding domain sequences are known or can be obtained. For example, this method may be particularly versatile for modulating the expression levels of different cytosolic protein kinases.

Our proof-of-concept experiments with the TAT transducing domain as the CMPD demonstrate that targeting peptides can readily cross the plasma membrane when bath applied in primary cell cultures in vitro or given peripherally in intact animals in vivo, eliminating the need for viral infection. Indeed, we and others have previously shown that TAT can deliver biologically active cargo across the blood brain barrier and plasma membrane into the cell interior in a highly efficient manner both in vitro and in vivo[30,31,32]. However, as demonstrated by the results, the CMPD is not limited to TAT. As Pep-1 can also efficiently deliver the targeting peptide, it appears that TAT can be replaced by alternative cell penetrating peptides (CPP). This is especially useful in cases where covalent linkage between CPP and cargo is not desirable. Compared to previous methods that use small chemicals to control protein levels[3,34,35], peptides can be more easily designed to target a protein for which binding pockets amenable to small molecule inhibition cannot be found[41].

The effectiveness of the method described herein to reduce the levels of endogenous proteins of interest also provides strong supporting evidence that the CMA targeting signal (CTS) used in the present study is capable of targeting a non-CMA substrate protein for CMA-mediated lysosomal degradation, not only when it is directly fused to the target protein, but also when it is indirectly linked to the target protein via a protein-binding peptide containing the CTS. The above results further demonstrate that the targeting peptide comprising a specific protein-binding domain for the target protein is specific for its own intended target protein, with no off-target effect. Importantly, TAT-NR2B-CTS was specific for the active, but not inactive form, of DAPK1, which cannot be achieved by either DNA or mRNA targeting. Further, there is no need to genetically modify a target protein to render it susceptible to degradation. The method of the present invention enables the study of native proteins in situ without prior modification, which precludes potential artifacts arising from genetically manipulating the target protein.

Therefore, the present method described herein for reducing the expression levels of native proteins may be a particularly useful and effective research tool in biomedical studies and can be readily used for clinical applications given its versatility, quick affect on protein levels and its reversibility and dose-dependency. In particular, the peptide can be generated through multiple means; it can either be overexpressed following cDNA plasmid transfection, or expressed and purified as a recombinant protein using common bacterial expression systems or commercially synthesized as short synthetic peptides. Therefore, it is a versatile system which can be widely utilized by almost any biomedical laboratory, even those without sophisticated molecular biological facilities. Furthermore, the method is fast, with the reduction in protein levels being achieved as fast as 1 hour after treatment. Such speed cannot be achieved with any previously described protein manipulations at either the DNA or mRNA levels. The method is, therefore, expected to have fewer issues with the compensation often associated with these slower DNA or mRNA based protein knockdowns. Moreover, the reversibility and dose-dependency means that the level and duration of the protein knock-down can be easily controlled by varying the dose and/or time of the peptide applications, thereby making it a useful and effective research tool in biomedical studies aimed at elucidating the functions of a protein in physiological processes, and in the pathogenesis of diseases. This method is also much more readily translational over previous methods. Many previously described protein knock-down methods often require expression of a pre-genetically modified cDNA into targeted cells with viral infection (in most cases)[1], and are therefore not readily practical for therapeutic use in human patients. However, the use of the TAT cell membrane-penetrating domain or Pep-1 in our method makes the targeting peptide easily deliverable into the interior of cells in various organs under a number of drug delivery routes, including the most commonly used intravenous applications[30,31,32], and therefore, useful for treating human diseases, particularly for those diseases in which the pathogenesis is at least in part caused by gain of function due to an overexpression and/or mutation of a particular protein. Our proof-of-concept experiments with MCAO, a common model for focal ischemia, show that the targeting peptide is capable of knocking-down death-inducing DAPK1 in the brain, but specifically in the damaged areas, leaving DAPK1 in non-ischemic regions intact. The ability to achieve such a disease-related, region-specific knockdown therefore reduces unwanted effects over a general genetic deletion of DAPK1.

An inherent limitation of our CTS-containing peptide strategy is that it may not be useful for manipulating proteins involved in the CMA machinery and lysosomal stability (such as Hsc70 and lamp-2), or for proteins that can inhibit CMA[8]. However, these proteins may be rapidly knocked down by harnessing other cellular protein degradation systems (such as proteasomes) using a similar targeting peptide strategy. To this end, a short amino-acid based strong proteasome targeting signal has recently been described[3]. Furthermore, since the method described herein uses the endosome-lysosome system in place of the proteasome, this method may be used to complement other protein knock-down methods. For example, a combination of a peptide containing CTS and a peptide containing proteasomal-targeting signals may dramatically enhance the knock-down efficiency of certain proteins. Moreover, the present method can also be especially powerful under pathological conditions where the cell is under stress and/or the proteasome is inhibited.

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the scope of the invention. All such modifications as would be apparent to one skilled in the art are intended to be included within the scope of the following claims.

SEQUENCE LISTINGS

SEQ ID NO:1 (targeted knockdown peptide targeting α-synuclein, without TAT PTD. The CMA-targeting signal (CTS) is underlined):

(SEQ ID NO: 1)
GVLYVGSKTRKFERQKILDQRFFE

SEQ ID NO:2 (targeted knockdown peptide targeting α-synuclein, with TAT PTD (italics). The CMA-targeting signal (CTS) is underlined):

(SEQ ID NO: 2)
YGRKKRRQRRRGVLYVGSKTRKFERQKILDQRFFE

SEQ ID NO:3 (targeted knockdown peptide targeting DAPK1, without TAT PTD. The CMA-targeting signal (CTS) is underlined):

```
                                              (SEQ ID NO: 3)
KKNRNKLRRQHSYKFERQKILDQRFFE
```

SEQ ID NO:4 (targeted knockdown peptide targeting DAPK1, with TAT PTD (italics). The CMA-targeting signal (CTS) is underlined):

```
                                              (SEQ ID NO: 4)
YGRKKRRQRRRKKNRNKLRRQHSYKFERQKILDQRFFE

SEQ ID NO: 26:
                                              (SEQ ID NO: 26)
KFERQ

SEQ ID NO: 51:
                                              (SEQ ID NO: 51)
KLSSIESDV
```

SEQ ID NO:52 (targeted knockdown peptide targeting PSD95, with TAT PTD (italics). The CMA-targeting signal (CTS) is underlined):

```
                                              (SEQ ID NO: 52)
YGRKKRRQRRRKLSSIESDVKFERQKILDQRFFE
```

REFERENCES

1. Banaszynski, L. A. & Wandless, T. J. Conditional Control of Protein Function. *Chemistry & Biology* 13, 11-21 (2006).
2. Castanotto, D. & Rossi, J. J. The promises and pitfalls of RNA-interference-based therapeutics. *Nature* 457, 426-433 (2009).
3. Bonger, K. M., Chen, L.-C., Liu, C. W. & Wandless, T. J. Small-molecule displacement of a cryptic degron causes conditional protein degradation. *Nature Chemical Biology* 7, 531-537 (2011).
4. Banaszynski, L. A., Chen, L.-C., Maynard-Smith, L. A., Ooi, A. G. L. & Wandless, T. J. A Rapid, Reversible, and Tunable Method to Regulate Protein Function in Living Cells Using Synthetic Small Molecules. *Cell* 126, 995-1004 (2006).
5. Neklesa, T. K. et al. Small-molecule hydrophobic tagging-induced degradation of HaloTag fusion proteins. *Nature Chemical Biology* 7, 538-543 (2011).
6. Hannah, J. & Zhou, P. Maximizing target protein ablation by integration of RNAi and protein knockout. *Nature Publishing Group* 21, 1152-1154 (2011).
Fred, D. J. Peptide sequences that target cytosolic proteins for lysosomal proteolysis. *Trends in biochemical sciences* 15, 305-309 (1990).
8. Majeski, A. E. & Fred, D. J. Mechanisms of chaperone-mediated autophagy. *The International Journal of Biochemistry & Cell Biology* 36, 2435-2444 (2004).
9. Backer, J., Bourret, L. & Dice, J. F. Regulation of catabolism of microinjected ribonuclease A requires the amino-terminal 20 amino acids. *Proc Natl Acad Sci* 80, 2166-2170 (1983).
10. Cuervo, A. M. & Dice, J. F. Unique properties of lamp2a compared to other lamp2 isoforms. *J. Cell. Sci.* 113 Pt 24, 4441-4450 (2000).
11. Slot, L. A., Lauridsen, A.-M. & Hendil, K. Intracellular protein degradation in serum-deprived human fibroblasts. *Journal of Biochemistry* 237, 491-498 (1986).
12. Seglen, P. O. & Reith, A. Ammonia inhibition of protein degradation in isolated rat hepatocytes. Quantitative ultrastructural alterations in the lysosomal system. *Exp. Cell Res.* 100, 276-280 (1976).
13. Bauer, P. O. et al. Harnessing chaperone-mediated autophagy for the selective degradation of mutant huntingtin protein. *Nat. Biotechnol.* 28, 256-263 (2010).
14. Cataldo, A. M. & Nixon, R. A. Enzymatically active lysosomal proteases are associated with amyloid deposits in Alzheimer brain. *Proc. Natl. Acad. Sci. U.S.A.* 87, 3861-3865 (1990).
15. Neff, N. T., Bourret, L., Miao, P. & Dice, J. F. Degradation of proteins microinjected into IMR-90 human diploid fibroblasts. *The Journal of cell biology* 91, 184-194 (1981).
16. Cuervo, A. M. Impaired Degradation of Mutant-Synuclein by Chaperone-Mediated Autophagy. *Science* 305, 1292-1295 (2004).
17. Cuervo, A. M., Terlecky, S. R., Dice, J. F. & Knecht, E. Selective binding and uptake of ribonuclease A and glyceraldehyde-3-phosphate dehydrogenase by isolated rat liver lysosomes. *J. Biol. Chem.* 269, 26374-26380 (1994).
18. Spillantini, M. G. et al. α-Synuclein in Lewy bodies. *Nature* 388, 839-840 (1997).
19. Shaltiel-Karyo, R. et al. Inhibiting α-Synuclein Oligomerization by Stable Cell-Penetrating β-Synuclein Fragments Recovers Phenotype of Parkinson's Disease Model Flies. *PLoS ONE* 5, e13863 (2010).
20. Tu, W. et al. DAPK1 Interaction with NMDA Receptor NR2B Subunits Mediates Brain Damage in Stroke. *Cell* 140, 222-234 (2010).
21. Cohen, O., Feinstein, E. & Kimchi, A. DAP-kinase is a Ca2+/calmodulin-dependent, cytoskeletal-associated protein kinase, with cell death-inducing functions that depend on its catalytic activity. *The EMBO journal* 16, 998-1008 (1997).
22. Shamloo, M. et al. Death-associated protein kinase is activated by dephosphorylation in response to cerebral ischemia. *J. Biol. Chem.* 280, 42290-42299 (2005).
23. Morris, M. C., Depollier, J Mery, J., Heitz, F. & Divita, G. A peptide carrier for the delivery of biologically active proteins into mammalian cells. *Nat. Biotechnol.* 19, 1173-1176 (2001).
24. Wang, Y. -Amino-3-hydroxy-5-methylisoxazole-4-propionic Acid Subtype Glutamate Receptor (AMPAR) Endocytosis Is Essential for N-Methyl-D-aspartate-induced Neuronal Apoptosis. *Journal of Biological Chemistry* 279, 41267-41270 (2004).
25. Barnham, K. J., Masters, C. L. & Bush, A. I. Neurodegenerative diseases and oxidative stress. *Nat Rev Drug Discov* 3, 205-214 (2004).
26. Martin, H. G. S. & Wang, Y. T. Blocking the Deadly Effects of the NMDA Receptor in Stroke. *Cell* 140, 174-176 (2010).
27. Gilgun-Sherki, Y., Melamed, E. & Offen, D. Oxidative stress induced-neurodegenerative diseases: the need for antioxidants that penetrate the blood brain barrier. *Neuropharmacology* 40, 959-975 (2001).
28. Eisenberg-Lerner, A. & Kimchi, A. DAP kinase regulates JNK signaling by binding and activating protein kinase D under oxidative stress. *Cell Death Differ* 14, 1908-1915 (2007).
29. Ricart, K. C. & Fiszman, M. L. Hydrogen peroxide-induced neurotoxicity in cultured cortical cells grown in serum-free and serum-containing media. *Neurochem. Res.* 26, 801-808 (2001).
30. Vivès, E., Brodin, P. & Lebleu, B. A truncated HIV-1 Tat protein basic domain rapidly translocates through the plasma membrane and accumulates in the cell nucleus. *J. Biol. Chem.* 272, 16010-16017 (1997).

31. Aarts, M. et al. Treatment of ischemic brain damage by perturbing NMDA receptor-PSD-95 protein interactions. *Science* 298, 846 (2002).
32. Brebner, K. Nucleus Accumbens Long-Term Depression and the Expression of Behavioral Sensitization. *Science* 310, 1340-1343 (2005).
33. Hill, M. Evaluating Neuroprotection in Aneurysm Coiling Therapy (ENACT) Trial Final Results. *International Stroke Conference* (2012).
34. Banaszynski, L. A., Sellmyer, M. A., Contag, C. H., Wandless, T. J. & Thorne, S. H. Chemical control of protein stability and function in living mice. *Nature Medicine* 14, 1123-1127 (2008).
35. Sakamoto, K. M. et al. Protacs: chimeric molecules that target proteins to the Skp1-Cullin-F box complex for ubiquitination and degradation. *Proc. Natl. Acad. Sci. U.S.A.* 98, 8554-8559 (2001).
36. Traynelis, S. F. et al. Glutamate Receptor Ion Channels: Structure, Regulation, and Function. *Pharmacological Reviews* 62, 405-496 (2010).
37. Taghibiglou, C. et al. Role of NMDA receptor-dependent activation of SREBP1 in excitotoxic and ischemic neuronal injuries. *Nature Medicine* 1-9 (2009). doi:10.1038/nm.2064.
38. Vivès, E. Present and future of cell-penetrating peptide mediated delivery systems: "Is the Trojan horse too wild to go only to Troy?" *Journal of Controlled Release* 109, 77-85 (2005).
39. Vivès, E. et al. Cell-penetrating and cell-targeting peptides in drug delivery. *Biochimica et Biophysica Acta* 1786, 126-138 (2008).
40. Rajendran, L. et al. Subcellular targeting strategies for drug design and delivery. *Nature Reviews* 9, 29-42 (2010).

The embodiments of the invention in which an exclusive property or privilege is claimed are defined as follows:

1. A peptide comprising:
   (a) a chaperone-mediated autophagy (CMA)-targeting signal domain, wherein the CMA-targeting signal domain comprises amino acids 25-38 of SEQ ID NO: 4;
   (b) a protein-binding domain that selectively binds to an active form of a target cytosolic protein; and
   (c) a cell-membrane penetrating domain,
   wherein the peptide comprises SEQ ID NO:2 or SEQ ID NO:4.

2. The peptide of claim 1, wherein the peptide comprises the amino acid sequence of SEQ ID NO:4.

3. The peptide of claim 1, wherein the target protein is an endogenous protein in a cell, and wherein the peptide is for reducing the intracellular expression level of the endogenous target protein, and wherein the reduction in the intracellular expression of the target protein is reversible.

4. The peptide of claim 1, wherein the peptide comprises the amino acid sequence of SEQ ID NO:2.

5. The peptide of claim 1, wherein the peptide consists of SEQ ID NO:2.

6. The peptide of claim 1, wherein the peptide consists of SEQ ID NO:4.

7. A peptide comprising:
   (a) a chaperone-mediated autophagy (CMA)-targeting signal domain;
   (b) a protein-binding domain, wherein the protein binding domain comprises an amino acid sequence that selectively binds to Post Synaptic Density Protein 95 (PSD95) and wherein the protein binding domain comprises SEQ ID NO:27; and
   (c) a cell-membrane penetrating domain.

8. The peptide of claim 7, wherein the chaperone-mediated autophagy (CMA)-targeting signal domain comprises SEQ ID NO: 26.

9. The peptide of claim 7, wherein the chaperone-mediated autophagy (CMA)-targeting signal domain comprises amino acids 25-38 of SEQ ID NO: 4.

10. The peptide of claim 7, wherein the peptide is for reducing the intracellular expression level of PSD95, and wherein the reduction in the intracellular expression of PSD95 is reversible.

11. The peptide of claim 7, wherein the protein binding domain consists of SEQ ID NO:27.

* * * * *